United States Patent
Chan et al.

(10) Patent No.: US 9,434,677 B2
(45) Date of Patent: *Sep. 6, 2016

(54) NATURAL AND SYNTHETIC COMPOUNDS FOR TREATING CANCER AND OTHER DISEASES

(75) Inventors: Pui-Kwong Chan, Sugarland, TX (US); May Sung Mak, Hong Kong (CN)

(73) Assignee: PACIFIC ARROW LIMITED, Hong Kong (HK)

( * ) Notice: Subject to any disclaimer, the term of this patent is extended or adjusted under 35 U.S.C. 154(b) by 41 days.

This patent is subject to a terminal disclaimer.

(21) Appl. No.: 14/233,031

(22) PCT Filed: Jul. 13, 2012

(86) PCT No.: PCT/US2012/046716
§ 371 (c)(1),
(2), (4) Date: Feb. 14, 2014

(87) PCT Pub. No.: WO2013/012737
PCT Pub. Date: Jan. 24, 2013

(65) Prior Publication Data
US 2014/0199378 A1    Jul. 17, 2014

Related U.S. Application Data

(63) Continuation-in-part of application No. PCT/US2011/044233, filed on Jul. 15, 2011, which is a continuation-in-part of application No. PCT/US2010/042240, filed on Jul. 16, 2010, application No. 14/233,031, which is a continuation-in-part of application No. 12/856,322, filed on Aug. 13, 2010, now Pat. No. 8,586,719.

(60) Provisional application No. 61/226,043, filed on Jul. 16, 2009.

(51) Int. Cl.
| A61K 31/575 | (2006.01) |
| C07J 9/00 | (2006.01) |
| C07H 15/256 | (2006.01) |
| C07C 13/62 | (2006.01) |
| C07C 69/732 | (2006.01) |
| C07C 67/60 | (2006.01) |
| G01N 33/50 | (2006.01) |
| C07H 15/24 | (2006.01) |
| C07J 63/00 | (2006.01) |
| A61K 9/127 | (2006.01) |

(52) U.S. Cl.
CPC .............. *C07C 69/732* (2013.01); *A61K 9/127* (2013.01); *C07C 67/60* (2013.01); *C07H 15/24* (2013.01); *C07J 63/008* (2013.01); *G01N 33/5008* (2013.01)

(58) Field of Classification Search
None
See application file for complete search history.

(56) References Cited

U.S. PATENT DOCUMENTS

| 6,197,306 B1 | 3/2001 | Murali et al. |
| 6,231,859 B1 | 5/2001 | Kensil |
| 6,444,233 B1 | 9/2002 | Arntzen et al. |
| 6,689,398 B2 | 2/2004 | Haridas et al. |
| 6,746,696 B2 | 6/2004 | Arntzen et al. |
| 6,962,720 B2 | 11/2005 | Haridas et al. |
| 7,105,186 B2 | 9/2006 | Arntzen et al. |
| 7,189,420 B2 | 3/2007 | Wang |
| 7,262,285 B2 | 8/2007 | Chan et al. |

(Continued)

FOREIGN PATENT DOCUMENTS

| JP | 61-007285 | 1/1986 |
| JP | 61-130232 | 6/1986 |

(Continued)

OTHER PUBLICATIONS

Bao-Ning Phytochemistry 64 (2003) 293-302.*
PCT Written Opinion of the International Searching Authority for PCT/US04/33359, filed Oct. 8, 2004 for Pacific Arrow Limited et al., dated May 17, 2005. (ws:80) [Exhibit 12].
PCT International Search Report for PCT/US04/33359, filed Oct. 8, 2004 for Pacific Arrow Limited et al., dated Apr. 12, 2005. (ws:79) [Exhibit 11].
PCT Written Opinion of the International Searching Authority for PCT/US04/43465, filed Dec. 23, 2004 for Pacific Arrow Limited et al., dated May 17, 2005. (ws:80) [Exhibit 12 ].
PCT International Search Report for PCT/US04/43465, filed Dec. 23, 2004 for Pacific Arrow Limited et al., dated May 17, 2005. (ws:81) [Exhibit 13].

(Continued)

*Primary Examiner* — Jeffrey S Lundgren
*Assistant Examiner* — Michael Schmitt
(74) *Attorney, Agent, or Firm* — Law Offices of Albert Wai-Kit Chan, PLLC

(57) ABSTRACT

This invention provides a method of synthesizing new active compounds for pharmaceutical uses including cancer treatment, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers. This invention is an anti-adhesion therapy which uses the compound as a mediator or inhibitor of adhesion proteins and angiopoietins. It inhibits excess adhesion and inhibits cell attachment. It modulates angiogenesis. The compounds also use as mediator of cell adhesion receptor, cell circulating, cell moving and inflammatory diseases. The compounds are attached with angeloyl, acetyl, tigloyl, senecioyl, Crotonoyl, 3,3-Dimethylartyloyl, Cinnamoyl, Pentenoyl, Hexanoyl, benzoyl, Ethylbutyryl, benzoyl, dibenzoyl, alkanoyl, alkenoyl, benzoyl alkyl substituted alkanoyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, O—C(2-18) Acyl.

34 Claims, 12 Drawing Sheets

(56) References Cited

U.S. PATENT DOCUMENTS

Figure 1:
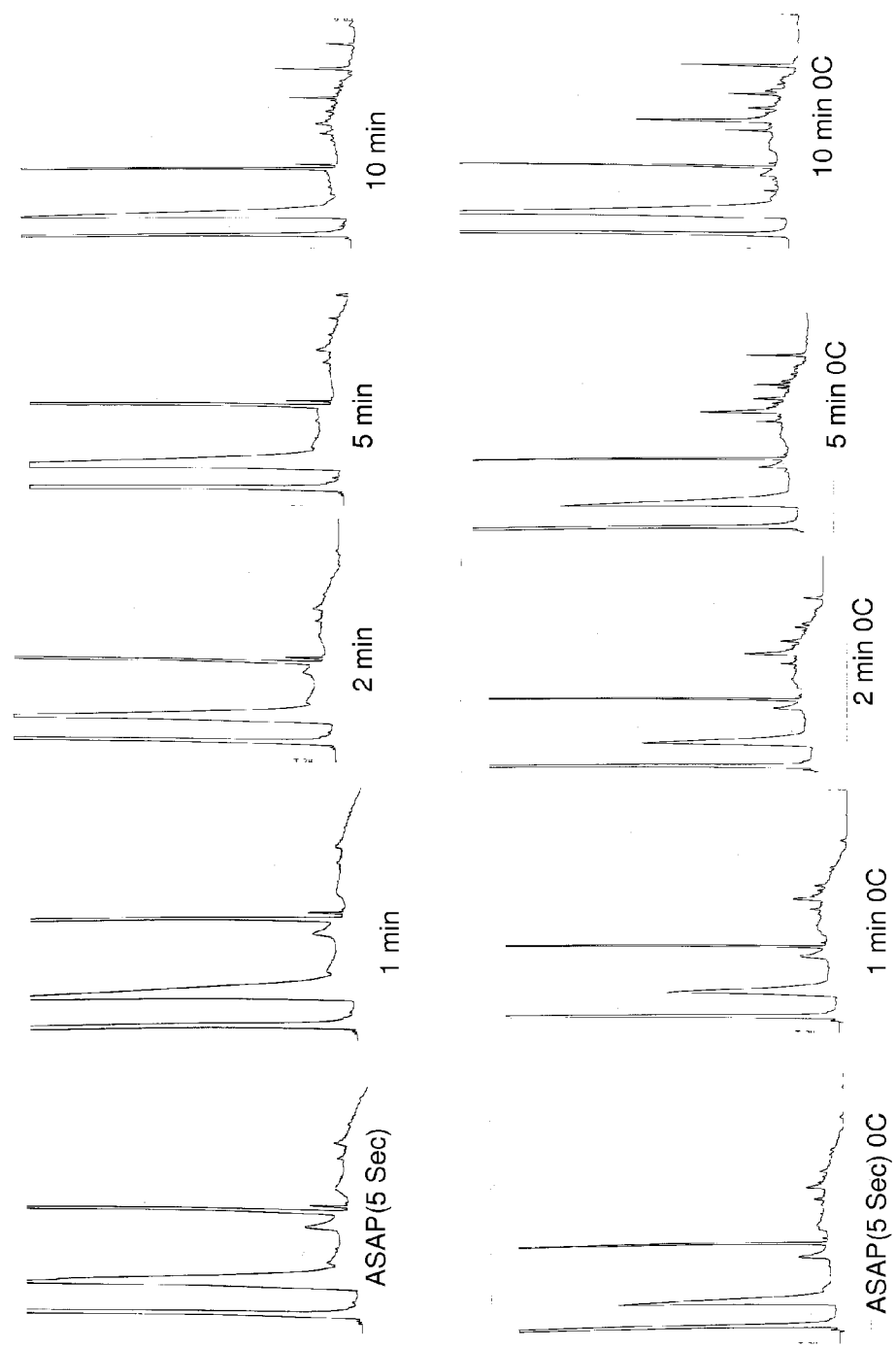

| | | | |
|---|---|---|---|
| 7,488,753 | B2 | 2/2009 | Chan et al. |
| 7,514,412 | B2 | 4/2009 | Chan et al. |
| 7,524,824 | B2 | 4/2009 | Chan et al. |
| 7,670,632 | B2 | 3/2010 | Arntzen et al. |
| 7,727,561 | B2 | 6/2010 | Chan et al. |
| 7,780,974 | B2 | 8/2010 | Gutterman |
| 8,334,269 | B2 | 12/2012 | Chan et al. |
| 8,586,719 | B2 | 11/2013 | Chan et al. |
| 8,614,197 | B2 | 12/2013 | Chan et al. |
| 8,735,558 | B2 | 5/2014 | Chan et al. |
| 8,785,405 | B2 | 7/2014 | Chan et al. |
| 8,841,265 | B2 | 9/2014 | Chan et al. |
| 8,859,012 | B2 | 10/2014 | Chan et al. |
| 2003/0082293 | A1 | 5/2003 | Wang et al. |
| 2003/0096030 | A1 | 5/2003 | Wang et al. |
| 2004/0138151 | A1 | 7/2004 | Maes et al. |
| 2005/0209445 | A1 | 9/2005 | Gokaraju et al. |
| 2006/0183687 | A1 | 8/2006 | Cory et al. |
| 2007/0196517 | A1 | 8/2007 | San Martin |
| 2007/0212329 | A1 | 9/2007 | Bruck et al. |
| 2007/0243269 | A1 | 10/2007 | McNeff et al. |
| 2007/0249711 | A1 | 10/2007 | Choi et al. |
| 2007/0254847 | A1 | 11/2007 | Liu et al. |
| 2008/0058273 | A1 | 3/2008 | Yang et al. |
| 2008/0064762 | A1 | 3/2008 | Fuchs et al. |
| 2008/0096938 | A1 | 4/2008 | Evindar et al. |
| 2008/0112925 | A1 | 5/2008 | Hancock |
| 2008/0119420 | A1 | 5/2008 | Liu et al. |
| 2013/0190261 | A1 | 7/2013 | Chan et al. |
| 2013/0338089 | A1 | 12/2013 | Chan et al. |
| 2014/0199378 | A1 | 7/2014 | Chan et al. |
| 2014/0322810 | A1 | 10/2014 | Chan et al. |

FOREIGN PATENT DOCUMENTS

| | | |
|---|---|---|
| JP | 02-247196 | 10/1990 |
| JP | 2002-515430 A | 5/2002 |
| WO | WO 2000/38700 A1 | 7/2000 |
| WO | WO 2006/029221 | 3/2006 |
| WO | Wo 2006/116656 | 11/2006 |
| WO | WO 2008/028060 A2 | 3/2008 |
| WO | WO 2011/009032 | 1/2011 |
| WO | WO 2011009032 A1 * | 1/2011 |

OTHER PUBLICATIONS

PCT International Search Report issued on Feb. 6, 2007 for Pacific Arrow Limited, International App'l No. PCT/US2005/031900. (ws:102) [Exhibit 14].

PCT Written Opinion of the International Searching Authority issued on Feb. 6, 2007 for Pacific Arrow Limited, International App'l No. PCT/US2005/031900. (WS:103) [Exhibit 15].

PCT International Preliminary Report on Patentability issued on Mar. 22, 2007 for Pacific Arrow Limited, International App'l No. PCT/US2005/031900. (ws:104) [Exhibit 16].

PCT International Preliminary Report on Patentability issued on Apr. 11, 2006 for Pacific Arrow Limited, International App'l No. PCT/US2004/033359. (ws:194) [Exhibit 17].

PCT International Search Report issued on Nov. 13, 2006 for Pacific Arrow Limited, International App'l No. PCT/US2006/016158. (ws:106) [Exhibit 18].

PCT Written Opinion of the International Searching Authority issued on Nov. 13, 2006 for Pacific Arrow Limited, International App'l No. PCT/US2006/016158. (ws:107) [Exhibit 19].

U.S. Office Action for Chan, et al., U.S. Appl. No. 11/131,551, filed May 17, 2005, Dated Jan. 22, 2007. (ws:136) [Exhibit 20].

U.S. Notice of Allowability for Chan, et al., U.S. Appl. No. 11/131,551, filed May 17, 2005, Dated May 11, 2007. (ws:137) [Exhibit 21].

U.S. Office Action for Chan, et al., U.S. Appl. No. 11/289,142, filed Nov. 28, 2005, Dated Sep. 27, 2007. (ws:138) [Exhibit 22].

U.S. Office Action for Chan, et al., U.S. Appl. No. 11/267,523, filed Nov. 4, 2005, Dated Sep. 27, 2007. (ws:139) [Exhibit 23].

U.S. Office Action for Chan, et al., U.S. Appl. No. 10/906,303, filed Feb. 14, 2005, Dated Feb. 12, 2007. (ws:140) [Exhibit 24].

U.S. Office Action for Chan, et al., U.S. Appl. No. 10/906,303, filed Feb. 14, 2005, Dated Jul. 27, 2007. (ws:141) [Exhibit 25].

U.S. Office Action for Chan, et al., U.S. Appl. No. 11/117,760, filed Apr. 27, 2005, Dated Jun. 29, 2007. (ws:142) [Exhibit 26].

U.S. Office Action for Chan, et al., U.S. Appl. No. 11/117,760, filed Apr. 27, 2005, Dated Aug. 20, 2007. (ws:143) [Exhibit 27].

PCT International Preliminary Report on Patentability for Pacific Arrow Limited, et al., International Application No. PCT/US2006/016158, filed Apr. 27, 2006, Dated Oct. 30, 2007 (ws:147) [Exhibit 28].

U.S. Office Action for Chan, et al., U.S. Appl. No. 11/117,745, filed Apr. 27, 2005, Dated Jan. 25, 2008. (ws:148) [Exhibit 29].

U.S. Office Communication for Chan, et al., U.S. Appl. No. 11/117,760, filed Apr. 27, 2005, Dated Feb. 8, 2008. (ws:149) [Exhibit 30].

U.S. Office Action for Chan, et al., U.S. Appl. No. 11/289,142, filed Nov. 28, 2005, Dated Apr. 14, 2008. (ws:151) [Exhibit 31].

U.S. Office Action for Chan, et al., U.S. Appl. No. 11/117,745, filed Apr. 27, 2005, Dated Mar. 12, 2007. (ws:153) [Exhibit 32].

U.S. Office Action for Chan, et al., U.S. Appl. No. 11/117,745, filed Apr. 27, 2005, Dated Aug. 22, 2007. (ws:154) [Exhibit 33].

PCT International Preliminary Report on Patentability issued on Feb. 7, 2006 for Pacific Arrow Limited, International App'l No. PCT/US2004/043465. (ws:155) [Exhibit 34].

U.S. Office Action for Chan, et al., U.S. Appl. No. 10/906,303, filed Feb. 14, 2005, Dated Jan. 4, 2008. (ws:160) [Exhibit 35].

PCT International Search Report issued on Jul. 7, 2008 for Pacific Arrow Limited, International App'l No. PCT/US08/02086. (ws:203) [Exhibit 36].

PCT Written Opinion of the International Searching Authority issued on Jul. 7, 2008 for Pacific Arrow Limited, International App'l No. PCT/US US08/02086. (ws:204) [Exhibit 37].

PCT International Search Report for Pacific Arrow Limited et al., International App'l No. PCT/US07/77273, filed Aug. 30, 2007, Dated Aug. 4, 2008. (ws:208) [Exhibit 38].

PCT Written Opinion of the International Searching Authority for Pacific Arrow Limited et al., International App'l No. PCT/US07/77273, filed Aug. 30, 2007, Dated Aug. 4, 2008. (ws:209) [Exhibit 39].

U.S. Advisory Action for Chan, et al., U.S. Appl. No. 11/289,142, filed Nov. 28, 2005, Dated Jul. 28, 2008. (ws:210) [Exhibit 40].

Notice of Allowability for Chan et al., U.S. Appl. No. 10/906,303, filed Feb. 14, 2005, dated Nov. 26, 2008. (ws:215) [Exhibit 41].

Notice of Allowability for Chan et al., U.S. Appl. No. 11/117,745, filed Apr. 27, 2005, dated Dec. 2, 2008. (ws:216) [Exhibit 42].

Notice of Allowability for Chan et al., U.S. Appl. No. 11/289,142, filed Nov. 28, 2005, dated Oct. 1, 2008. (ws:220) [Exhibit 43].

U.S. Office Action for Chan, et al., U.S. Appl. No. 11/117,760, filed Apr. 27, 2005, Dated Mar. 18, 2009. (ws:233) [Exhibit 44]

U.S. Office Action for Chan, et al., U.S. Appl. No. 11/683,198, filed Mar. 7, 2007, Dated May 1, 2009. (ws:234) [Exhibit 45].

PCT Written Opinion of the International Searching Authority for PCT/US09/34115, filed Feb. 13, 2009 for Pacific Arrow Limited et al., dated Jun. 2, 2009. (ws:237) [Exhibit 46].

PCT Written Opinion of the International Searching Authority for PCT/US07/77273, filed Aug. 30, 2007 for Pacific Arrow Limited et al., dated Aug. 4, 2008. (ws:238) [Exhibit 47].

PCT Written Opinion of the International Searching Authority, for PCT/US09/34115, filed Feb. 13, 2009 for Pacific Arrow Limited et al., dated Jun. 2, 2009. (ws:239) [Exhibit 48].

PCT Preliminary Report on Patentability for PCT/US2007/077273, filed Aug. 30, 2007 for Pacific Arrow Limited et al., dated Mar. 12, 2009. (ws:240) [Exhibit 49].

U.S. Office Action for Chan, et al., U.S. Appl. No. 11/683,198, filed Mar. 7, 2007, Dated Feb. 18, 2010. (ws:258) [Exhibit 50].

PCT International Search Report for PCT/US2009/034115, filed Feb. 13, 2009 for Pacific Arrow Limited et al., dated Jun. 2, 2009. (ws:261) [Exhibit 51].

PCT Preliminary Report on Patentability for PCT 2009/034115, filed Feb. 13, 2009 for Pacific Arrow Limited et al., dated Aug. 26, 2010. (ws:278) [Exhibit 52].

(56) References Cited

OTHER PUBLICATIONS

PCT Written Opinion of the International Searching Authority for PCT/US09/34115, filed Feb. 13, 2009 for Pacific Arrow Limited et al., dated Jun. 2, 2009. (ws:279) [Exhibit 53].
PCT Written Opinion of the International Searching Authority for PCT/US10/42220, filed Jul. 16, 2010 for Pacific Arrow Limited et al., dated Sep. 2, 2010. (ws:280) [Exhibit 54].
PCT International Search Report for PCT/US10/42240, filed Jul. 16, 2010 for Pacific Arrow Limited et al., dated Sep. 2, 2010. (ws:281) [Exhibit 55].
U.S. Office Action for Chan, et al., U.S. Appl. No. 11/683,198, filed Mar. 7, 2007, Dated Sep. 10, 2008. (ws:282) [Exhibit 56].
U.S. Office Action, Jan. 19, 2011, for Chan et al., U.S. Appl. No. 12/344,682, filed Dec. 29, 2008. (ws:289) [Exhibit 57].
U.S. Office Action, May 20, 2011, for Chan et al., U.S. Appl. No. 12/392,795, filed Feb. 25, 2009. (ws:303) [Exhibit 58].
Notice of Allowability for Chan et al., U.S. Appl. No. 11/683,198, filed Mar. 7, 2007, Dated May 5, 2011. (ws:304) [Exhibit 59].
Office Action, May 12, 2011, for Chan et al., U.S. Appl. No. 12/714,598, filed Mar. 1, 2010. (ws:311) [Exhibit 60].
U.S. Office Action, Oct. 27, 2011, for Chan et al., U.S. Appl. No. 12/344,682, filed Dec. 29, 2008. (ws:316) [Exhibit 61].
PCT Written Opinion of thw International Searching Authority, Dec. 6, 2011, for Pacific Arrow Limited, Int'l App'l No. PCT/US2011/044233, filed Jul. 15, 2011. (ws:328) [Exhibit 62].
PCT International Search Report Dec. 6, 2011, for Pacific Arrow Limited, Int'l App'l No. PCT/US2011/044233, filed Jul. 15, 2011. (ws:329) [Exhibit 63].
U.S. Office Action, Dec. 28, 2011, for Chan et al., U.S. Appl. No. 12/714,598, filed Mar. 1, 2010. (ws:343) [Exhibit 64].
U.S. Notice of Allowance, Jan. 30, 2012, for Chan et al., U.S. Appl. No. 11/683,198, filed Mar. 7, 2007. (ws:345) [Exhibit 65].
U.S. Office Action, Mar. 20, 2012, for Chan et al., U.S. Appl. No. 12/344,682, filed Dec. 29, 2008. (ws:346) [Exhibit 66].
U.S. Office Action, Apr. 17, 2012, for Chan et al., U.S. Appl. No. 12/392,795, filed Feb. 25, 2009. (ws:347) [Exhibit 67].
Notice of Allowability for Chan et al., U.S. Appl. No. 12/392,795, filed Feb. 25, 2009, Dated Aug. 15, 2012. (ws:364) [Exhibit 68].
U.S. Office Action, Oct. 15, 2012, for Chan et al., U.S. Appl. No. 13/259,480, filed Sep. 23, 2011. (ws:371) [Exhibit 69].
U.S. Office Action, Mar. 21, 2013, for Chan et al., U.S. Appl. No. 12/856,322, filed Aug. 13, 2010. (ws:375) [Exhibit 70].
U.S. Office Action, Feb. 1, 2013, for Chan et al., U.S. Appl. No. 13/259,480, filed Sep. 23, 2011. (ws:378) [Exhibit 71].
U.S. Office Action, Apr. 11, 2013, for Chan et al., U.S. Appl. No. 11/683,198, filed Mar. 7, 2007. (ws:379) [Exhibit 72].
U.S. Office Action, Jun. 6, 2013, for Chan et al., U.S. Appl. No. 13/259,480, filed Sep. 23, 2011. (ws:385) [Exhibit 73].
PCT International Preliminary Report on Patentability, Jun. 25, 2013, for Pacific Arrow Limited, Int'l App'l No. PCT/US2011/044233, filed Jul. 15, 2011. (ws:387) [Exhibit 74].
PCT Notification Concerning Transmittal of International Preliminary Report on Patentability, Jul. 4, 2013, for Pacific Arrow Limited, Int'l App'l No. PCT/US2011/044233, filed Jul. 15, 2011. (ws:388) [Exhibit 75].
Notice of Allowability for Chan et al., U.S. Appl. No. 14/020,099, filed Sep. 6, 2013, Dated Mar. 3, 2014. (ws:391) [Exhibit 76].
U.S. Office Action, Nov. 21, 2013, for Chan et al., U.S. Appl. No. 13/718,575, filed Dec. 18, 2012. (ws:392) [Exhibit 77].
U.S. Office Action, Dec. 21, 2011, for Chan et al., U.S. Appl. No. 12/541,713, filed Aug. 14, 2009. (ws:332) [Exhibit 78].
U.S. Office Action, Jun. 26, 2012, for Chan et al., U.S. Appl. No. 12/541,713, filed Aug. 14, 2009. (ws:359) [Exhibit 79].
Supplementary European Search Report issued on Oct. 13, 2009 for Pacific Arrow Limited et al., European Patent Application No. 04815530.3, PCT/US2004043465(ws:249) [Exhibit 80].
Supplementary European Search Report issued on Oct. 13, 2009 for Pacific Arrow Limited et al., European Patent Application No. 04809909.7, PCT/US2004033359 (ws:250) [Exhibit 81].
Supplementary European Search Report issued on Oct. 22, 2009 for Mak et al., European Patent Application No. 05810263.3, PCT/US2005031900 (ws:254) [Exhibit 82].
European Office Communication for Pacific Arrow Limited, et al., European App'l No. EP 06751723.5-2123, Dated Jan. 15, 2010. (ws:263) [Exhibit 83].
European Office Communication for Mak May Sung, et al., European App'l No. EP 0581026.3-2123, Dated Dec. 29, 2009. (ws:264) [Exhibit 84].
European Office Communication for Pacific Arrow Limited, et al., European App'l No. EP 04809909.7-2123, Dated Apr. 19, 2010. (ws:267) [Exhibit 85].
European Office Communication for Pacific Arrow Limited, et al., European App'l No. EP 04815530.3-2123, Dated Apr. 19, 2010. (ws:268) [Exhibit 86].
European Office Communication for Mak May Sung, et al., European Appl'l No. EP 05810263.3-2123, Dated Apr. 19, 2010. (ws:269) [Exhibit 87].
European Office Communication for Pacific Arrow Limited, et al., European App'l No. EP 07841638.5-2123, Dated Apr. 19, 201. (ws:270) [Exhibit 88].
European Office Communication, Feb. 13, 2012, for Pacific Arrow Limited, European App'l No. EP 07841638.5-2123, filed Mar. 27, 2009. (ws:334) [Exhibit 89].
European Office Communication, Feb. 13, 2012 for Pacific Arrow Limited, European App'l No. EP 05810263.3-2123, filed Mar. 30, 2007. (ws:335) [Exhibit 90].
European Office Communication, Feb. 13, 2012, for Pacific Arrow Limited, European App'l No. EP 04815530.3-2123, filed Jul. 19, 2006. (ws:336) [Exhibit 91].
European Office Communication, Mar. 3, 2012 for Pacific Arrow Limited, European App'l No. EP 04809909.7-2123, filed Mar. 27, 2006. (ws:342) [Exhibit 92].
European Office Communication, Apr. 26, 2012 for Pacific Arrow Limited, European App'l No. EP 09721583.4-2123, filed Sep. 7, 2010. (ws:351) [Exhibit 93].
European Office Communication, May 13, 2013 for Pacific Arrow Limited, European App'l No. EP 10800596.8-1462, filed Mar. 30, 2012. (ws:382) [Exhibit 94].
European Office Communication, Jun. 26, 2013, for Pacific Arrow Limited, European App'l No. EP 04815530.3-1464, filed Jul. 19, 2006. (ws:386) [Exhibit 95].
European Office Communication, May 7, 2014, for Pacific Arrow Limited, European App'l No. EP 04809909.7-1464, filed Mar. 27, 2006. (ws:393) [Exhibit 96].
European Office Communication, Jun. 20, 2014, for Pacific Arrow Limited, European App'l No. EP 11807584.5-1451, filed Jul. 15, 2011. (ws:402) [Exhibit 97].
Australian Office Action for Australian Patent No. 2004281707, Feb. 19, 2010, Pacific Arrow Limited. (ws:262) [Exhibit 98].
Australian Office Action, Mar. 18, 2011 for Pacific Arrow Limited, Australian Patent Application No. 2004281707, filed Oct. 8, 2004. (ws:300) [Exhibit 99].
Notice of Acceptance for Pacific Arrow Limited, Australian Patent App'l No. 2004281707, filed Mar. 23, 2006, Dated May 26, 2011. [Exhibit 100] (ws:305).
Australian Office Action, Feb. 6, 2012 for Pacific Arrow Limited, Australian App'l No. 2009208069, filed Aug. 7, 2009. (ws:337) [Exhibit 101].
Australian Office Action, Feb. 6, 2012 for Pacific Arrow Limited, Australian App'l No. 2005282437, filed Mar. 19, 2007. (ws:338) [Exhibit 102].
Australian Office Action, Feb. 6, 2012 for Pacific Arrow Limited, Australian App'l No. 2009200988, filed Mar. 10, 2009. (ws:341) [Exhibit 103].
Australian Office Action, Jun. 21, 2012 for Pacific Arrow Limited, Australian App'l No. 2008244648, filed Aug. 21, 2009. (ws:360) [Exhibit 104].
Australian Office Action, Apr. 16, 2013 for Pacific Arrow Limited, Australian App'l No. 2009226063, filed Sep. 6, 2010. (ws:389) [Exhibit 105].

(56) References Cited

OTHER PUBLICATIONS

Australian Office Action, Jan. 28, 2015 for Pacific Arrow Limited, Australian App'l No. 2011278983, filed Jul. 15, 2011. (ws:399) [Exhibit 106].
Australian Office Action, Feb. 27, 2015 for Pacific Arrow Limited, Australian App'l No. 2012284244, filed Jul. 13, 2012. (ws:400) [Exhibit 107].
Australian Office Action, Mar. 19, 2015 for Pacific Arrow Limited, Australian App'l No. 2013200614, filed Feb. 5, 2013. (ws:401) [Exhibit 108].
Zealand Office Action, Aug. 12, 2009, New Zealand Application No. 546138, filed Mar. 22, 2007. (ws:247) [Exhibit 109].
New Zealand Office Action, Sep. 22, 2009, New Zealand Application No. 546138, filed Mar. 27, 2006. (ws:248) [Exhibit 110].
New Zealand Office Action, Mar. 7, 2011 for Pacific Arrow Limited, New Zealand App'l No. 587973, filed Sep. 14, 2010. (ws:302) [Exhibit 111].
New Zealand Office Action, Apr. 12, 2011 for Pacific Arrow Limited, New Zealand App'l No. 554037, filed Mar. 19, 2007. (ws:306) [Exhibit 112].
New Zealand Office Action, Sep. 24, 2010, for Pacific Arrow Limited, New Zealand App'l No. 579194, filed Aug. 21, 2009. (ws:331) [Exhibit 113].
New Zealand Office Action, Jan. 11, 2012, for Pacific Arrow Limited, New Zealand App'l No. 579194, filed Aug. 21, 2009. (ws:340) [Exhibit 114].
New Zealand Office Action, Mar. 26, 2012, for Pacific Arrow Limited, New Zealand App'l No. 598934, filed Mar. 21, 2012. (ws:350) [Exhibit 115].
Japan Office Action, Jan. 14, 2011, for Pacific Arrow Limited, Japan App'l No. 2006-534419, filed Mar. 22, 2006. (ws:288) [Exhibit 116].
Japan Office Action, Feb. 2, 2011, for Pacific Arrow Limited, Japan app'l No. 2006-534419, filed Mar. 22, 2006. (ws:298) [Exhibit 117].
Japan Office Action, Mar. 18, 2011, for Pacific Arrow Limited, Japan app'l No. 2006-547422, filed Jun. 16, 2006. (ws:299) [Exhibit 118].
Japan Office Action, Jun. 3, 2011 for Pacific Arrow Limited, Japan App'l No. 2006-534419, filed Mar. 22, 2006. (ws:307) [Exhibit 119].
Japanese Notice of Allowance, Nov. 15, 2011, for Pacific Arrow Limited, Japanese app'l No. 2006-547422, filed Jun. 16, 2006. (ws:322) [Exhibit 120].
Japanese Office Action, Nov. 21, 2011, for Pacific Arrow Limited, Japanese app'l No. 2007-530484, filed Mar. 2, 2007. (w/English translation) (ws:326) [Exhibit 121].
Japanese Office Action, May 8, 2012, for Pacific Arrow Limited, Japanese app'l No. 2007-530484, filed Mar. 2, 2007. (w/English translation) (ws:358) [Exhibit 122].
Korean Office Action, Jun. 3, 2011 for Pacific Arrow Korean App'l No. 10-2006-7008896, filed May 8, 2006. (ws:301) [Exhibit 123].
Korean Office Action, Jun. 22, 2012 for Pacific Arrow Limited, Korean App'l No. 10-2007-7007902, filed Apr. 6, 2007. (ws:362) [Exhibit 124].
Canadian Notice of Allowance, Oct. 5, 2011, for Pacific Arrow Limited et al, Canadian App'l No. 2541425, filed Oct. 8, 2004. (ws:319) [Exhibit 125].
Canadian Office Action, Jan. 31, 2012, for Pacific Limited, Canadian Application No. 2,579,231, filed Mar. 6, 2007. (ws:333) [Exhibit 126].
Canadian Office Action, Feb. 26, 2013, for Pacific Arrow Limited, Canadian App'l No. 2,579,231, filed Mar. 6, 2007. (ws:381) [Exhibit 127].
Arda, et al. "Saniculoside N from Sanicula europaea L." Journal of Natural Products (1997), 60(11), 1170-1173. (ws:1) [Exhibit 128].
Barre, et al. "A bioactive triterpene from Lantana camara." Phytochemistry (1997), 45(2), 321-324. (ws:3) [Exhibit 129].
Chen, et al. Studies on the constituents of Xanthoceras sorbifolia Bunge. II. Major sapogenol and a prosapogenin from the fruits of Xanthoceras sorbifolia Bunge. Chemical & pharmaceutical bulletin (Sep. 1984), 32(9), 3378-83. (ws:9) [Exhibit 130].
Chen, et al. "Studies on the constituents of Xanthoceras sorbifolia Bunge. III. Minor prosapogenins from the fruits of Xanthoceras sorbifolia Bunge." Chemical & Pharmaceutical Bulletin (1985), 33(1), 127-34. (ws:10) [Exhibit 131].
Chen, et al. "Studies on the constituents of Xanthoceras sorbifolia Bunge. IV. Structures of the minor prosapogenins." Chemical & Pharmaceutical Bulletin (1985), 33(3), 1043-8. (ws:11) [Exhibit 132].
Chen, et al. "Studies on the constituents of Xanthoceras sorbifolia Bunge. V. Major saponins from the fruits of Xanthoceras sorbifolia Bunge." Chemical & Pharmaceutical Bulletin (1985), 33(4), 1387-94. (ws:12) [Exhibit 133].
Koike, et al. "New triterpenoid saponins from Maesa japonica." Journal of Natural Products (1999), 62(2), 228-232. (ws:27) [Exhibit 134].
Li, et al. "New guaianolides and xanthine oxidase inhibitory flavonols from Ajania fruticulosa." Journal of Natural Products (1999), 62(7), 1053-1055. (ws:34) [Exhibit 135].
Meng, et al. "Antifungal highly oxygenated guaianolides and other constituents from Ajania fruticulosa." Phytochemistry (2001), 58(7), 1141-1145. (ws:40) [Exhibit 136].
Sakurai, et al. "Assamicin I and II, novel triterpenoid saponins with insulin-like activity from Aesculus assamica Griff" Bioorganic & Medicinal Chemistry Letters (2002), 807-810. (ws:46) [Exhibit 137].
Sindambiwe, et al. "Triterpenoid saponins from Maesa lanceolata." Phytochemistry (1996), 41(1), 269-77. (ws:50) [Exhibit 138].
Tuntiwachwuttikul, et al. "A triterpenoid saponin from Maesa ramentacea." Phytochemistry (1997), 44(3), 491-495. (ws:54) [Exhibit 139].
Voutquenne, et al. Triterpenoid saponins and acylated prosapogenins from Harpullia austro-caledonica. Phytochemistry (2002), 59(8), 825-832. (ws:55) [Exhibit 140].
Waechter, et al. "Antitubercular Activity of Triterpenoids from Lippia turbinata." Journal of Natural Products (2001), 64(1), 37-41. (ws:57) [Exhibit 141].
Zhao, et al. "Four New triterpene saponins from the seeds of Aesculus chinensis." Journal of Asian Natural products Research (2003), 5(3), 197-203. (ws:65) [Exhibit 142].
Zhao, et al. "Three new triterpene saponins from the seeds of Aesculus chinensis." Chemical & Pharmaceutical Bulletin (2001), 49(5), 626-628. (ws:66) [Exhibit 143].
Aper, et al. "New acylated triterpenoid saponins from lanceolata." Phytochemistry 52 (1999) 1121-1131. (ws:68) [Exhibit 144].
D'Aoquarica, et al. "Isolation and structure elucidation of four new triterpenoid estersaponins from fruits of Pittosporum tobira AIT." Tetrahedron 58 (2002) 10127-10136. (ws:69) [Exhibit 145].
Jiang. et al. "Six Triterpenoid Saponins from Maesa Laxiflora." J. Nat. Prod. 1999. 62, 873-876. (ws:70) [Exhibit 146].
Lu, et al. "Triterpenoid saponins from the roots of tea plants (Camellia sinensis var. assamica)." Phytochemistry 53 (2000) 941-946 (ws:71) [Exhibit 147].
Seo, et al. "A New Triterpene Saponin from Pittosporum viridlflorum from the Madagascar Rainforest." J. Nat. Prod. 2002, 65, 65-68 (ws:72) [Exhibit 148].
Yang, et al. "Anti-HIV-1 Protease Triterpenoid Saponins from the Seeds of Aesculus chinensis." J. Nat. Prod. 1999, 62, 1510-1513. (ws:73) [Exhibit 149].
Voutquenne, et al. "Structure-Activity Relationships of Haemolytic Saponins" Pharmaceutical Biology (2002), vol. 40, No. 4, pp. 253-262 (ws:108) [Exhibit 150].
Sirtori, C., "Aescin: Pharmacology, Pharmacokinetic Profile" Pharmacological Research (2001) vol. 44, No. 3, pp. 183-193. (ws:109) [Exhibit 151].
Oda, K. et al., "Adjuvant and Haemolytic Activities of 47 Saponins Derived from Medicinal and Food Plants" Biol. Chem. (2000) vol. 381, pp. 67-74. (ws:110) [Exhibit 152].
Chan, Pui-Kwong, 2007, "Acylation with diangeloyl groups at C21-22 positions in triterpenoid saponins is essential for cytotoxcity towards tumor cells", Biochemical Pharmacology 73(2007): 341-350. (ws:144) [Exhibit 153].

(56) References Cited

OTHER PUBLICATIONS

Lavaud, et al., 1992, "Saponins from Steganotaenia Araliacea", Phycochemistry, 31(9):3177-3181. (ws:145) [Exhibit 154].
Zhang, et al., 2007, "Cytotoxic triterpenoid saponins from the fruits of Aesculus pavia L", Phytochemistry 68(2007): 2075-2086. (ws:146) [Exhibit 155].
Li, et al., 2005, "Two New Triterpenes from the Husks of Xanthoceras Sorbifolia", Planta Medica, vol. 71:1068-1070. (ws:161) [Exhibit 156].
The Merck Manual of Diagnosis and Therapy, 17th Edition, Published by Merck Research Lanoratories, pp. 397-398, 948-949, 1916, and 1979-1981. (ws:162) [Exhibit 157].
The Oxford Textbook of Oncology, 1995, published by Oxford University Press, pp. 447-453. (ws:163) [Exhibit 158].
Voutquenne, et al., 2005, "Haemolytic Acylated Triterpenoid saponins from Harpullia austro-caledonica". Phytochemistry, vol. 66: 825-826. (ws:164) [Exhibit 159].
Ma, et al, 2008, "Cytotoxic Triterpenoid Saponins Acylated with Monoterpenic Acid from Pithecellobium lucidum", Journal of Natural Products, vol. 71(1): 41-46. (ws:165) [Exhibit 160].
Ushijima, et al, 2008, "Triterpene Glycosides from the of Codonopsis lanceolata", Chemical & Pharmaceutical Bulletin, vol. 56(3) 308-314. (ws:166) [Exhibit 161].
Yadava, et al., 2008, "New antibacterial triterpenoid saponin from Lactuca scariola", Fitoterapia, vol. 1:1-5 (ws:167) [Exhibit 162].
Wang, et al., 2008, "Bioactive Triterpene Saponins from the Roots of Phytolacca Americana", Journal of Natural Products, vol. 71(1): 35-40. (ws:168) [Exhibit 163].
Chang, et al, 2007, "Biologically Active Triterpenoid Saponins from Ardisia japonica", Journal of Natural Products, vol. 70(2): 179-187. (ws:169) [Exhibit 164].
Akihisa et al, 2006, "Cancer Chemopreventive Effects and Cytotoxic Activities of the Triterpene Acids from the Resin of Boswellia carteri", Biological & Pharmaceutical Bulletin, 29(9):1976-1979. (ws:170) [Exhibit 165].
Liang, et al., 2006, "Triterpenoid Saponins from Lysimachia davurica", Chemical & Pharmaceutical Bulletin, (10):1380-1383. (ws:171) [Exhibit 166].
Fujioka, et al., 2006, "Antiproliferative Constituents from Umbelliferae Plants. New Triterpenoid Glycosides from the Fruits of Bupleurum rotundifolium", Chemical & Pharmaceutical Bulletin, vol. 54 (12):1694-1704. (ws:172) [Exhibit 167].
Rabi, et al., 2007, "Novel triterpenoid 25-hydroxy-3-oxoolean-12-en-28-oic acid induces growth arrest and apoptosis in breast cancer cells", Breast Cancer Research & Treatment, vol. 101:27-36. (ws:173) [Exhibit 168].
Sporn, et al., 2007, "Platforms and Networks in Triterpenoid Pharmacology", Drug Development Research, vol. 68:174-182 (2007). (ws:174) [Exhibit 169].
Puiffe, et al., 2007, "Characterization of Ovarian Cancer Ascites on Cell Invasion, Proliferation, Spheroid Formation, and Gene Expression in an In Vitro Model of Epithelial Ovarian Cancer" Neoplasia, vol. 9(10):820-829. (ws:175) [Exhibit 170].
Ricciardelli, et al., 2006, "Extracellular Matrix of Ovarian Tumors", Seminars in Reproductive Medicine, vol. 24(4): 270-282 (ws:176) [Exhibit 171].
Bang, et al., 2007, "Facile Synthesis of Trisaccharide Moiety Corresponding to Antitumor Activity in Triterpenoid Saponins Isolated from Pullsatilla Roots", Chemical & Pharmaceutical Bulletin, vol. 55(12) : 1734-1739. (ws:177) [Exhibit 172].
Talmadge, James E., 2008, "Follistatin as an Inhibitor of Experimental Metastasis", Clinical Cancer Research, vol. 14(3) 624-626. (ws:178) [Exhibit 173].
Wei, et al., 2004, "Anti-inflammatory Triterpenoid Saponins from the Seeds of Aesculus chinensis", Chemical & Pharmaceutical Bulletin, vol. 52(10): 1246-1248. (ws:179) [Exhibit 174].
Konoshima, et al. "Antitumor Agents, 82. Cytotoxic Sapogenols from Aesculus Hippocastanum", Journal of Natural Products vol. 49, No. 4, pp. 650-656, Jul.-Aug. 1986. (ws:221) [Exhibit 175].

Maes, et al. "In vitro and in vivo activities of triterpenoid saponin extract (px-6518) from the plant Maesa balansae against visceral leishmania species." Antimicrobial agents and chemotherapy, Jan. 2004, p. 130-136. (ws:241) [Exhibit 176].
Murakami, et al. "New hypoglycemic constituents in "gymnemic acid" from gymnema sylvestre." Chem. Pharm. Bull. 44(2) 469-471 (1996). (ws:242) [Exhibit 177].
Na, et al. "Protein tyroshine phosphatase 1B inhibitory activity of triterpenes isolated from astilbe koreana." Bioorg Med Chem Lett. Jun. 15, 2006;16 (120: 3273-6. (ws:243) [Exhibit 178].
Zhou, et al. "The first naturally occurring tie2 kinase inhibitor." Org Lett. Dec. 13, 2001;3(25) : 4047-9. (ws:244) [Exhibit 179].
Apers Sandra et al., "Antiviral, haemolytic and molluscicidal activities of triterpenoid saponins from Maesa lanceolata: Establishment of structure-activity relationship", Planta Medica, vol. 67, No. 6, Aug. 2001, pp. 528-532. (ws:251) [Exhibit 180].
Ahmad V U et al., "The Sapogenins from Dodonaea-Viscosa", Fitoterapia, vol. 58, No. 5, 1987. pp. 361-362. (ws:252) [Exhibit 181].
Dizes C et al., "harpuloside a triterpenoid saponin from harpullia ramiflora", Phytochemistry, Pergamon Press, GB, vol. 48, No. 7, Aug. 1, 1998, pp. 1229-1232. (ws:253) [Exhibit 182].
Yang et al. "The Influence of aquaporin—1 and microvessel density on ovarian carcinogenesis and ascites formation", International Journal of Gynecological Cancer, vol. 16, No. S1, Feb. 1, 2006, pp. 400-405. (ws:344) [Exhibit 183].
Germonprez N. et al. "In vitro and in vivo anti-leishmanial activity of triterpenoid saponins isolated from Maesa balansae and some chemical derivatives", Journal of Medicinal Chemistry, vol. 48 No. 1 (Jan. 13, 2005), p. 32-37. (ws:354) [Exhibit 184].
Dan Peer, et al. "Nanocarriers as an emerging platform for cancer therapy." Nature Publishing Group (2007), 751-760. (ws:368) [Exhibit 185].
Mahato et al. Tetrahedron 1991 (47) 5215-5230. (ws:372) [Exhibit 186].
Sheng-Xiang et al. Phytochemistry (1993), 34(5), 1385-1387. (ws:373) [Exhibit 187].
Ohtsuki et al. "Acylated triterpenoid saponins from Schima noronhae and their cell growth inhibitory activity", Journal of Natural Products, vol. 71, No. 5, Mar. 20, 2008, pp. 918-921, XP002694762 (ws:383) [Exhibit 188].
Sharma et al. "Lanthadenes and their esters as potential antitumor agents", Journal of Natural Products, vol. 71, No. 7, Jun. 14, 2008, pp. 1222-1227, XP002694763 (ws:384) [Exhibit 189].
Bao-Ning Su et al., "Isolation and absolute stereochemistry of coussaric acid, a new bioactive triterpenoid from the stems of Cousserea brevicaulis", Phytochemistry 64 92003) 293-302. (ws:397) [Exhibit 190].
Wang P. et al., "Cytotoxicity and inhibition of DNA topoisomerase and I of polyhydroxylated triterpenoids and triterpenoid glycosides", Bioorg. Med. Chem. Lett. vol. 20(9) pp. 2790-2796. (ws:403) [xhibit 191].
Josef Wagner et al., "Uber inhaltsstoffe des rosskastaniensamens VI", Tetrahedron letters, vol. 9(41), pp. 4387-4390. (ws:404) [Exhibit 192].
J. Wagner et al., "Acylwanderungen am Protoascigenin Uber inhaltsstoffe des rosskastaniensamens, X", Arch. Pharmaz. 304(11) pp. 804-815. (ws:405) [Exhibit 193].
Itiro Yosioka et al., "Saponin and Sapogeno. IV. Seeds Sapogenols of Aesculus turbinate BLUME. On the configuration of Hydroxyl function in Ring E of Aescigenin, Protoaescigenin, and I soaescigeninin relation to Barringtogenol C and Theasapogenol A", Chem. Pharm. Bull. vol. 19(6), pp. 1200-1213. (ws:406) [Exhibit 194].
G. Wulff et al., "Uber triterpene—XXVI", Terrahedron, vol. 25(2), pp. 415-436. (ws:407) [Exhibit 195].
Irmentraut Low, "Uber Acylwanderungen bei Protoascigeninestern", Hoppe Seyler's Z. Physiol. Chem., vol. 348(1), pp. 839-842. (ws:408) [Exhibit 196].
Chemical Abstracts Service, Columbus, Ohio, US, Germonprez N. et al., "Antileishmanial saponins from Maesa", Tap Chi Hoa Hoc, 41(spec.), 125-130. (ws:355) [Exhibit 197].

* cited by examiner

NATURAL AND SYNTHETIC COMPOUNDS FOR TREATING CANCER AND OTHER DISEASES

This application is a National Stage Application of Int'l App'l No. PCT/US2012/046716, filed Jul. 13, 2012, which is a continuation-in-part of U.S. Ser. No. 13/259,480, filed Sep. 23, 2011, which is a National Stage Application of Int'l App'l No. PCT/US2011/044233, filed Jul. 15, 2011, which is a continuation-in-part of U.S. Ser. No. 12/856,322, filed Aug. 13, 2010, now U.S. Pat. No. 8,586,719, issued Nov. 19, 2013, which is a continuation-in-part of Int'l App'l No. PCT/US2010/0042240, filed Jul. 16, 2010, which claims the benefit of U.S. 61/226,043, filed Jul. 16, 2009.

FIELD OF THE INVENTION

This invention provides methods of synthesizing new compounds for pharmaceutical uses.

BACKGROUND OF THE INVENTION

This invention provides methods of synthesizing new compounds for pharmaceutical uses. This invention provides methods, compounds and compositions for treating cancer, inhibiting cancer invasion, cell invasion, or cancer cell invasion, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers.

SUMMARY OF THE INVENTION

This invention provides methods of synthesizing new compounds for pharmaceutical uses. This invention provides compounds, compositions, and methods for treating cancer, inhibiting cancer invasion, cell invasion, macromolecular invasion, cancer cell invasion, and metastasis. This invention provides a use of compounds, compositions, for manufacturing medicament for treating cancer, inhibiting cancer invasion, macromolecular invasion, virus invasion and metastasis. This invention provides compounds for use as mediator or inhibitor of adhesion protein or angiopoietin, This invention provides compounds for use in a method of modulating attachment or adhesion of cells or angiogenesis, by modulating or inhibiting adhesion protein macromolecules, or angiopoietin, The compounds comprise the structures selected from the formulae in the present application, wherein the compounds are synthesized or isolated, wherein the compounds comprise the saponins, triterpenes, pentacyclic triterpenes, and compounds selected from formulae in the present application, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers. This invention provides compounds for use as a mediator for cell circulating, cell moving cell homing and inflammatory diseases.

DETAILED DESCRIPTION OF THE FIGURES

FIG. 1. HPLC profiles of esterification products of E4A with Tigloyl chloride (A) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature (Top row) and 0 C (bottom row).

Figure 2:
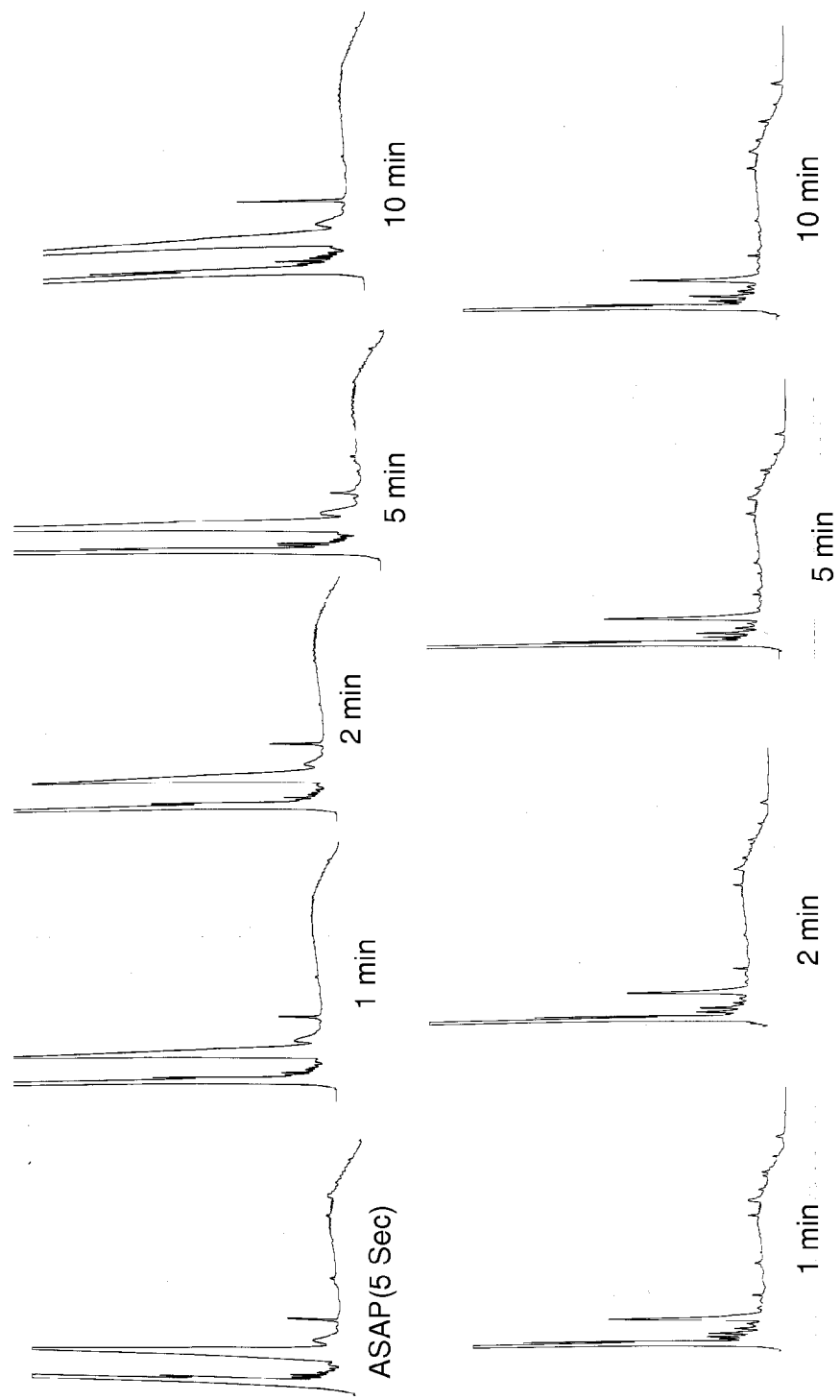

FIG. 2. HPLC profiles of esterification products of E4A with 3,3-dimethylacryloly chloride (B) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature (Top row) and 0 C (bottom row).

Figure 3:
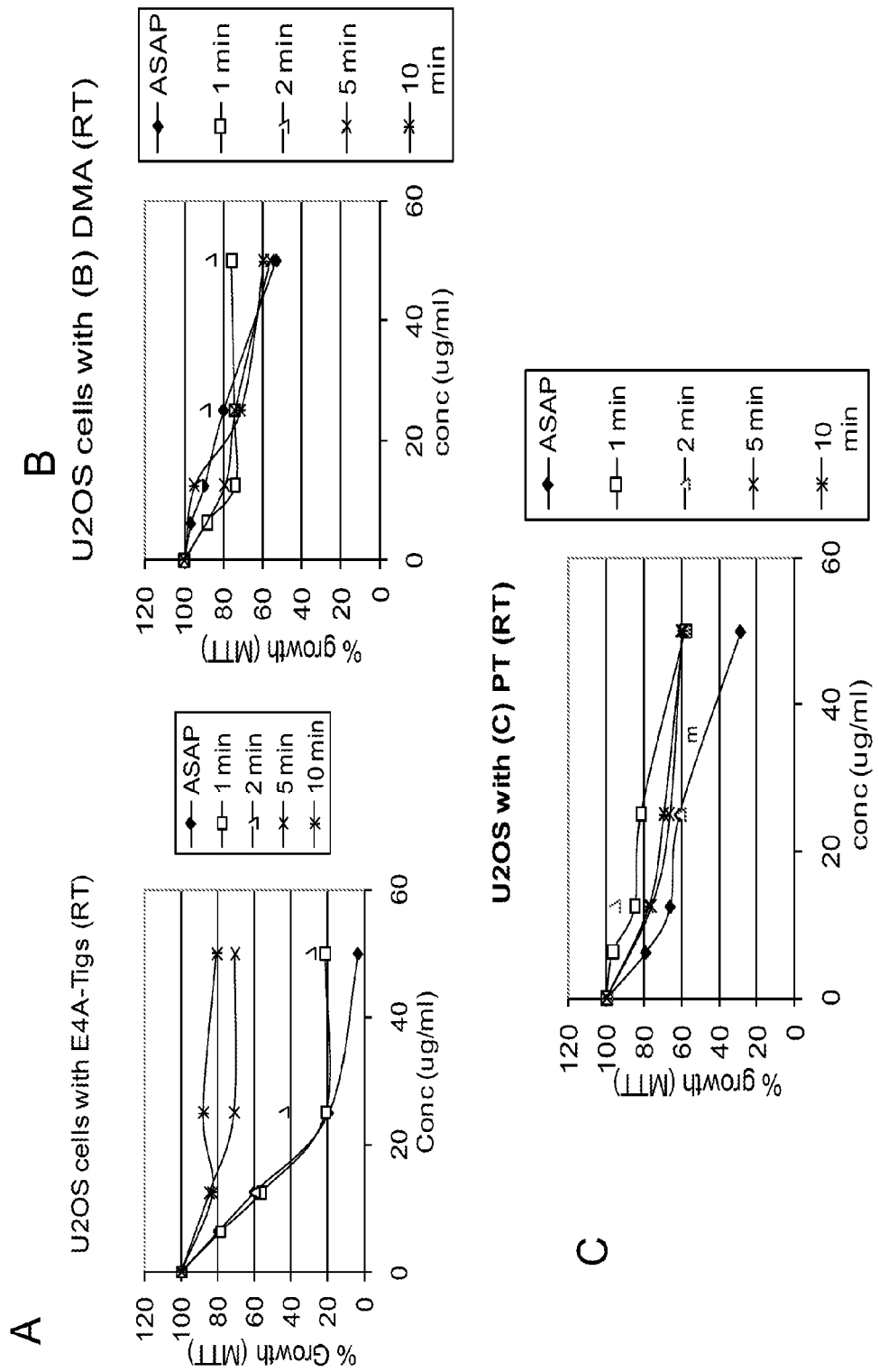

FIG. 3. MTT cytotoxic activity of times study at room temperature, A: E4A-Tigloyl(A); B: E4A-3,3-dimethylacryloly (B); C: E4A-4-pentenoyl(C).

Figure 4:
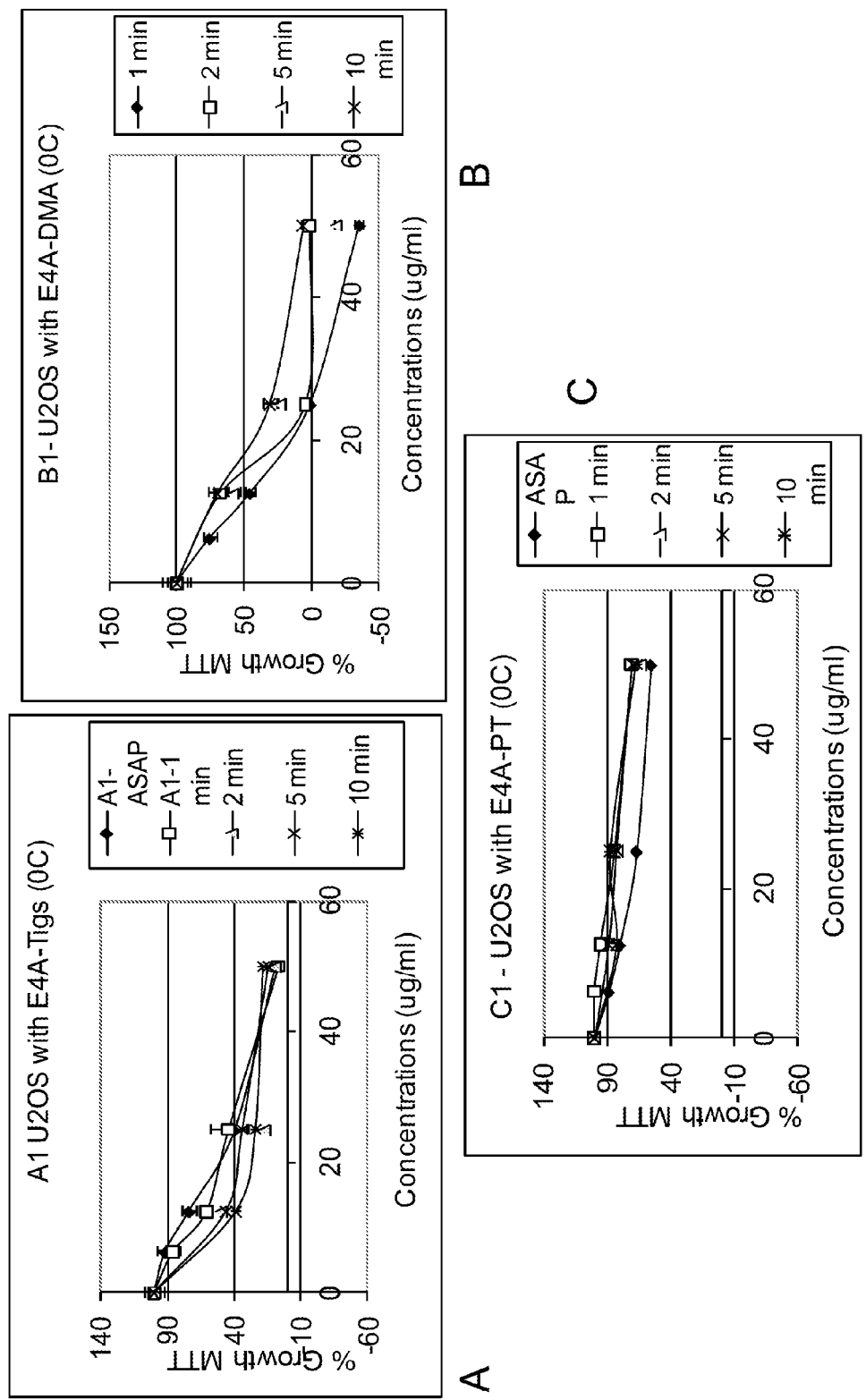

FIG. 4. MTT cytotoxic activity of times study at 0 C, A: E4A-Tigloyl(A); B: E4A-3,3-dimethylacryloly (B); C: E4A-4-pentenoyl(C).

Figure 5:
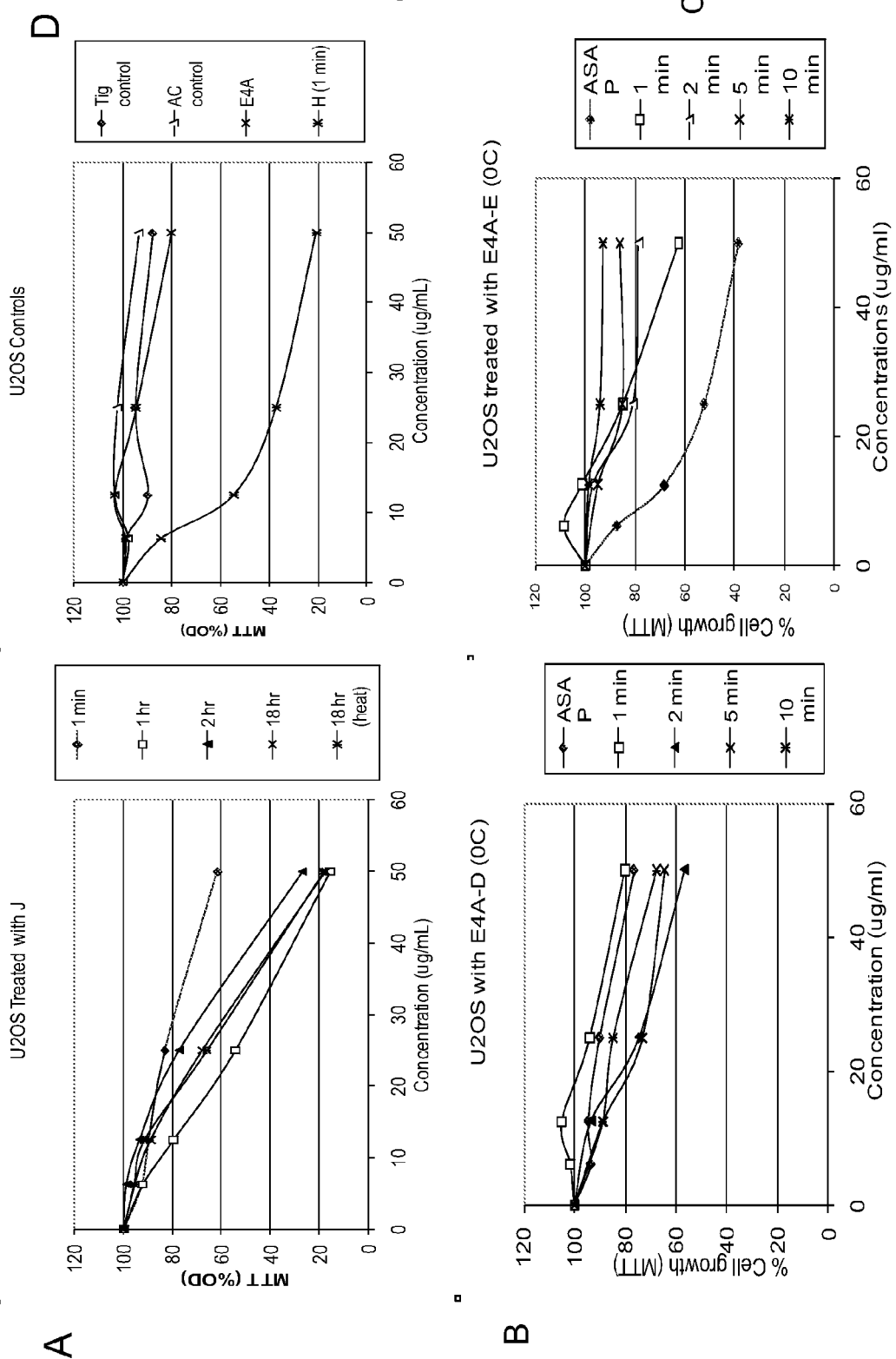

FIG. 5. MTT cytotoxic activity of times study, A: E4A-cinnamoyl(J); B: E4A-hexanoyl(D); C: E4A-2-ethylbutyryl (E); and D, controls: Tig control is tigloyl chloride without E4A; AC control is acetyl chloride without E4A; H is acetyl chloride with E4A reaction 1 min.

Figure 6:
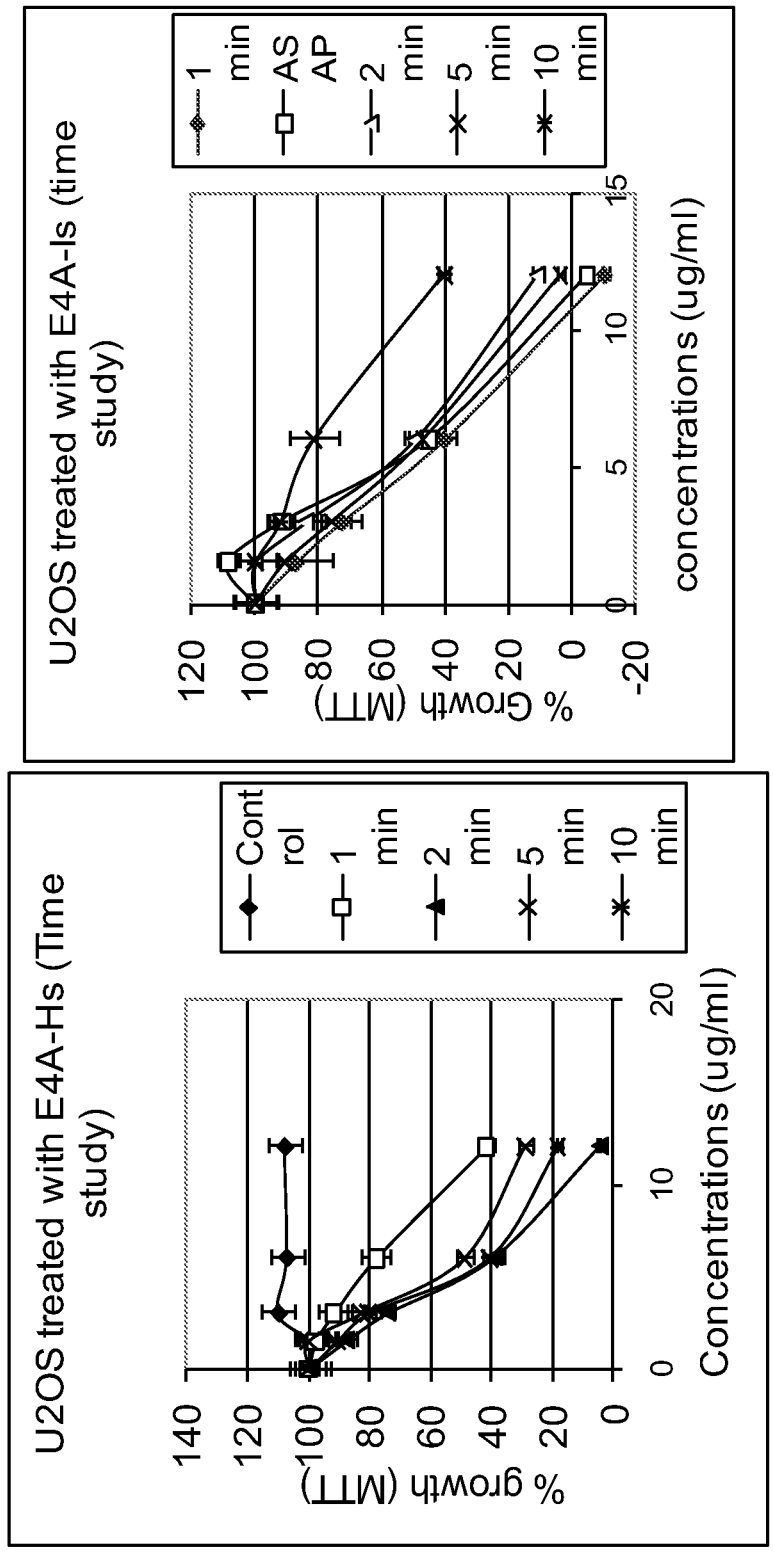

FIG. 6. MTT cytotoxic activity of times study, A: E4A-acetyl(H); B: E4A-crotonoyl(I)

Figure 7:
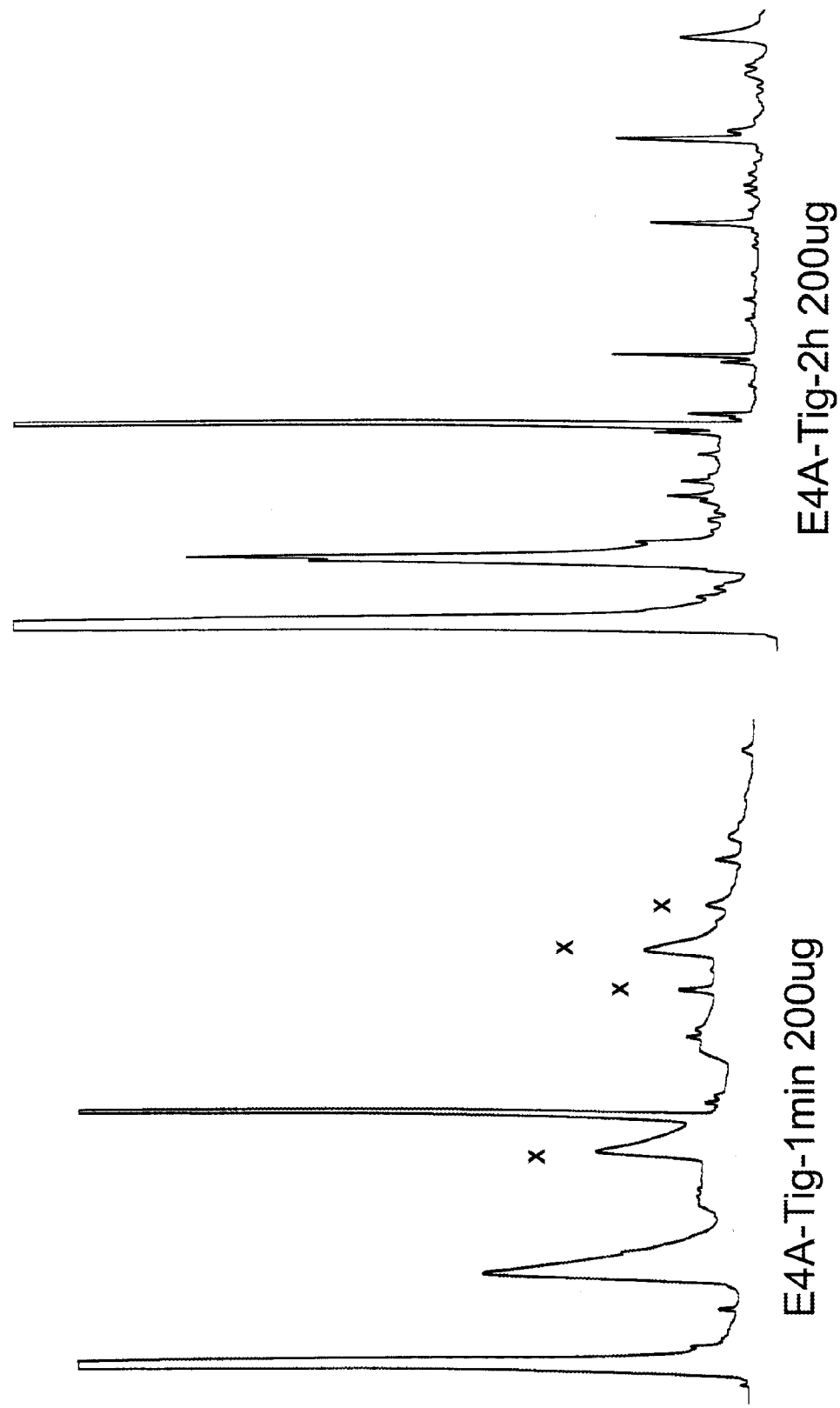

FIG. 7. HPLC profiles of E4A-Tig in 1 min and 2 hours

Figure 8:
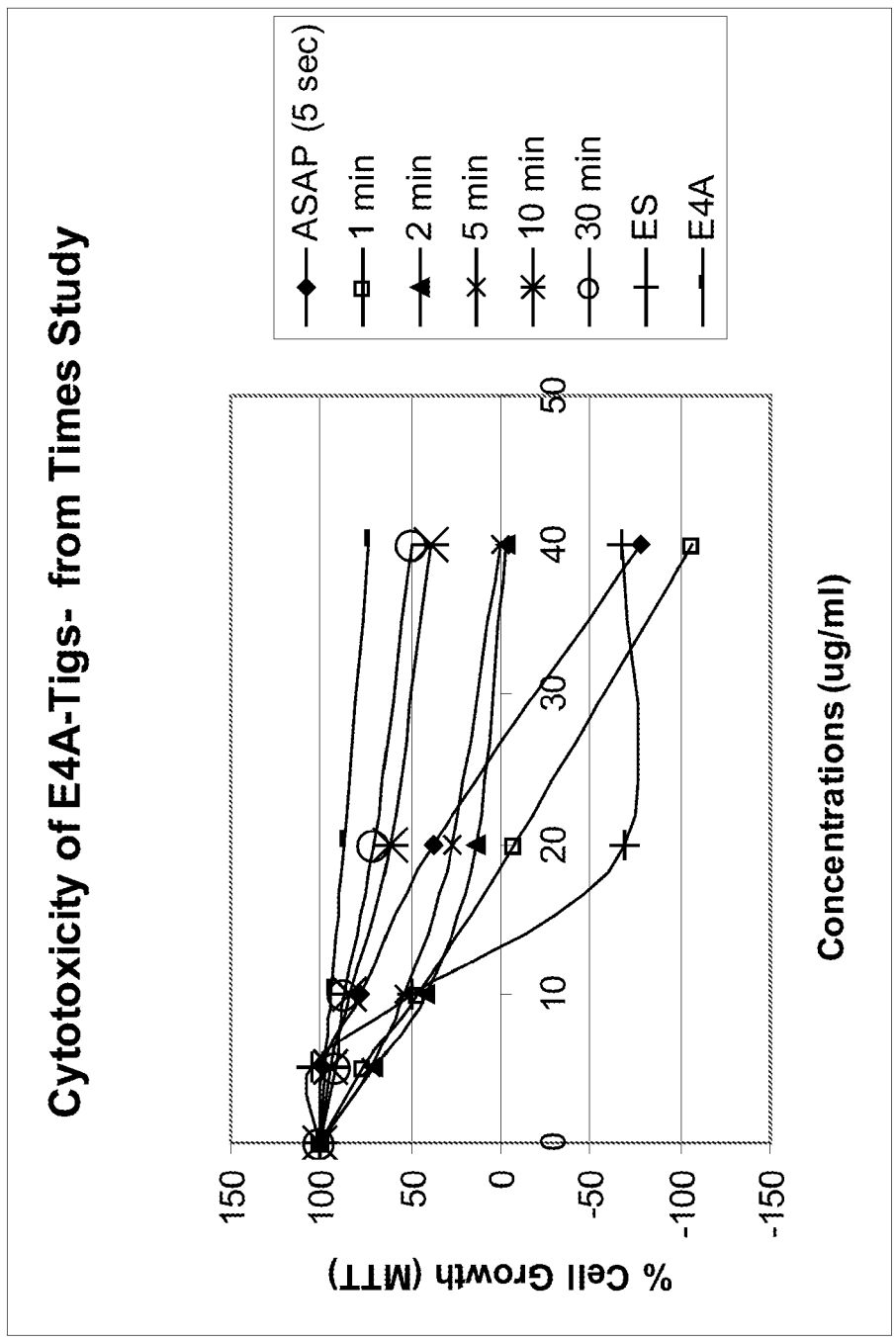

FIG. 8. MTT cytotoxic activity of times study for E4A-Tig. Results: E4A-Tigs from reaction of 5 sec to 1 min are most active. Activity decrease after 1 min of reaction. Minimum to no activity was obtained at 10 minutes or longer.

Figure 9:
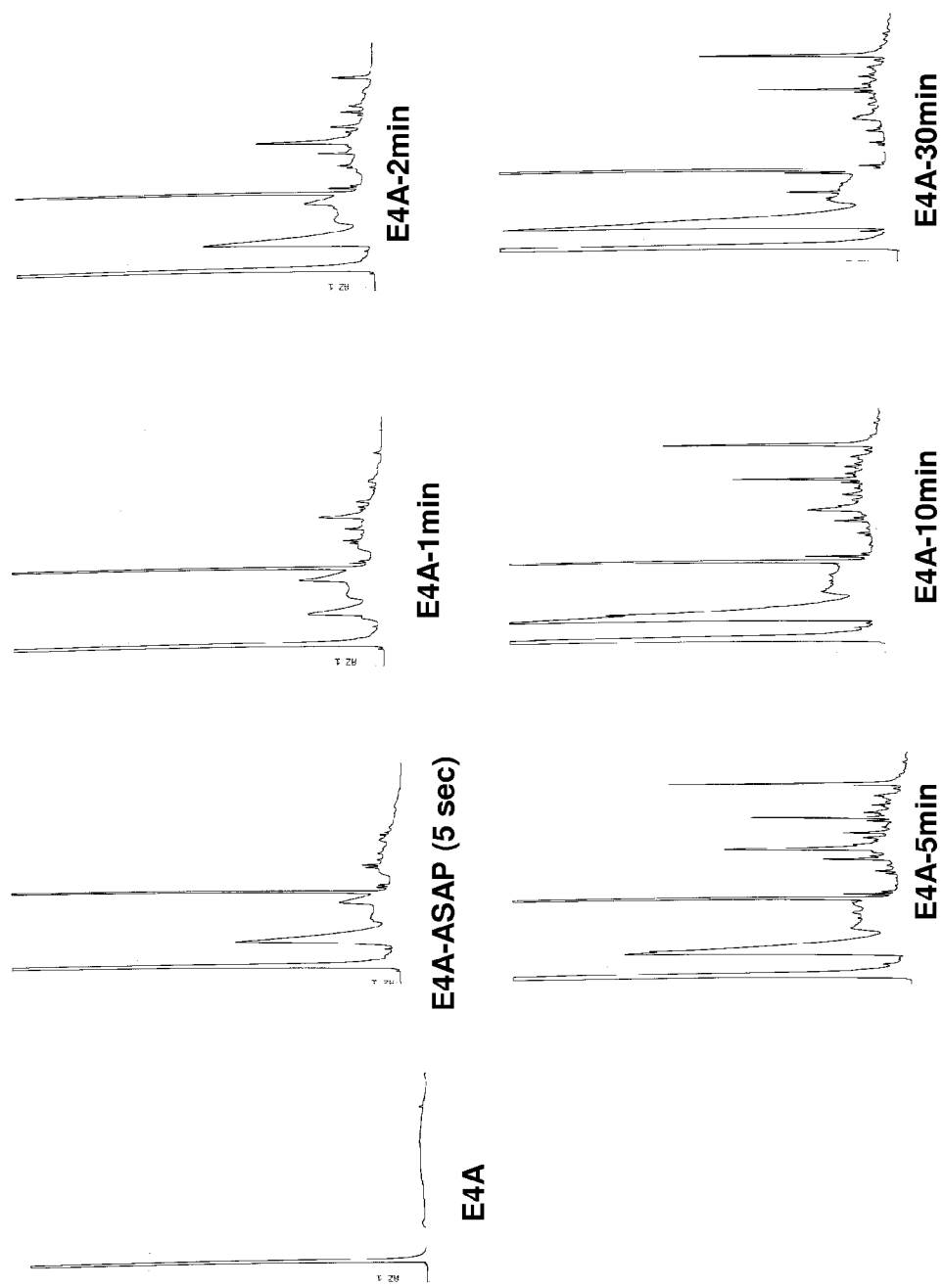

FIG. 9. Results of HPLC profiles of E4A-Tigs: E4A, E4A-ASAP (5 sec), E4A-1 min, E4A-2 min, E4A-5 min, E4A-10 min, E4A-30 min.

Figure 10:
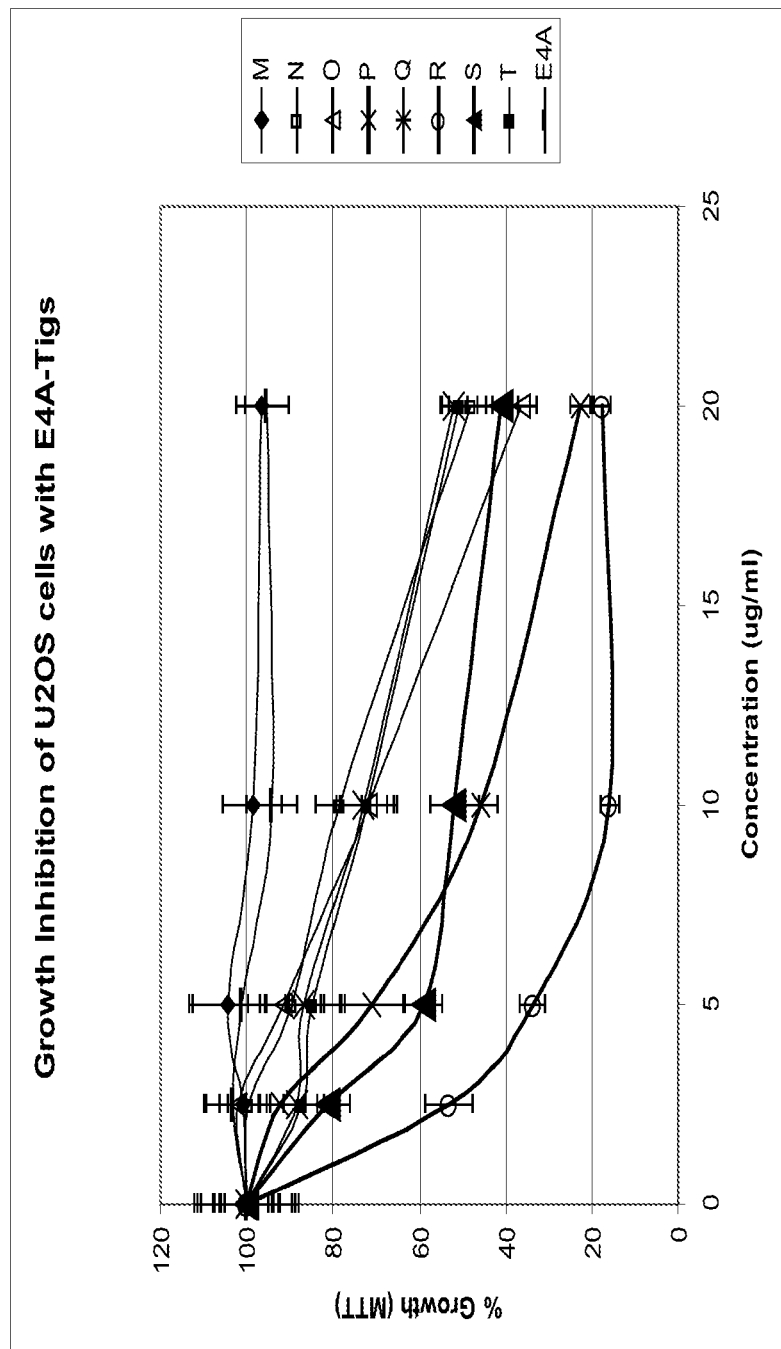

FIG. 10. Results of Activity order: M, N, O, P, Q, R, S, T, E4A; M=E4A has no activity.

Figure 11:
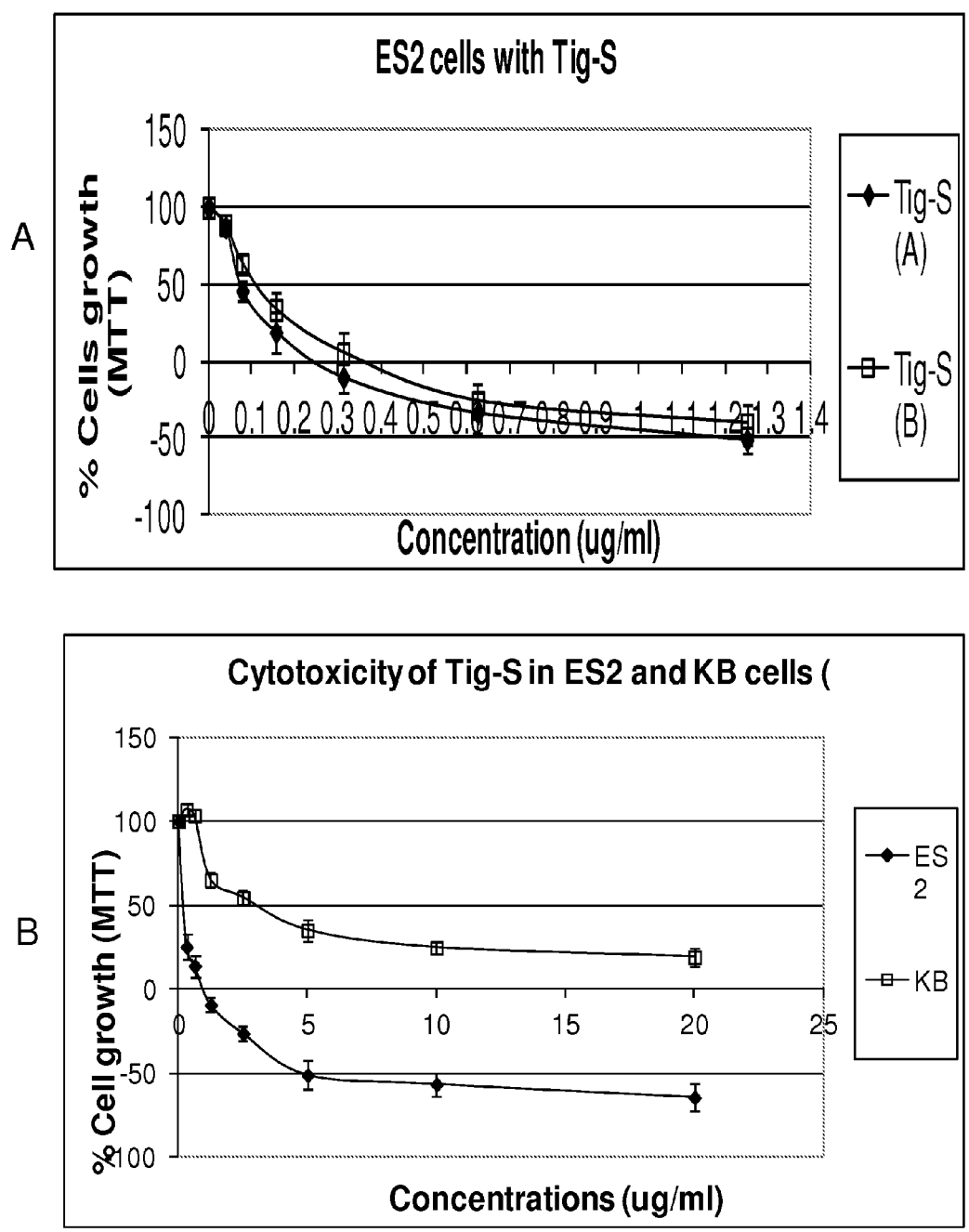
Figure 12:
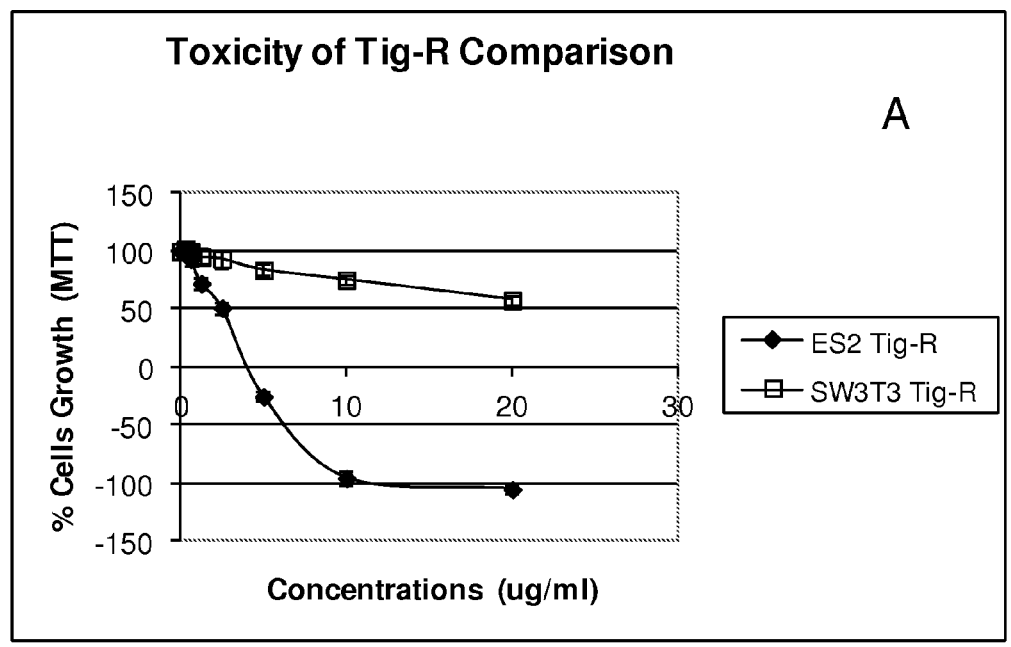
Figure 12:
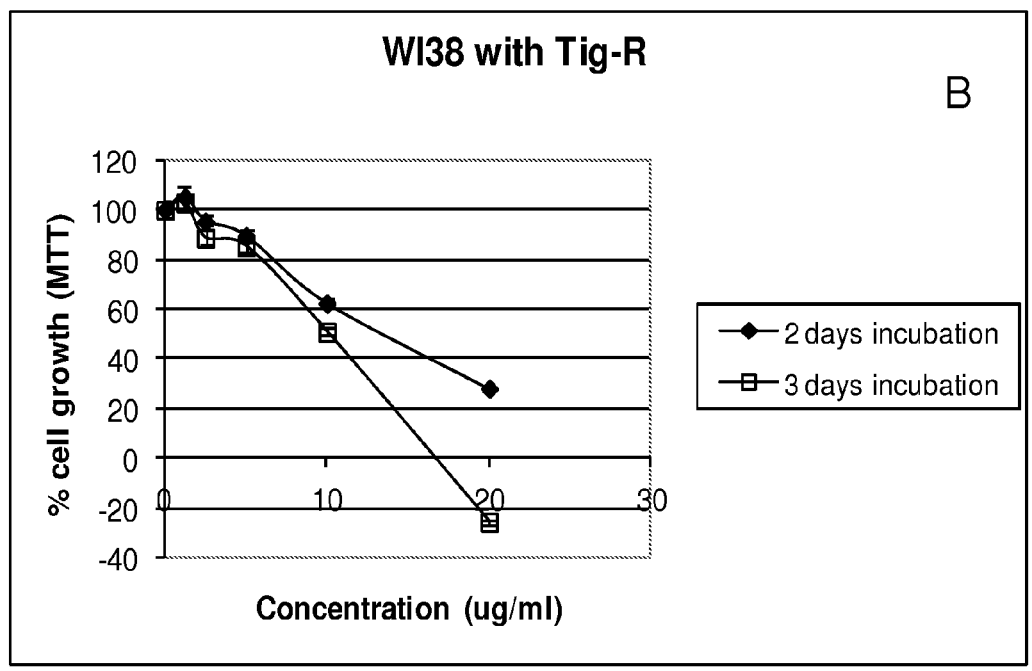

FIG. 11. (A) The IC50 of Tig-S in KB cells is about 4 ug/ml; and the corresponding 1050 in ES2 cells is less than 1 ug/ml; (B) The IC50 of Tig-S in ES2 cells, MTT assay with low doses of Tig-S, the IC50 of Tig-S in ES2 cells is approximately equal to 0.1 ug/ml FIG. 12. (A) Results: Swiss3T3 cells are mouse normal fibroblast which were used in this experiment to compare with ES2 (human ovarian cancer) in Tig-R cytotoxicity determination. The preliminary results indicate that the IC50 of Tig-R in SW3T3 cells is above 20 ug/ml while the corresponding 1050 in ES2 cells is about 2.8 ug/ml. (B) Effect of Tig-R on Normal human lung fibroblast (WI38). Results: The IC50 of Tig-R in normal human fibroblast cells (WI38) is about 10-15 ug/ml. This 1050 value is 3 times higher than those in ES2 (3 ug/ml).

DETAILED DESCRIPTION OF THE INVENTION

This invention provides a method of synthesising new active compounds for pharmaceutical uses. This invention provides an anti adhesion therapy which uses the compound as a mediator or inhibitor of adhesion proteins and angiopoietins. It inhibits excessive adhesion and inhibits cell viral and macromolecular attachment. It modulates angiogenesis. The compounds also use as mediator of cell viral and macromolecular adhesion receptor(s).

This invention provides compounds or a composition comprising the compounds provided in the invention for treating cancers; for inhibiting cancer growth, for inhibiting viruses; for preventing cerebral aging; for improving memory; improving cerebral functions; for curing enuresis, frequent micturition, urinary incontinence; neurodegenerative diseases, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemonhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increase the expression of the genes: ANGPT2, DDIT3, LIF and NFKB1Z, and manufacturing an adjuvant composition and venotonic treatment.

This invention provides compounds, compositions and methods for treating cancer diseases, inhibiting cancer invasion, for inhibiting cancer growth or for inhibiting cancer metastasis, wherein the compounds comprise the structures selected from the formulae of the present application, wherein the compounds can be synthesized or isolated, wherein the compounds comprise the triterpenes, pentacyclic triterpenes, saponins, and compounds selected from formulae in this application, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer; wherein the cells comprise breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphhatic cell, pancreatic cell, stomach cell and thyroid cell.

This invention shows that the presence of group selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl, or sugar moiety substituted with acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl, at a pentacyclic triterpene, triterpene, triterpeniod, triterpeniod saponin, terpene, isoprene or compound selected from formulae of the present application, produces inhbetion of cancer growth, cancer invasion, cells invasion, cancer cell invasion, cell adhesion, cell circulation or cell attachment.

This invention shows that the presence of group selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl at carbon position 21, 22, 24 and/or 28 of a pentacyclic triterpene, triterpene, triterpeniod, triterpeniod saponin or compound selected from formulae of the present application, produces inhibition of cancer growth, cancer invasion, cells invasion, cancer cell invasion or macromolecular cell invasion. In an embodiment, the presence of group(s) selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl at carbon position 3, 8, 15, 21, 22, 23, 24 and/or 28 of a triterpene, triterpeniod, triterpeniod saponin or compound selected from formulae of the present application produces activities including inhibition of cancer growth, cancer invasion, cells invasion, cancer cell invasion, cell adhesion, cell attachment or cell circulating wherein the group may attached with an O, S, NH, CH2O to the carbon of triterpene, triterpeniod, triterpeniod saponin or compound selected from formulae of the present application; wherein the group may be selected from group of CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O-C (2-18) Acyl, (CnH2n)O-angeloyl, (CnH2n)O-tigloyl, (CnH2n)O-senecioyl, (CnH2n)O-acetyl, (CnH2n)O-Crotonoyl, (CnH2n)O-3,3-Dimethylartyloyl, (CnH2n)O-Cinnamoyl, (CnH2n)O-Pentenoyl, (CnH2n)O-Hexanoyl, (CnH2n)O-benzoyl, (CnH2n)O-Ethylbutyryl, (CnH2n)O-alkyl, (CnH2n)O-dibenzoyl, (CnH2n)O-benzoyl, (CnH2n)O-alkanoyl, (CnH2n)O-alkenoyl, (CnH2n)O-benzoyl alkyl substituted O-alkanoyl, (CnH2n)O-alkanoyl substituted phenyl, (CnH2n)O-alkenoyl substituted phenyl, (CnH2n)O-aryl, (CnH2n)O-acyl, (CnH2n)O-heterocylic, (CnH2n)O-heteroraryl, (CnH2n)O-alkenylcarbonyl, (CnH2n)O-alkane, (CnH2n)O-alkene and (CnH2n)O-sugar moiety, wherein n is 1 or 2 or 3 or 4 or over 5. In an embodiment, the presence of group at carbon position 24, produces activities. In an embodiment, the presence of group at carbon position 24 and 28 produces activities. In an embodiment, the presence of group at carbon position 24 and 21 produces activities. In an embodiment, the presence of group at carbon position 24, 28 and 21, produces activities. In an embodiment, the presence of group at carbon position 24, 28 and 22 produces activities. In an embodiment, the presence of group at carbon position 24, 28 and 3 produces activities. In an embodiment, the presence of group at carbon position 24, and 3 produces activities. In an embodiment, the presence of group at carbon position 28 and 3 produces activities. In an embodiment, the presence of group at carbon position 3 produces activities. In an embodiment, the presence of group at carbon position 21 and 22 produces activities. In an embodiment, the hemolytic activity of the compound is reduced.

This invention shows a method of synthesizing active compound by attaching functional group to a core compound, wherein the functional group(s) comprises a group which is/are selected from ethanoyl, propanoyl, propenoyl, butanoyl, butenoyl, pentanoyl, pentenoyl, hexanoyl, hexenoyl, heptanoyl, heptenoyl, octanoyl, octenoyl, nonanoyl, nonenoyl, decanoyl, decenoyl, propionyl, 2-propenoyl, crotonoyl, 2-butenoyl, Isobutyryl, methylpropanoyl, 2-methylpropanoyl, ethylbutyryl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, tigloyl, angeloyl, acetyl, crotonoyl, 3,3-Dimethylartyloyl, senecioyl, cinnamoyl, benzoyl, ethylbutyryl, dibenzoyl, alkanoyl, alkenoyl, benzoyl alkyl substituted alkanoyl, alkanoyl substituted phenyl, alkenoyl substituted phenyl, aryl, acyl, heterocylic, and heteroraryl, wherein the core compound is a 5 ring triterpene. In embodiment, the core compound is a 4 ring terpene. In embodiment, the core compound is a 3 ring terpene. In embodiment, the core compound is a 2 ring terpene. In embodiment, the core compound is a 1 ring terpene. The compounds provided in the invention are for treating cancers, inhibition of cancer growth, cancer invasion, cells invasion, cancer cell invasion; cell adhesion, cell attachment, cell circulating; for treating mad cow disease; treating prion diseases; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions or neurodegeneration; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemorrhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitis, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increase the expression of the genes: ANGPT2, DDIT3, LIF and NFKB1Z, and manufacturing an adjuvant composition and venotonic treatment.

Experiments presented in this invention showed that the compound AKOH has no effect in inhibiting cancer growth, cancer invasion, cells invasion or cancer cell invasion. AKOH was obtained by removing the angeloyl groups from carbon positions 21 and 22 of the active Xanifolia Y(Y3). This invention shows that the ability for inhibiting cancer invasion, cells invasion or cancer cell invasion of Xanifolia Y(Y3) are lost by removing angeloyl groups from carbon positions 21 and 22.

Experiments presented in this invention showed that the core compound including E4A, E5A, Xanifolia Y-core have no effect in inhibiting cancer growth, cancer invasion, cells invasion or cancer cell invasion. Xanifolia Y-core was obtained by removing the angeloyl groups from carbon positions 21 and 22, and the sugar moieties from carbon 3 of the active Xanifolia Y(Y3). E4A (E IV A) was obtained by removing the groups from carbon positions 3, 21 and 22 of the active Escin. E5A (E V A) was obtained by removing the groups from carbon positions 3, 21 and 22 of the active Escin. This invention showed that the core compound including E4A, E5A, Xanifolia Y-core and AKOH have no hemolytic activity and no anti-cancer activity.

This invention showed that functional group attached at carbon position 24 of a triterpene did not produce hemolytic activity, which has bio-activities including inhibiting cancer growth, inhibiting cancer invasion, cells invasion or cancer cell invasion. This invention showed that function group(s) attached at carbon position 24 and 1 or 2 or 3 of carbon position 28, 21, 22 of a triterpene did not produce hemolytic activity, which has bio-activities including inhibiting cancer growth, inhibiting cancer invasion, cells invasion or cancer cell invasion.

This invention provides a triterpene with reduced hemolytic activity for treating diseases, wherein the triterpene comprising a group(s) attached at its core producing bio-activities. This invention provides a triterpene with reduced hemolytic activity comprising a group(s) attached at carbon position 24, or carbon position 24 and 1 or 2 or 3 of other position(s) of a triterpene, which has bio-activities. This invention provides a composition comprising a triterpene with reduced hemolytic activity comprising a group(s) attached at carbon position 24, or carbon position 24 and 1 or 2 or 3 of other position(s) of a triterpene, which has bio-activities. This invention provides a method for bio-ativities treatment including but not limited to treating cancers, comprising administering to said subject an effective amount of compound, wherein the compound is a triterpene with reduced hemolytic activity comprising a group(s) attached at carbon position 24, or carbon position 24 and 1 or 2 or 3 of other position(s) of a triterpene, which has bio-activities.

This invention showed that Tig-N, Tig-Q, Tig-R, Tig-T Tig-S and Tig-V do not have hemolytic activity up to 20 ug/ml. The original compound ES lyse 100% red blood cells (RBC) at 5 ug/ml. Compare to Y3, the ACH-Y3 is less potent in hemolytic activity. Tig-R has no hemolytic activity. This invention showed that Tig-N, Tig-Q, Tig-R, Tig-T Tig-S and Tig-V have anti cancer activities.

Many saponins and triterpenes have hemolytic characteristic that damage red blood cells. This severe side effect make people hesitate to use saponins or triterpenes in medicines. This invention produces sythesised saponins and triterpenes with reduced hemolytic characteristic for use as medicament. This invention produces compounds with reduced hemolytic characteristic for use as medicament. The medicament can be used for treating cancer, inhibiting cancer growth, cancer invasion, cells invasion or cancer cell invasion.

This invention shows that the ability for inhibiting cancer growth, cancer invasion, cells invasion or cancer cell invasion are maintained when the sugar moieties are removed from carbon position 3 of an active compound, triterpene, triterpeniod, or triterpeniod saponin. Experiments presented in this invention showed that the compound ACH-Y3 has the ability to inhibit cancer invasion, cells invasion or cancer cell invasion. The compound ACH-Y3 was obtained by removing the sugar moieties from carbon position 3 of a active Xanifolia Y(Y3). This invention shows that the ability for inhibiting cancer invasion, cells invasion or cancer cell invasion are maintained when the sugar moieties are removed from the carbon position 3 of active Xanifolia Y(Y3).

A compound which has bio-activities including inhibiting cancer growth, inhibiting cancer invasion, cells invasion or cancer cell invasion is called active compound.

This invention provides a use for compounds, compositions, and methods for manufacturing medicament for treating cancers, inhibition of cancer growth, cancer invasion, cells invasion, cancer cell invasion; cell adhesion, cell attachment, cell circulating, or for inhibiting cancer metastasis, wherein the compounds comprise the structures selected from the formulae of the present application, wherein the compounds can be synthesized or isolated, wherein the compounds comprise the pentacyclic triterpenes, wherein the compounds with reduced hemolytic, wherein the cells comprise cancer cells, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer. The method of inhibiting cancer invasion, cells invasion or cancer cell invasion activities uses non-cytotoxic drug concentrations. The method of inhibiting metastasis uses non-cytotoxic drug concentrations. There is no noticeable change in cell morphology.

This invention provides triterpene(s) with reduced hemolytic activity for treating diseases, wherein the triterpene comprising a group(s) attached at its core producing bio-activities. This invention provides a triterpene with reduced hemolytic effect, comprising a group(s) attached at carbon position 24, or carbon position 24 and 1 or 2 or 3 of other position(s) of a triterpene, which has bio-activities. This invention provides a composition comprising a triterpene with reduced hemolytic activity comprising a group(s) attached at carbon position 24, or carbon position 24 and 1 or 2 or 3 of other position(s) of a triterpene, which has bio-activities. This invention provides a method for bio-ativities treatment including but not limited to treating cancers, comprising administering to said subject an effective amount of compound, wherein the compound is a triterpene with reduced hemolytic activity, comprising a group(s) attached at carbon position 24, or carbon position 24 and 1 or 2 or 3 of other position(s) of a triterpene, which has bio-activities, wherein a compound selected from A1-18, A20-32, B1-18, B20-32, C1-18, C20-32, D1-18, D20-32, D1-18, D20-32, D1-18, D20-32, D1-18, D20-32, D1-18, D20-32, E1-18, E20-32, G1-18, G20-32, H1-18, H20-32, I1-18, I20-32, J1-18, J20-32, K1-18, K20-32, Tig-Sen-n, Tig-Cro-n, Tig-Acy-n, Tig-Pen-n, Tig-Hex-n, Tig-Cin-n, Tig-Ang-n, Tig-Eth-n, Tig-R-Sen-n, Tig-R-Cro-n, Tig-R-Acy-n, Tig-R-Pen-n, Tig-R-Hex-n, Tig-R-Cin-n, Tig-R-Ang-n, Tig-R-Eth-n, wherein n=1 to 6, and a salt, ester, metabolite thereof, and the compounds selected from formulae 2A, and K; wherein the compound is selected from Tig-N, Tig-Q, Tig-R, Tig-T Tig-S and Tig-V.

This invention provides methods for treating cancers, inhibition of cancer growth, cancer invasion, cells invasion, cancer cell invasion; cell adhesion, cell attachment, cell circulating, migration, metastasis or growth of cancers, wherein the methods comprise affecting gene expression, wherein the methods comprise stimulating gene expression, or wherein the methods comprise inhibiting the gene expression, or wherein the methods comprise administering to a subject an effective amount of compounds, compositions in this application. In an embodiment, the method comprises contacting said cell with a compound selected from A1-18, A20-32, B1-18, B20-32, C1-18, C20-32, D1-18, D20-32, D1-18, D20-32, D1-18, D20-32, D1-18, D20-32, D1-18, D20-32, E1-18, E20-32, G1-18, G20-32, H1-18, H20-32, I1-18, I20-32, J1-18, J20-32, K1-18, K20-32, Xanifolia Y0, Y1, Y2, Y(Y3), Y5, Y7, Y8, Y9, Y10, Xanifolia (x), M10, Escin (bES), Aescin, ACH-Y(Y3), ACH-Y10, ACH-Y2, ACH-Y8, ACH-Y7, ACH-Y0, ACH-X, ACH-Z4, ACH-Z1, ACH-Escin (bES), ACH-M10, Tig-Sen-n, Tig-Cro-n, Tig-Acy-n, Tig-Pen-n, Tig-Hex-n, Tig-Cin-n, Tig-Ang-n, Tig-Eth-n, Tig-R-Sen-n, Tig-R-Cro-n, Tig-R-Acy-n, Tig-R-Pen-n, Tig-R-Hex-n, Tig-R-Cin-n, Tig-R-Ang-n, Tig-R-Eth-n, wherein n=1 to 6, and a salt, ester, metabolite thereof, and the compounds selected from formulae 2A, and K. In vitro studies show that a compound selected from structure (2A) or (K) inhibits cell adhesion to culture flasks. The compound blocks the function of these adhesive molecules on cells. In an embodiment, the selected compound blocks the function of these adhesive molecules on cells. In an embodiment, the selected compound blocks the function of these adhesive molecules on carcinoma cells. In an embodiment, the selected compound blocks the function of these adhesive molecules on the mesothelial cells. This invention provides an anti adhesion therapy which uses the compound as a mediator or inhibitor of adhesion proteins and angiopoietins. It inhibits excess adhesion and inhibits cell attachment. This invention provides compounds for use as a mediator for cell circulating, cell moving and inflammatory diseases. In an embodiment, the selected compound binds to the adhesive proteins (by masking) on the membrane and inhibits the interaction of adhesion proteins with their receptors. In an embodiment, the selected compound's action on the membrane affects adhesion proteins' function in the membrane. The lost of adhesion activity of cancer cells is result from direct or indirect action of the selected compound on membrane proteins. (Our purification methods and biological assays include the MTT assay in International Application No. PCT/US05/31900, filed Sep. 7, 2005, U.S. Ser. No. 11/289,142, filed Nov. 28, 2005, and U.S. Ser. No. 11/131, 551, filed May 17, 2005, and PCT/US2008/002086, 1188-ALA-PCT, filed Feb. 15, 2008, the cell invasion experiments methods in International Application PCT/US2010/0042240, filed Jul. 16, 2010)

This invention provides a use of compounds or methods for inhibiting cancer invasion, cell invasion, cancer cell invasion, macromolecular cell invasion, migration, metastasis or growth of cancers, wherein this invention comprises a process and method for administration of the composition, wherein administration is by intravenous injection, intravenous drip, intraperitoneal injection or oral administration; wherein administration is by intravenous drip: 0.003-0.03 mg/kg body weight of compound dissolved in 250 ml of 10% glucose solution or in 250 ml of 0.9% NaCl solution, or by intravenous injection: 0.003-0.03 mg/kg body weight per day of compound dissolved in 10-20 ml of 10% glucose solution or of 0.9% NaCl solution, or 0.01-0.03 mg/kg body weight of compound dissolved in 250 ml of 10% glucose solution or in 250 ml of 0.9% NaCl solution, or by intravenous injection: 0.01-0.03 mg/kg body weight per day of compound dissolved in 10-20 ml of 10% glucose solution or of 0.9% NaCl solution, or 0.01-0.05 mg/kg body weight of compound dissolved in 250 ml of 10% glucose solution or in 250 ml of 0.9% NaCl solution, or by intravenous injection: 0.01-0.05 mg/kg body weight per day of compound dissolved in 10-20 ml of 10% glucose solution or of 0.9% NaCl solution, or 0.05-0.2 mg/kg body weight of compound dissolved in 250 ml of 10% glucose solution or in 250 ml of 0.9% NaCl solution, or by intravenous injection: 0.05-0.2 mg/kg body weight per day of compound dissolved in 10-20 ml of 10% glucose solution or of 0.9% NaCl solution, or by intravenous drip: 0.1-0.2 mg/kg body weight per day of compound dissolved in 250 ml of 10% glucose solution or in 250 ml of 0.9% NaCl solution, or by intravenous injection: 0.1-0.2 mg/kg body weight per day compound dissolved in 10-20 ml of 10% glucose solution or of 0.9% NaCl solution, or by intraperitoneal injection (I.P.): 2.5 mg/kg body weight per day compound dissolved in 10% glucose solution or of 0.9% NaCl solution, or by oral administration wherein the dosage of mammal is 1-10 mg/kg, 10-30 mg/kg, 30-60 mg/kg, or 60-90 mg/kg body weight of compound, or by intravenous injection or intravenous drip wherein the dosage of mammal is 0.01-0.1 mg/kg body weight, 0.1-0.2 mg/kg, 0.2-0.4 mg/kg body weight, or 0.4-0.6 mg/kg body weight of compound, or by intraperitoneal injection (I.P.) wherein the dosage of mammal is 1-3 mg/kg, 3-5 mg/kg, 4-6 mg/kg, or 6-10 mg/kg body weight of compound.

This invention provides a use of compounds or methods for treating cancers, inhibition of cancer growth, cancer invasion, cells invasion, cancer cell invasion; macromolecular cell invasion, cell adhesion, cell attachment; cell circulating, migration, metastasis or growth of cancers, infection or re-infection of virus or infectious macromolecules, and cancer cell fusion, wherein the invention comprises a pharmaceutical composition comprising the compound of this invention or a pharmaceutically acceptable salt thereof, and a pharmaceutically acceptable carrier or diluent, wherein said compound is present in a concentration of 0.01 ug/ml to 65 ug/ml, or wherein said compound is present in a concentration of 0.01 ug/ml to 40 ug/ml, or wherein said compound is present in a concentration of 0.01 ug/ml to 30 ug/ml, or wherein said compound is present in a concentration of 0.01 ug/ml to 10 ug/ml, or wherein said compound is present in a concentration of 0.01 ug/ml to 5 ug/ml, or wherein said compound is present in a concentration of 5 ug/ml to 10 ug/ml, or wherein said compound is present in a concentration of 0.1 ug/ml to 5 ug/ml, or wherein said compound is present in a concentration of 0.1 ug/ml to 7.5 ug/ml, or wherein said compound is present in a concentration of 0.1 ug/ml to 10 ug/ml, or wherein said compound is present in a concentration of 0.1 ug/ml to 15 ug/ml, or wherein said compound is present in a concentration of 0.1 ug/ml to 20 ug/ml, or wherein said compound is present in a concentration of 0.1 ug/ml to 30 ug/ml, or wherein said compound is present in a concentration of 1 ug/ml to 5 ug/ml, or wherein said compound is present in a concentration of 1 ug/ml to 7.5 ug/ml, or wherein said compound is present in a concentration of 1 ug/ml to 10 ug/ml, or wherein said compound is present in a concentration of 1 ug/ml to 15 ug/ml, or wherein said compound is present in a concentration of 1 ug/ml to 20 ug/ml, or wherein said compound is present in a concentration of 1 ug/ml to 30 ug/ml, or wherein said compound is present in a concentration of 3 ug/ml to 5 ug/ml, or wherein said compound is present in a concentration of 3 ug/ml to 7.5 ug/ml, or wherein said compound is present in a concentration of 3 ug/ml to 10 ug/ml, or wherein said compound is present in a concentration of 3 ug/ml to 15 ug/ml, or wherein said compound is present in a concentration of 3 ug/ml to 20 ug/ml, or wherein said compound is present in a concentration of 3 ug/ml to 30 ug/ml, or wherein said compound is present in a concentration of 4 ug/ml to 5 ug/ml, or wherein said compound is present in a concentration of 4 ug/ml to 7.5 ug/ml, or wherein said compound is present in a concentration of 4 ug/ml to 10 ug/ml, or wherein said compound is present in a concentration of 4 ug/ml to 15 ug/ml, or wherein said compound is present in a concentration of 4 ug/ml to 20 ug/ml, or wherein said compound is present in a concentration of 4 ug/ml to 30 ug/ml, or wherein said compound is present in a concentration of 5 ug/ml to 8 ug/ml, or wherein said compound is present in a concentration of 5 ug/ml to 9 ug/ml, or wherein said compound is present in a concentration of 5 ug/ml to 10 ug/ml, or wherein said compound is present in a concentration of 5 ug/ml to 15 ug/ml, or wherein said compound is present in a concentration of 5 ug/ml to 20 ug/ml, or wherein said compound is present in a concentration of 5 ug/ml to 30 ug/ml, or wherein said compound is present in a concentration of 7 ug/ml to 8 ug/ml, or wherein said compound is present in a concentration of 7 ug/ml to 9 ug/ml, or wherein said compound is present in a concentration of 7 ug/ml to 10 ug/ml, or wherein said compound is present in a concentration of 7 ug/ml to 15 ug/ml, or wherein said compound is present in a concentration of 7 ug/ml to 20 ug/ml, or wherein said compound is present in a concentration of 7 ug/ml to 30 ug/ml.

This invention provides a use of compounds or methods for treating cancers, inhibition of cancer growth, cancer invasion, cells invasion, cancer cell invasion; macromolecular cell invasion, cell adhesion, cell attachment, cell circulating, migration, metastasis or growth of cancers, infection or re-infection of virus or infectious macromolecules, and cancer cell fusion, wherein the invention comprises a pharmaceutical composition comprising the compound of this invention or a pharmaceutically acceptable salt thereof, and a pharmaceutically acceptable carrier or diluent, wherein said compound is present in a concentration of 0.008 uM to 80 uM, or wherein said compound is present in a concentration of 0.01 uM to 60 uM, or wherein said compound is present in a concentration of 0.01 uM to 50 uM, or wherein said compound is present in a concentration of 0.01 uM to 40 uM, or wherein said compound is present in a concentration of 0.01 uM to 30 uM, or wherein said compound is present in a concentration of 0.01 uM to 20 uM, or wherein said compound is present in a concentration of 0.01 uM to 10 uM, or wherein said compound is present in a concentration of 5 uM to 10 uM, or wherein said compound is present in a concentration of 0.1 uM to 5 uM, or wherein said compound is present in a concentration of 0.1 uM to 7.5 uM, or wherein said compound is present in a concentration of 0.1 uM to 10 uM, or wherein said compound is present in a concentration of 0.1 uM to 15 uM, or wherein said compound is present in a concentration of 0.1 uM to 20 uM, or wherein said compound is present in a concentration of 0.1 uM to 30 uM or wherein said compound is present in a concentration of 0.1 uM to 40 uM, or wherein said compound is present in a concentration of 0.1 uM to 50 uM or wherein said compound is present in a concentration of 0.1 uM to 60 uM, or wherein said compound is present in a concentration of 0.1 uM to 80 uM, or wherein said compound is present in a concentration of 1 uM to 5 uM, or wherein said compound is present in a concentration of 1 uM to 7.5 uM, or wherein said compound is present in a concentration of 1 uM to 10 uM, or wherein said compound is present in a concentration of 1 uM to 15 uM, or wherein said compound is present in a concentration of 1 uM to 20 uM, or wherein said compound is present in a concentration of 1 uM to 30 uM or wherein said compound is present in a concentration of 1 uM to 40 uM, or wherein said compound is present in a concentration of 1 uM to 50 uM or wherein said compound is present in a concentration of 1 uM to 60 uM, or wherein said compound is present in a concentration of 1 uM to 80 uM, or wherein said compound is present in a concentration of 3 uM to 5 uM, or wherein said compound is present in a concentration of 3 uM to 7.5 uM, or wherein said compound is present in a concentration of 3 uM to 10 uM, or wherein said compound is present in a concentration of 3 uM to 15 uM, or wherein said compound is present in a concentration of 3 uM to 20 uM, or wherein said compound is present in a concentration of 3 uM to 30 uM or wherein said compound is present in a concentration of 3 uM to 40 uM, or wherein said compound is present in a concentration of 3 uM to 50 uM or wherein said compound is present in a concentration of 3 uM to 60 uM, or wherein said compound is present in a concentration of 3 uM to 80 uM, or wherein said compound is present in a concentration of 5 uM to 8 uM, or wherein said compound is present in a concentration of 5 uM to 10 uM, or wherein said compound is present in a concentration of 5 uM to 15 uM, or wherein said compound is present in a concentration of 5 uM to 20 uM, or wherein said compound is present in a concentration of 5 uM to 30 uM or wherein said compound is present in a concentration of 5 uM to 40 uM, or wherein said compound is present in a concentration of 5 uM to 50 uM or wherein said compound is present in a concentration of 5 uM to 60 uM, or wherein said compound is present in a concentration of 5 uM to 80 uM. or wherein said compound is present in a concentration of 7 uM to 8 uM, or wherein said compound is present in a concentration of 7 uM to 10 uM, or wherein said compound is present in a concentration of 7 uM to 15 uM, or wherein said compound is present in a concentration of 7 uM to 20 uM, or wherein said compound is present in a concentration of 7 uM to 30 uM or wherein said compound is present in a concentration of 7 uM to 40 uM, or wherein said compound is present in a concentration of 7 uM to 50 uM or wherein said compound is present in a concentration of 7 uM to 60 uM, or wherein said compound is present in a concentration of 7 uM to 80 uM.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains.

It is to be noted that the transitional term "comprising", which is synonymous with "including", "containing" or "characterized by", is inclusive or open-ended and does not exclude additional, un-recited elements or method steps.

Example 1

Tablet for Dose Containing 10 mg, 20 mg 30 mg of Active Compound

| Active compound | 1 mg | 5 mg | 10 mg | 20 mg | 30 mg |
| Microcrystalline cellulose | 20 mg | 20 mg | 19.75 mg | 60 mg | 100 mg |

-continued

| | | | | |
|---|---|---|---|---|
| Corn starch | 29 mg | 24.5 mg | 19.75 mg | 19.25 mg | 18.5 mg |
| Magnesium stearate | 0 mg | 0.5 mg | 0.5 mg | 0.75 mg | 1.5 mg |

The active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1, 5, 10, 20, 30 mg, respectively of active ingredient per tablet.

Example 2

Intravenous Solution Preparation

An intravenous dosage form of the active compound is prepared as follows:
Active compound 1-10 ug
Sodium citrate 5-50 mg
Citric acid 1-15 mg
Sodium chloride 1-8 mg
Water for injection (USP) q.s. to 1 mL
Utilizing the above quantities, the active compound is dissolved at room temperature in a prepared solution of sodium chloride, citric acid, and sodium citrate in water for injection.

Example 3

Intravenous Drip Preparation 0.25-2.5 mg compound dissolved in 250 ml of 10% glucose solution or in 250 ml of 0.9% NaCl solution.

Intravenous drip preparation: 1-2 mg compound dissolved in 250 ml of 10% glucose solution or in 250 ml of 0.9% NaCl solution Treatment of angelic acid with one of the many standard chlorinating reagents including phosphorus ocychloride, phosphorus trichloride and thionyl chloride produces tigloyl chloride. Oxalyl chloride produces a 2:1 ratio of angeloyl chloride to tigloyl chloride. Treatment of potassium salt in diethyl ether with oxalyl chloride and catalytic DMF for 2 hr at 0 C produces pure angeloyl chloride.

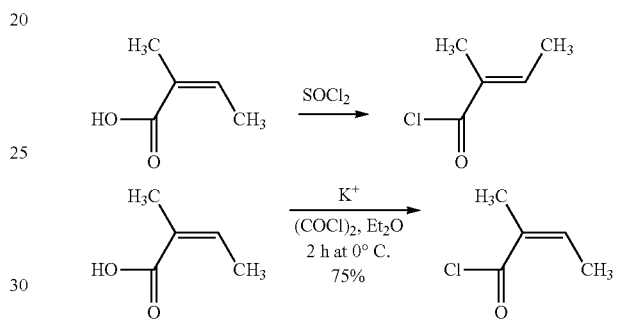

Acid Hydrolysis of the Following Compounds:
a) Xanifolia (Y),

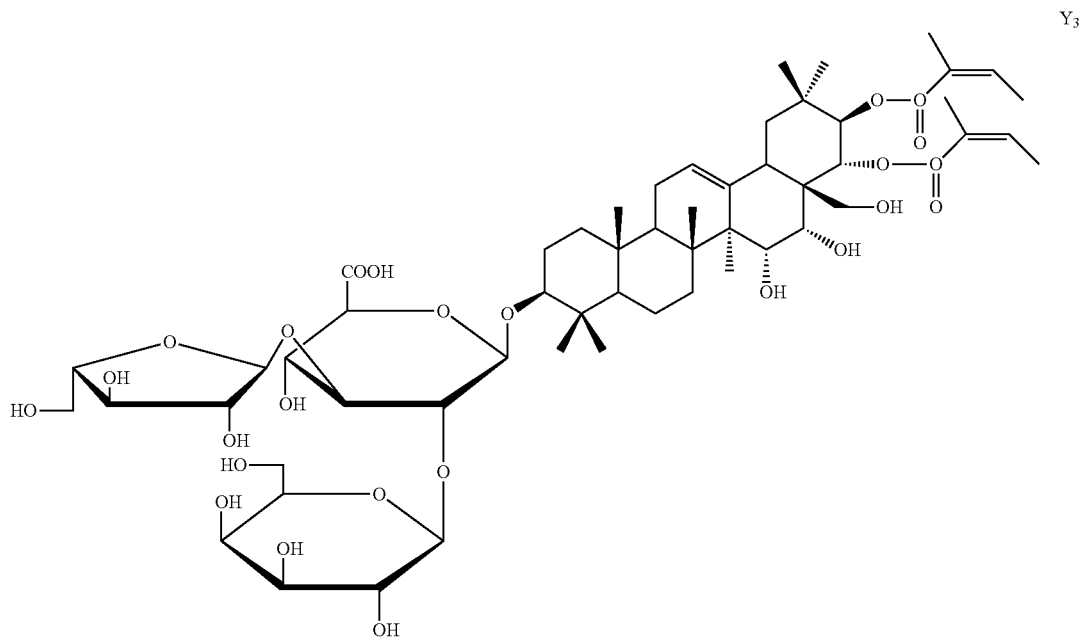

or chemical name: 3-O-[β-D-galactopyranosyl (1→2)]-α-L-arabinofuranosy (1→3)-β-D-glucuronopyranosyl-21,22-O-diangeloyl-3β,15α,16α,21β,22α,28-hexahydroxyolean-12-ene;
c) Xanifolia (Y2),
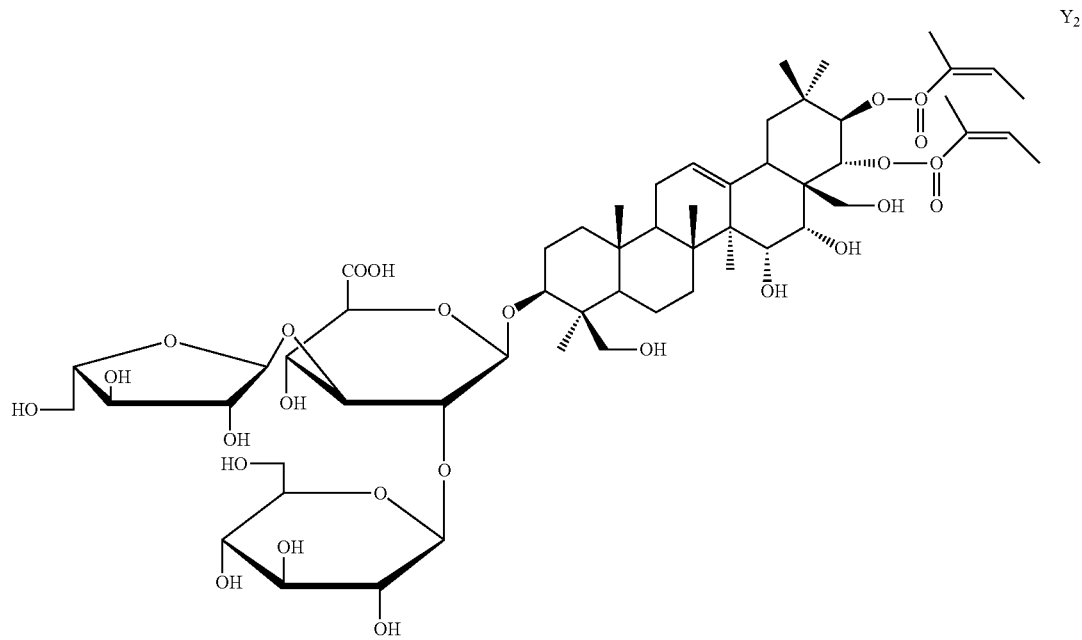
or chemical name: 3-O-[β-D-glucopyranosyl-(1→2)]-α-L-arabinofuranosy (1→3)-β-D-glucuronopyranosyl-21,22-O-diangeloyl-3β,15α,16α,21β,22α,24β,28-heptahydroxy-olean-12-ene;
d) Xanifolia (Y8),
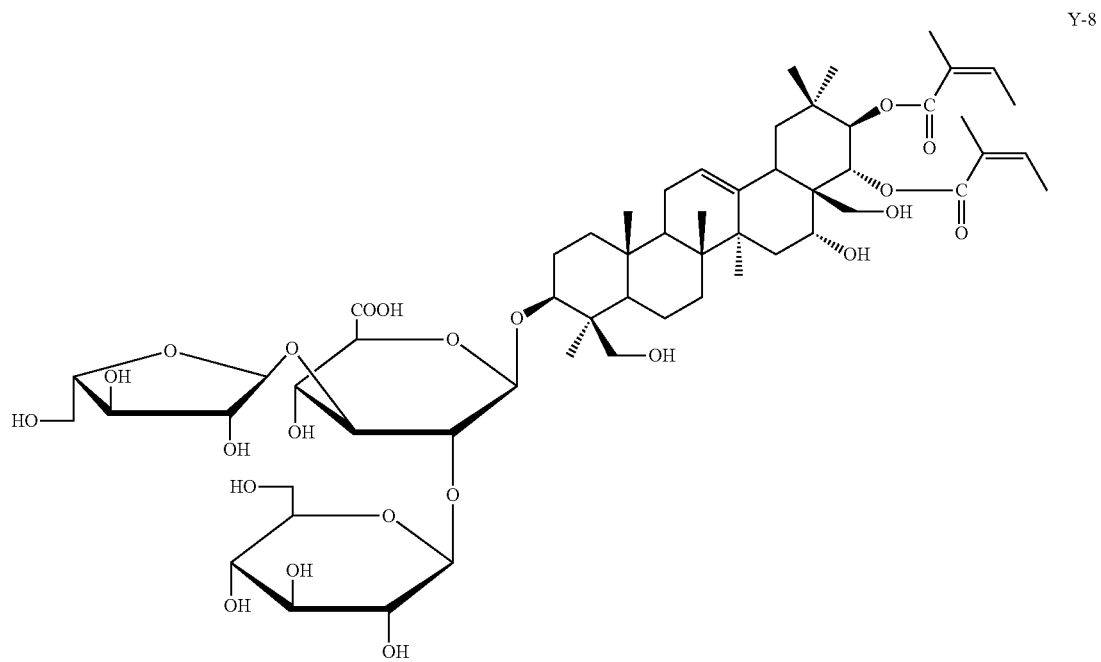

or chemical name: 3-O-[β-glucopyranosyl (1→2)]-α-arabinofuranosyl (1→3)-β-glucuronopyranosyl-21,22-O-diangeloyl-3β,16α, 2β,22α,24β,28-hexahydroxyolean-12-ene;
f) Xanifolia (Y10),
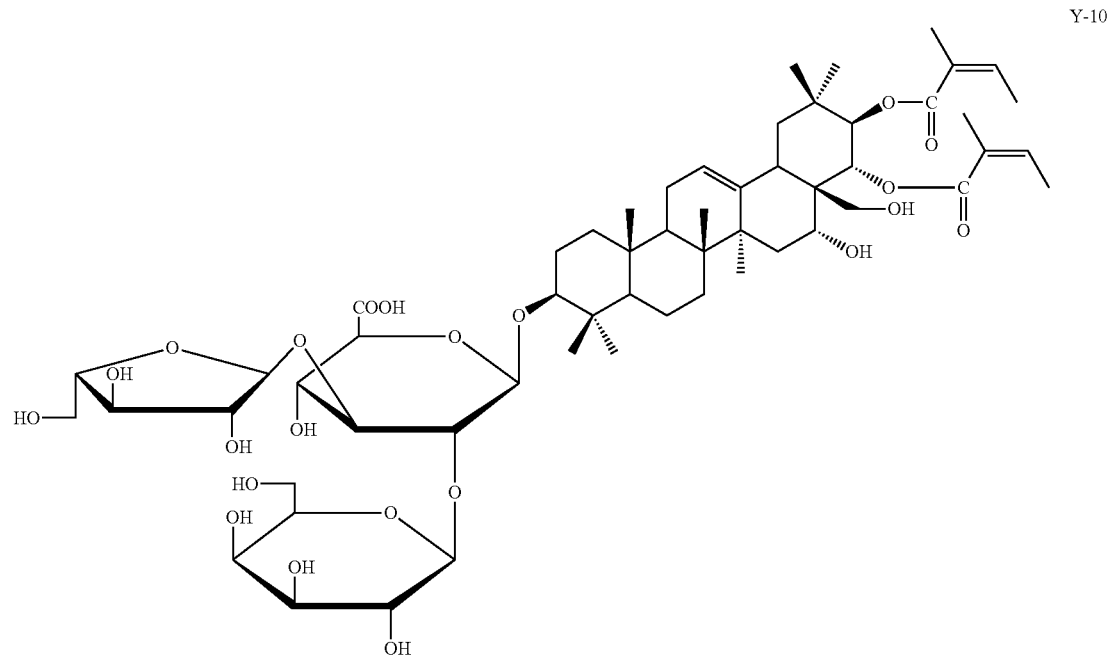
or chemical name: 3-O-[β-galactopyranosyl (1→2)]-α-arabinofuranosyl (1→3)-β-glucuronopyranosyl-21,22-O-diangeloyl-3β,16α,2β,22α,28-pentahydroxyolean-12-ene.
j) structure (M10)
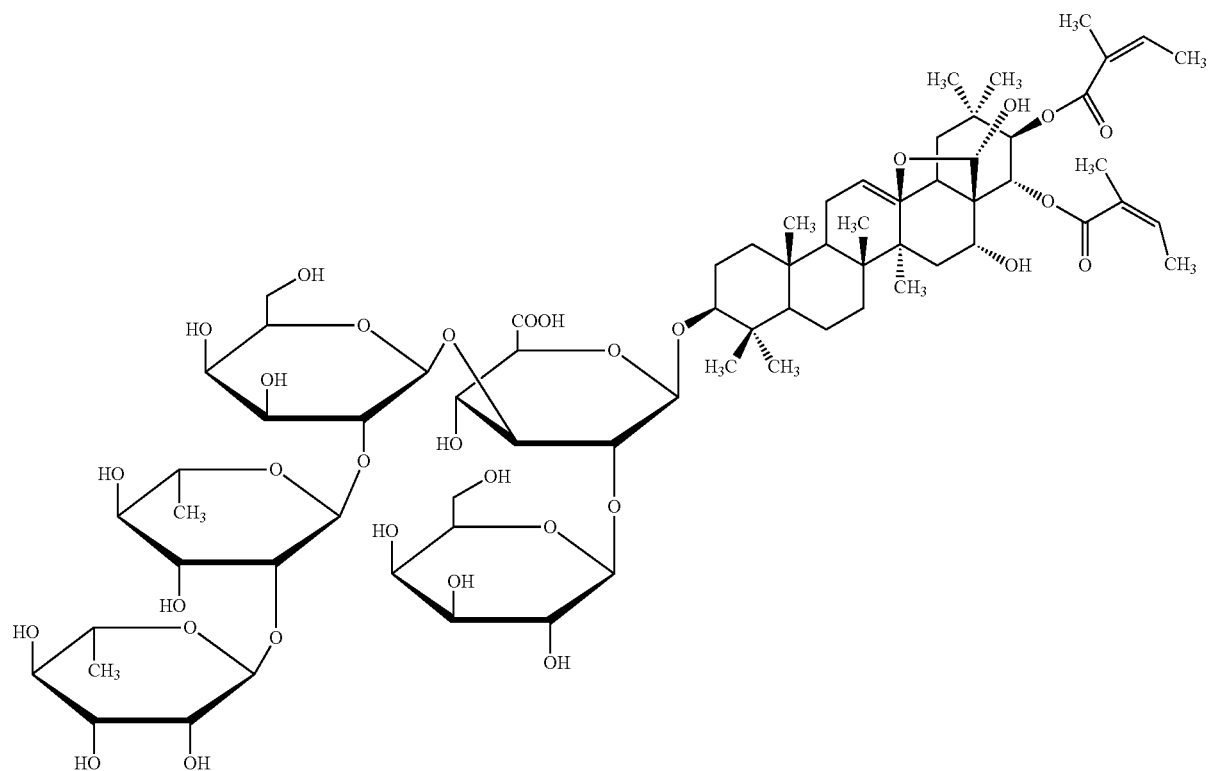

m) structure (bES):
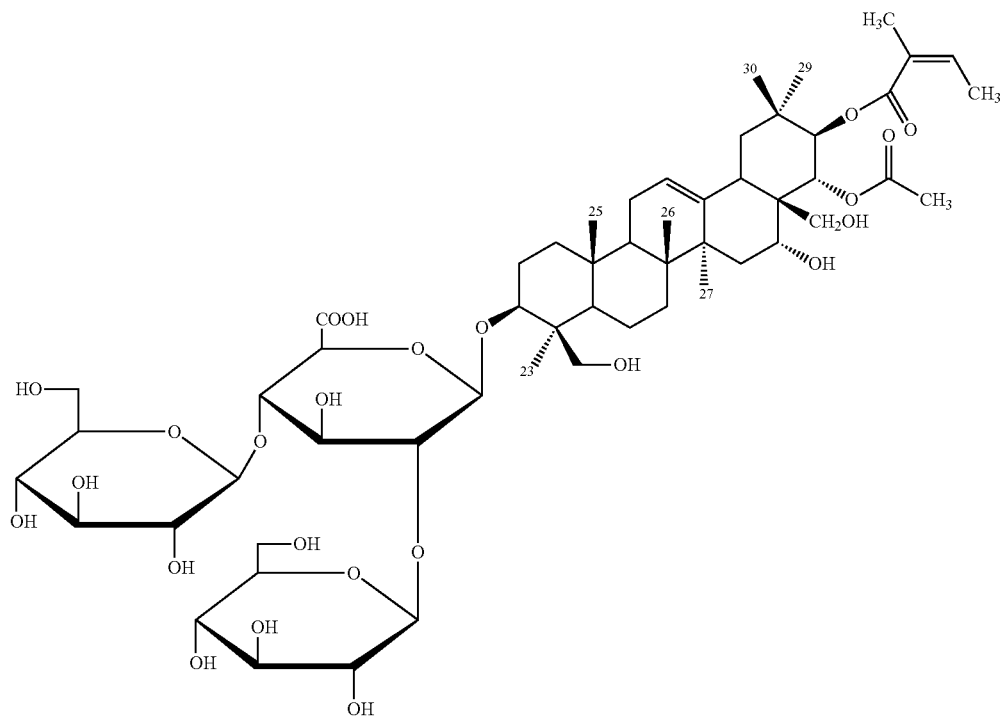
After acid hydrolysis of the above, an isolated, purified or synthesized compound is produced having a structure (ACH) selected from following:
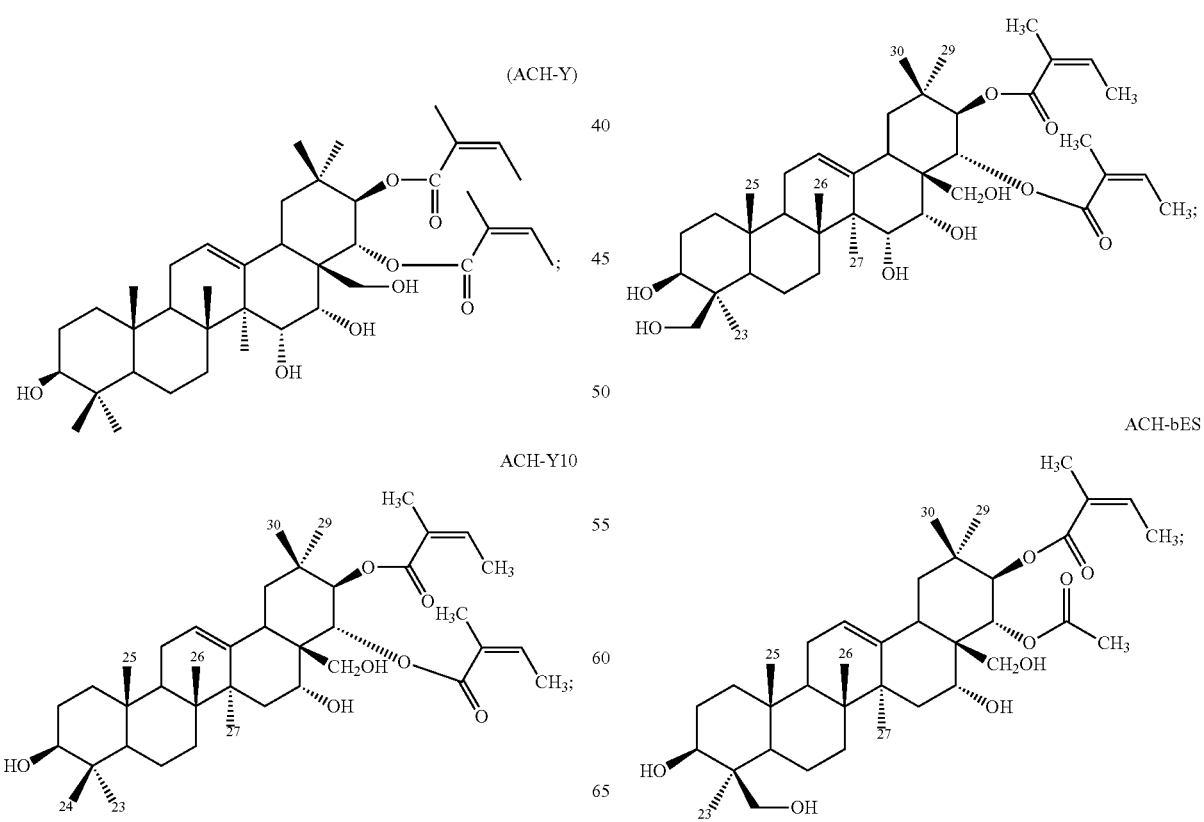

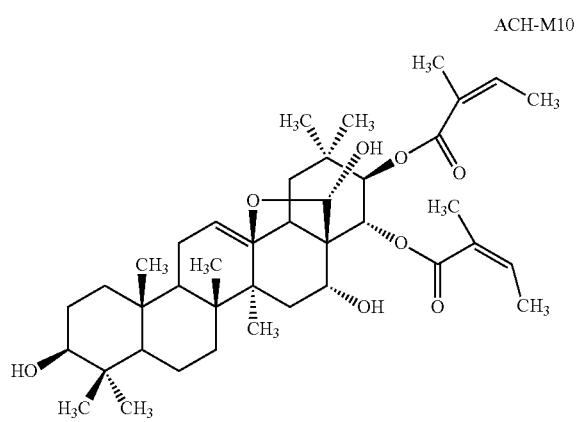

ACH-M10

The composition comprises bioactive compounds from natural plants or synthesis.

The program is based on our purification methods and biological assays including the MTT assay. See International Application No. PCT/US05/31900, filed Sep. 7, 2005, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, Ser. No. 12/344,682, 1020-B1-US, filed Dec. 29, 2008. The details of Analysis of gene expression of ES2 cells after Y-treatment by Microarray, Data Analysis Methods and Western blot in PCT/US2008/002086, 1188-ALA-PCT, filed Feb. 15, 2008, and the cell invasion experiments methods in International Application PCT/US2010/0042240, filed Jul. 16, 2010.

The Haemolytic Assay

Erythrocytes (RBC) were isolated from human blood (EDTA whole blood, collected randomly). 50 ul of the 10% RBC suspension (in PBS) was added to 2 ml of sample solutions (concentration range from 0.1 ug/ml to 400 ug/ml) in PBS. The mixture was vortexed briefly and sat for 60 min at room temperature. The mixture was spun at 3K for 10 min and the relative amounts of lysed hemoglobin in the supernatant were measured at 540 nm. The synthetic compounds of present application were tested with this method.

Acid Hydrolysis of Saponin 15 mg Xanifolia-Y was dissolved in 1 ml of methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (ACH-Y) was achieved by HPLC with isocratic elution of 80-100% acetonitrile. Repeating the experiment with compounds Z4, Y10, Y2, Y8, Y7, Y0, X, M10 and ESCIN (bES) gives the following compounds respectively: ACH-Z4, ACH-Y10, ACH-Y2, ACH-Y8, ACH-Y7, ACH-Y0, ACH-X, ACH-E, ACH-Z5, ACH-M10 and ACH-bES.

Removal of the Acyl Group by Alkaline Hydrolysis 20 mg of Xanifolia-Y was dissolved in 0.5 ml of 1N NaOH. The solution was incubated in 80 C water bath for 4 hours. It was cooled to room temperature before being neutralized with 0.5 ml 1N HCl (adjust pH to about 3). The mixture was extracted with 2 ml 1-butanol 3 times. The butanol fractions were collected and lyophilized. The hydrolyzed saponin was further purified with HPLC in a C-18 column eluted with 25% acetonitrile.

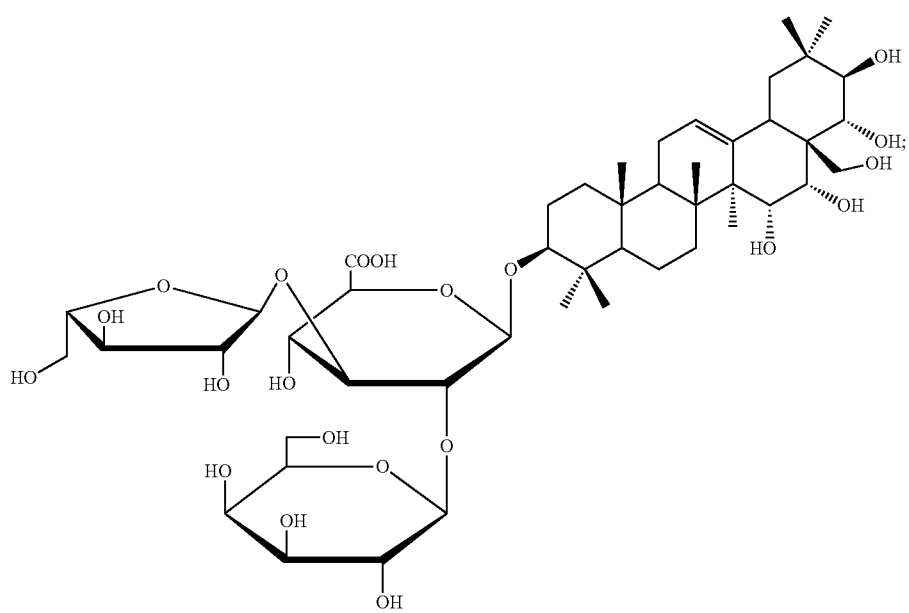

AKOH-Y

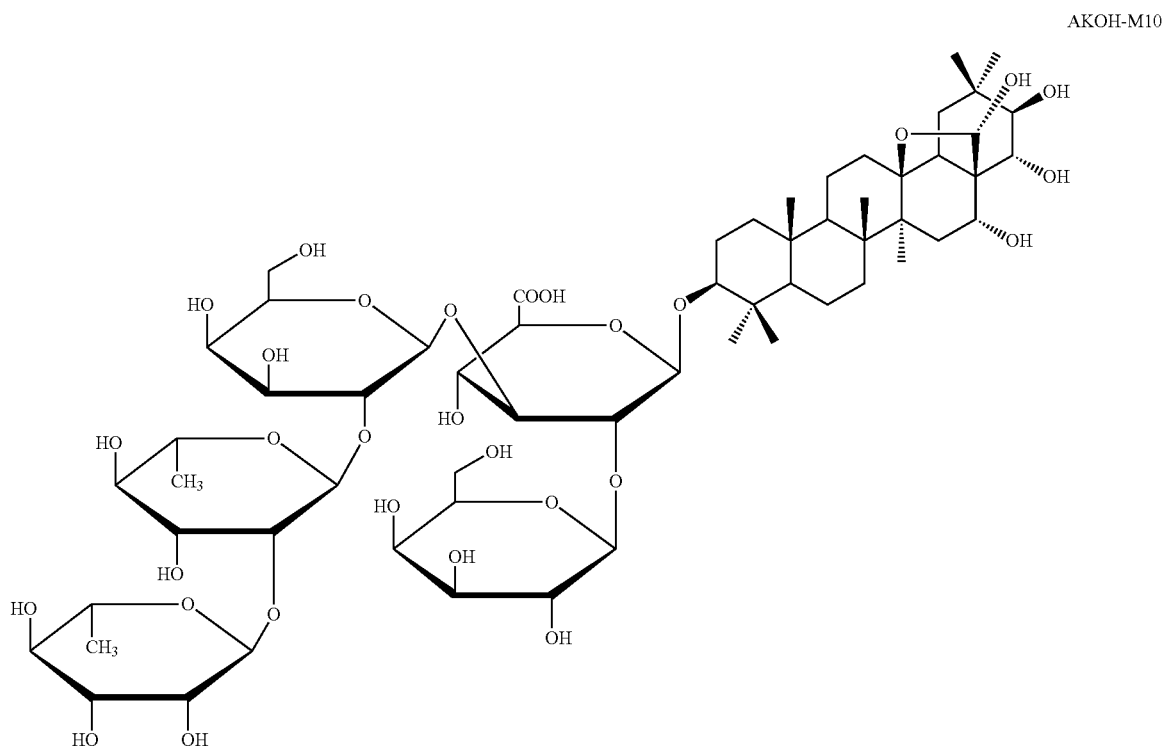

AKOH-M10

Compounds AKOH-Y and AKOH-M10 do not show the ability to inhibit cancer growth, cancer invasion, cells invasion or cancer cell invasion.

Core Compound

A core compound or pentacyclic triterpenes, hydroxylated triterpenes is obtained by acid and alkaline hydroysis of saponin from natural sources. A pentacyclic triterpene can also be obtained by synthetic methods. A method for synthesizing the core compound is as follows:

Beta-Escin, compound Y, Y10, Y2, Y8, Y7, Y0, X, or M10 dissolved in 1M NaOH (20 mg/ml) was incubated at 70 C for 5 hours. The hydrolyzed solution was neutralized with HCl and the water was evaporated by lyophilization. The product was dissolved in 50% methanol and 1N HCl. The mixture was incubated at 70 C for 5 hours. The solution was neutralized with NaOH. The hydrolyzed product was extracted with ethylacetate, which was subsequently removed by evaporation. Further purification of the hydrolyzed product of core compounds including (E4A) were archived with FPLC chromatography in a C18 column equilibrated with 70% acetonitrile/TFA at the flow rate of 1 ml/min. The core compounds are obtained.

The core compounds do not show the ability to inhibit cancer growth, cancer invasion, or cell adhesion. The structures of core compounds:

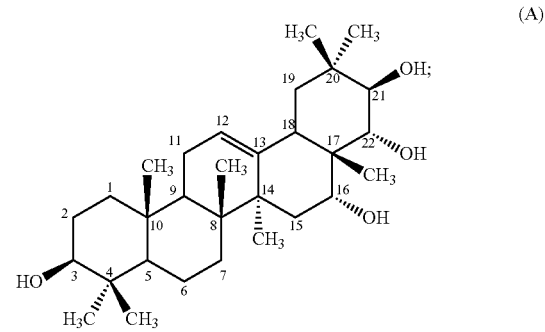

(A)

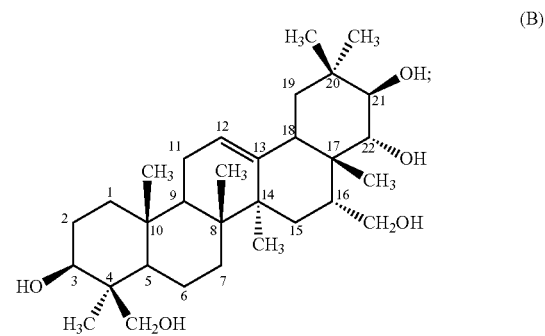

(B)

25
-continued
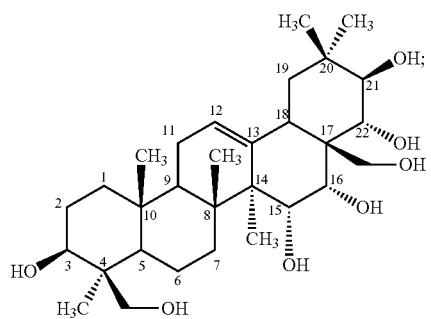
(C)
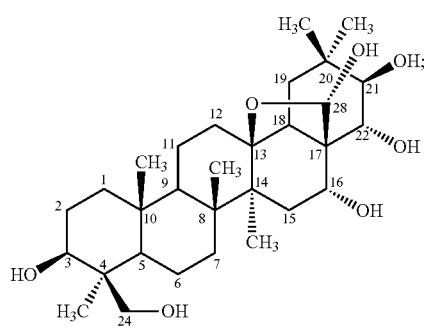
(D1)
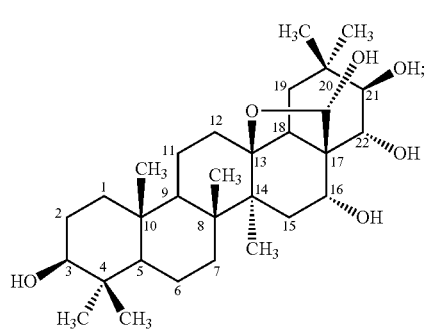
(D2)
also named bES-core, E IV A, ES4A, E4A or (E)
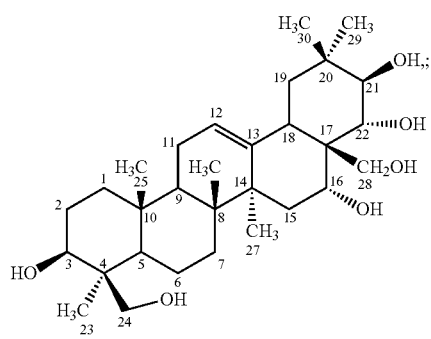
also named as ES V, E5A or (F)
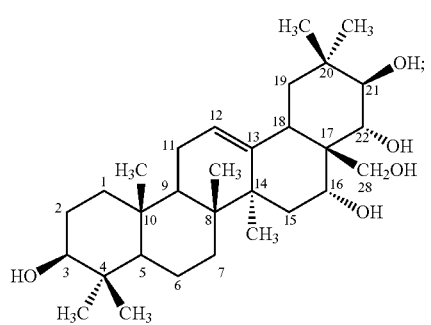
26
-continued
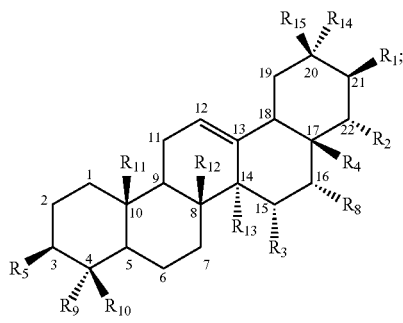
(G)
wherein R1, R2, R5, R8 represent OH; R3 represents OH, H or absent; R4, R10 represent CH3 or CH2OH; R9, R11, R12, R13, R14, R15 represent CH3;
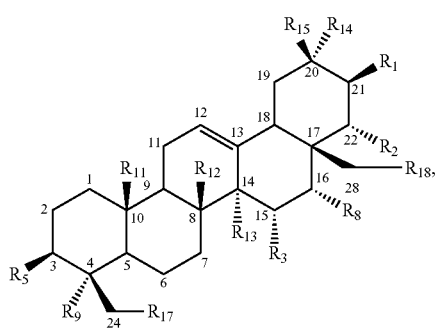
(H1)
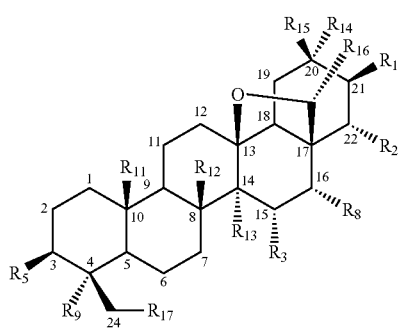
(H2)
wherein R1, R2, R5, R8, R17, R18 represent OH; R3 represents OH, H or absent; R9, R11, R12, R13, R14, R15 represent CH3.
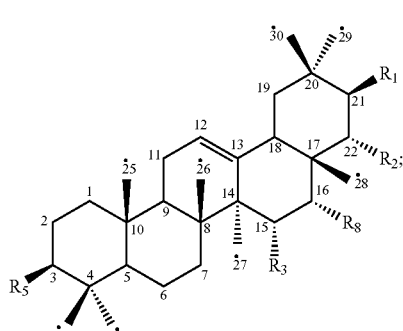
(J)

A typical numbering 1 to 30 of carbon positions of a pentacyclic triterpene.

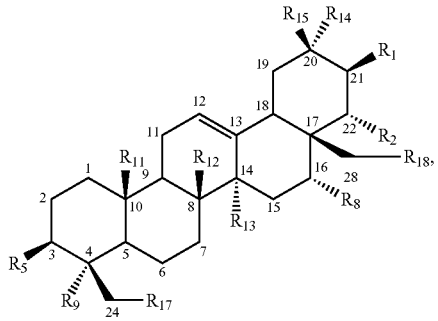

wherein R1, R2, R5, R8, R17, R18 represent OH; R9, R11, R12, R13, R14, R15 represent CH3, also named E4A or (E).

This invention provides a method of synthesizing new active compounds. A method of attaching functional groups to the core compounds including but not limited to (A), (B), (C), (D1), (D2), (E), (F), (G), (H1), (H2), (J)] involves esterification of core compounds with acyl halide, wherein the halide including chloride, bromide, fluoride and iodide, wherein the acyl halide comprises acyl chloride, wherein acyl chloride including but not limited to Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride, Ethylbutyryl chloride, Propionyl chloride, 2-Propenoyl chloride, Isobutyryl chloride, Butyryl chloride, (2E)-2-pentenoyl chloride, 4-Pentenoyl chloride, 5-Hexenoyl chloride, Heptanoyl chloride, Octanoyl chloride, Nonanoyl chloride, Decanoyl chloride, Lauroyl chloride, Myristoyl chloride, Oleoyl chloride for 5 sec, 1 min, 2 min, 5 min, 10 min, 30 min, 1 hr, 2 hr, 18 hr, 2 days or 3 days at 0 C, 25 C or 75 C temperature. At the end of reaction, 5 ml of 2N HCl or 1M NaHCO3 is added to the reaction mixture. The solution is then extracted 3 times with 10 ml of ethyl acetate which is then evaporated under vacuum and at 45 C and lyophilization. The reaction product is dissolved in 80% acetonitrile-0.005% Trifluoroacetic acid. The active esterification products are purified with HPLC. MTT activity was performed to test the activity of acyl chloride, solution after the reaction, individual fractions, and individual compounds. The core compounds are synthetic, semi synthetic or from natural source. The core compounds are including terpene, isoprene, triterpenes, and hydroxylated triterpenes.

MTT activity of acylation of core compounds in different reaction time period of (ASAP)5 sec, 1 min, 2 min, 5 min, 10 min, 30 min, 1 hr, 2 hr, 18 hr, 2 days or 3 days at 0 C, 25 C or 75 C temperature were studied. HPLC profiles of esterification products of core compound E4A with acyl halide, wherein the halide comprise chloride, bromide, fluoride and iodide, wherein the acyl halide comprise acyl chloride, wherein acyl chloride comprise tigloyl chloride, angeloyl chloride, acetyl chloride, crotonoyl chloride, 3,3-dimethylartyloyl chloride, senecioyl chloride, cinnamoyl chloride, pentenoyl chloride, hexanoyl chloride, benzoyl chloride, ethylbutyryl chloride, propionyl chloride, 2-propenoyl chloride, isobutyryl chloride, butyryl chloride, (2E)-2-pentenoyl chloride, 4-Pentenoyl chloride, 5-hexenoyl chloride, heptanoyl chloride, octanoyl chloride, nonanoyl chloride, decanoyl chloride, Lauroyl chloride, myristoyl chloride, oleoyl chloride show that the compounds vary in composition when the time or temperature of the reaction is changed. See example in FIGS. 1-12 and Experiments 1-29

The peaks, fractions and compounds are selected according to the activities of times studies and the changes of peaks. Selecting the HPLC fractions for isolation is according to the cytotoxic activity of the reaction product obtained at a specific time. The compounds having strong to weak activities are selected and isolated. Selecting the HPLC fractions for isolation may be according to the cytotoxic activity of times studies and the change of peaks. The anti cancer activities are the MTT studies of bone (U2OS), lung (H460), bladder (HTB-9), ovary (ES2), colon (HCT116), pancreas (Capan), ovary (OVCAR3), prostate (DU145), skin (SK-Mel-5), mouth (KB), kidney (A498), breast (MCF-7), liver (HepG2), brain (T98G), luekemia (K562), cervix (HeLa).

Esterification of core compound E4A with Tigloyl chloride and isolation of the compounds with HPLC give the following compounds: wherein Tig=Tigloyl

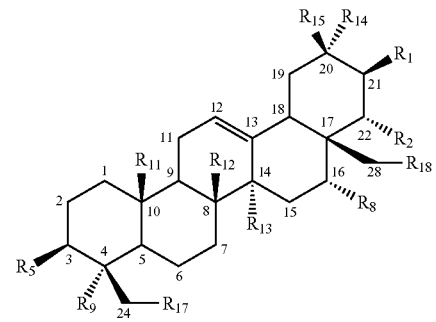

| | R1 | R2 | R5 | R8 | R17 | R18 | Cytotoxicity activity |
|---|---|---|---|---|---|---|---|
| E4A | OH | OH | OH | OH | OH | OH | none |
| A1 | OH | OH | OH | OH | O—Tig | OH | moderate |
| A2 | OH | OH | OH | OH | OH | O—Tig | moderate |
| A3 | OH | OH | OH | OH | O—Tig | O—Tig | strong |
| A4 | O—Tig | OH | OH | OH | O—Tig | O—Tig | moderate |
| A5 | OH | O—Tig | OH | OH | O—Tig | O—Tig | moderate |
| A6 | OH | OH | O—Tig | OH | O—Tig | O—Tig | moderate |
| A7 | OH | OH | OH | O—Tig | O—Tig | O—Tig | moderate |
| A8 | O—Tig | O—Tig | OH | OH | O—Tig | O—Tig | weak |
| A9 | OH | O—Tig | O—Tig | OH | O—Tig | O—Tig | weak |
| A10 | OH | OH | O—Tig | O—Tig | O—Tig | O—Tig | weak |
| A11 | O—Tig | OH | O—Tig | OH | O—Tig | O—Tig | weak |
| A12 | OH | O—Tig | OH | O—Tig | O—Tig | O—Tig | weak |
| A13 | O—Tig | OH | OH | O—Tig | O—Tig | O—Tig | weak |
| A14 | OH | O—Tig | O—Tig | OH | O—Tig | O—Tig | weak |
| A15 | O—Tig | O—Tig | O—Tig | OH | O—Tig | O—Tig | weak |
| A16 | O—Tig | O—Tig | OH | O—Tig | O—Tig | O—Tig | weak |
| A17 | O—Tig | OH | O—Tig | O—Tig | O—Tig | O—Tig | weak |
| A18 | OH | O—Tig | O—Tig | O—Tig | O—Tig | O—Tig | weak |
| A19 | O—Tig | O—Tig | O—Tig | O—Tig | O—Tig | O—Tig | none |
| A20 | O—Tig | O—Tig | OH | OH | OH | O—Tig | moderate |
| A21 | O—Tig | O—Tig | OH | OH | O—Tig | OH | moderate |
| A22 | O—Tig | O—Tig | OH | O—Tig | OH | OH | moderate |
| A23 | O—Tig | O—Tig | O—Tig | OH | OH | OH | moderate |
| A24 | O—Tig | O—Tig | OH | OH | OH | OH | moderate |
| A25 | O—Tig | OH | OH | OH | OH | O—Tig | moderate |
| A26 | OH | O—Tig | OH | OH | OH | O—Tig | moderate |
| A27 | OH | OH | O—Tig | OH | OH | O—Tig | moderate |
| A28 | OH | OH | OH | O—Tig | OH | O—Tig | moderate |
| A29 | O—Tig | OH | OH | OH | O—Tig | OH | moderate |
| A30 | OH | O—Tig | OH | OH | O—Tig | OH | moderate |
| A31 | OH | OH | O—Tig | OH | O—Tig | OH | moderate |
| A32 | OH | OH | OH | O—Tig | O—Tig | OH | moderate |

Esterification of core compound E4A with Angeloyl chloride and isolation of the compounds with HPLC give the following compounds: wherein Ang=Angeloyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| G1  | OH    | OH    | OH    | OH    | O-Ang | OH    | moderate              |
| G2  | OH    | OH    | OH    | OH    | OH    | O-Ang | moderate              |
| G3  | OH    | OH    | OH    | OH    | O-Ang | O-Ang | strong                |
| G4  | O-Ang | OH    | OH    | OH    | O-Ang | O-Ang | moderate              |
| G5  | OH    | O-Ang | OH    | OH    | O-Ang | O-Ang | moderate              |
| G6  | OH    | OH    | O-Ang | OH    | O-Ang | O-Ang | moderate              |
| G7  | OH    | OH    | OH    | O-Ang | O-Ang | O-Ang | moderate              |
| G8  | O-Ang | O-Ang | OH    | OH    | O-Ang | O-Ang | weak                  |
| G9  | OH    | O-Ang | O-Ang | OH    | O-Ang | O-Ang | weak                  |
| G10 | OH    | OH    | O-Ang | O-Ang | O-Ang | O-Ang | weak                  |
| G11 | O-Ang | OH    | O-Ang | OH    | O-Ang | O-Ang | weak                  |
| G12 | OH    | O-Ang | OH    | O-Ang | O-Ang | O-Ang | weak                  |
| G13 | O-Ang | OH    | OH    | O-Ang | O-Ang | O-Ang | weak                  |
| G14 | OH    | O-Ang | O-Ang | OH    | O-Ang | O-Ang | weak                  |
| G15 | O-Ang | O-Ang | O-Ang | OH    | O-Ang | O-Ang | weak                  |
| G16 | O-Ang | O-Ang | OH    | O-Ang | O-Ang | O-Ang | weak                  |
| G17 | O-Ang | OH    | O-Ang | O-Ang | O-Ang | O-Ang | weak                  |
| G18 | OH    | O-Ang | O-Ang | O-Ang | O-Ang | O-Ang | weak                  |
| G19 | O-Ang | O-Ang | O-Ang | O-Ang | O-Ang | O-Ang | none                  |
| G20 | O-Ang | O-Ang | OH    | OH    | OH    | O-Ang | moderate              |
| G21 | O-Ang | O-Ang | OH    | OH    | O-Ang | OH    | moderate              |
| G22 | O-Ang | O-Ang | OH    | O-Ang | OH    | OH    | moderate              |
| G23 | O-Ang | O-Ang | O-Ang | OH    | OH    | OH    | moderate              |
| G24 | O-Ang | O-Ang | OH    | OH    | OH    | OH    | moderate              |
| G25 | O-Ang | OH    | OH    | OH    | OH    | O-Ang | moderate              |
| G26 | OH    | O-Ang | OH    | OH    | OH    | O-Ang | moderate              |
| G27 | OH    | OH    | O-Ang | OH    | OH    | O-Ang | moderate              |
| G28 | OH    | OH    | OH    | O-Ang | OH    | O-Ang | moderate              |
| G29 | O-Ang | OH    | OH    | OH    | O-Ang | OH    | moderate              |
| G30 | OH    | O-Ang | OH    | OH    | O-Ang | OH    | moderate              |
| G31 | OH    | OH    | O-Ang | OH    | O-Ang | OH    | moderate              |
| G32 | OH    | OH    | OH    | O-Ang | O-Ang | OH    | moderate              |

Esterification of core compound E4A with (3,3-Dimethylartyloyl chloride) senecioyl chloride and isolation of the compounds with HPLC give the following compounds:

Wherein Sen=senecioyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| B1  | OH    | OH    | OH    | OH    | O-Sen | OH    | moderate              |
| B2  | OH    | OH    | OH    | OH    | OH    | O-Sen | moderate              |
| B3  | OH    | OH    | OH    | OH    | O-Sen | O-Sen | strong                |
| B4  | O-Sen | OH    | OH    | OH    | O-Sen | O-Sen | moderate              |
| B5  | OH    | O-Sen | OH    | OH    | O-Sen | O-Sen | moderate              |
| B6  | OH    | OH    | O-Sen | OH    | O-Sen | O-Sen | moderate              |
| B7  | OH    | OH    | OH    | O-Sen | O-Sen | O-Sen | moderate              |
| B8  | O-Sen | O-Sen | OH    | OH    | O-Sen | O-Sen | weak                  |
| B9  | OH    | O-Sen | O-Sen | OH    | O-Sen | O-Sen | weak                  |
| B10 | OH    | OH    | O-Sen | O-Sen | O-Sen | O-Sen | weak                  |
| B11 | O-Sen | OH    | O-Sen | OH    | O-Sen | O-Sen | weak                  |
| B12 | OH    | O-Sen | OH    | O-Sen | O-Sen | O-Sen | weak                  |
| B13 | O-Sen | OH    | OH    | O-Sen | O-Sen | O-Sen | weak                  |
| B14 | OH    | O-Sen | O-Sen | OH    | O-Sen | O-Sen | weak                  |
| B15 | O-Sen | O-Sen | O-Sen | OH    | O-Sen | O-Sen | weak                  |
| B16 | O-Sen | O-Sen | OH    | O-Sen | O-Sen | O-Sen | weak                  |
| B17 | O-Sen | OH    | O-Sen | O-Sen | O-Sen | O-Sen | weak                  |
| B18 | OH    | O-Sen | O-Sen | O-Sen | O-Sen | O-Sen | weak                  |
| B19 | O-Sen | O-Sen | O-Sen | O-Sen | O-Sen | O-Sen | none                  |
| B20 | O-Sen | O-Sen | OH    | OH    | OH    | O-Sen | moderate              |
| B21 | O-Sen | O-Sen | OH    | OH    | O-Sen | OH    | moderate              |
| B22 | O-Sen | O-Sen | OH    | O-Sen | OH    | OH    | moderate              |
| B23 | O-Sen | O-Sen | O-Sen | OH    | OH    | OH    | moderate              |
| B24 | O-Sen | O-Sen | OH    | OH    | OH    | OH    | moderate              |
| B25 | O-Sen | OH    | OH    | OH    | OH    | O-Sen | moderate              |
| B26 | OH    | O-Sen | OH    | OH    | OH    | O-Sen | moderate              |
| B27 | OH    | OH    | O-Sen | OH    | OH    | O-Sen | moderate              |
| B28 | OH    | OH    | OH    | O-Sen | OH    | O-Sen | moderate              |
| B29 | O-Sen | OH    | OH    | OH    | O-Sen | OH    | moderate              |
| B30 | OH    | O-Sen | OH    | OH    | O-Sen | OH    | moderate              |
| B31 | OH    | OH    | O-Sen | OH    | O-Sen | OH    | moderate              |
| B32 | OH    | OH    | OH    | O-Sen | O-Sen | OH    | moderate              |

Esterification of core compound E4A with 4-Pentenoyl chloride and isolation of the compounds with HPLC give the following compounds: wherein Pen=4-Pentenoyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| C1  | OH    | OH    | OH    | OH    | O-Pen | OH    | moderate              |
| C2  | OH    | OH    | OH    | OH    | OH    | O-Pen | moderate              |
| C3  | OH    | OH    | OH    | OH    | O-Pen | O-Pen | strong                |
| C4  | O-Pen | OH    | OH    | OH    | O-Pen | O-Pen | moderate              |
| C5  | OH    | O-Pen | OH    | OH    | O-Pen | O-Pen | moderate              |
| C6  | OH    | OH    | O-Pen | OH    | O-Pen | O-Pen | moderate              |
| C7  | OH    | OH    | OH    | O-Pen | O-Pen | O-Pen | moderate              |
| C8  | O-Pen | O-Pen | OH    | OH    | O-Pen | O-Pen | weak                  |
| C9  | OH    | O-Pen | O-Pen | OH    | O-Pen | O-Pen | weak                  |
| C10 | OH    | OH    | O-Pen | O-Pen | O-Pen | O-Pen | weak                  |
| C11 | O-Pen | OH    | O-Pen | OH    | O-Pen | O-Pen | weak                  |
| C12 | OH    | O-Pen | OH    | O-Pen | O-Pen | O-Pen | weak                  |
| C13 | O-Pen | OH    | OH    | O-Pen | O-Pen | O-Pen | weak                  |
| C14 | OH    | O-Pen | O-Pen | OH    | O-Pen | O-Pen | weak                  |
| C15 | O-Pen | O-Pen | O-Pen | OH    | O-Pen | O-Pen | weak                  |
| C16 | O-Pen | O-Pen | OH    | O-Pen | O-Pen | O-Pen | weak                  |
| C17 | O-Pen | OH    | O-Pen | O-Pen | O-Pen | O-Pen | weak                  |
| C18 | OH    | O-Pen | O-Pen | O-Pen | O-Pen | O-Pen | weak                  |
| C19 | O-Pen | O-Pen | O-Pen | O-Pen | O-Pen | O-Pen | none                  |
| C20 | O-Pen | O-Pen | OH    | OH    | OH    | O-Pen | moderate              |
| C21 | O-Pen | O-Pen | OH    | OH    | O-Pen | OH    | moderate              |
| C22 | O-Pen | O-Pen | OH    | O-Pen | OH    | OH    | moderate              |
| C23 | O-Pen | O-Pen | O-Pen | OH    | OH    | OH    | moderate              |
| C24 | O-Pen | O-Pen | OH    | OH    | OH    | OH    | moderate              |
| C25 | O-Pen | OH    | OH    | OH    | OH    | O-Pen | moderate              |
| C26 | OH    | O-Pen | OH    | OH    | OH    | O-Pen | moderate              |
| C27 | OH    | OH    | O-Pen | OH    | OH    | O-Pen | moderate              |
| C28 | OH    | OH    | OH    | O-Pen | OH    | O-Pen | moderate              |
| C29 | O-Pen | OH    | OH    | OH    | O-Pen | OH    | moderate              |
| C30 | OH    | O-Pen | OH    | OH    | O-Pen | OH    | moderate              |
| C31 | OH    | OH    | O-Pen | OH    | O-Pen | OH    | moderate              |
| C32 | OH    | OH    | OH    | O-Pen | O-Pen | OH    | moderate              |

Esterification of core compound E4A with Hexanoyl chloride and isolation of the compounds with HPLC give the following compounds: wherein Hex=Hexanoyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| D1  | OH    | OH    | OH    | OH    | O-Hex | OH    | moderate              |
| D2  | OH    | OH    | OH    | OH    | OH    | O-Hex | moderate              |
| D3  | OH    | OH    | OH    | OH    | O-Hex | O-Hex | strong                |
| D4  | O-Hex | OH    | OH    | OH    | O-Hex | O-Hex | moderate              |
| D5  | OH    | O-Hex | OH    | OH    | O-Hex | O-Hex | moderate              |
| D6  | OH    | OH    | O-Hex | OH    | O-Hex | O-Hex | moderate              |
| D7  | OH    | OH    | OH    | O-Hex | O-Hex | O-Hex | moderate              |
| D8  | O-Hex | O-Hex | OH    | OH    | O-Hex | O-Hex | weak                  |
| D9  | OH    | O-Hex | O-Hex | OH    | O-Hex | O-Hex | weak                  |
| D10 | OH    | OH    | O-Hex | O-Hex | O-Hex | O-Hex | weak                  |
| D11 | O-Hex | OH    | O-Hex | OH    | O-Hex | O-Hex | weak                  |
| D12 | OH    | O-Hex | OH    | O-Hex | O-Hex | O-Hex | weak                  |
| D13 | O-Hex | OH    | OH    | O-Hex | O-Hex | O-Hex | weak                  |
| D14 | OH    | O-Hex | O-Hex | OH    | O-Hex | O-Hex | weak                  |
| D15 | O-Hex | O-Hex | O-Hex | OH    | O-Hex | O-Hex | weak                  |
| D16 | O-Hex | O-Hex | OH    | O-Hex | O-Hex | O-Hex | weak                  |
| D17 | O-Hex | OH    | O-Hex | O-Hex | O-Hex | O-Hex | weak                  |
| D18 | OH    | O-Hex | O-Hex | O-Hex | O-Hex | O-Hex | weak                  |
| D19 | O-Hex | O-Hex | O-Hex | O-Hex | O-Hex | O-Hex | none                  |
| D20 | O-Hex | O-Hex | OH    | OH    | OH    | O-Hex | moderate              |
| D21 | O-Hex | O-Hex | OH    | OH    | O-Hex | OH    | moderate              |
| D22 | O-Hex | O-Hex | OH    | O-Hex | OH    | OH    | moderate              |
| D23 | O-Hex | O-Hex | O-Hex | OH    | OH    | OH    | moderate              |
| D24 | O-Hex | O-Hex | OH    | OH    | OH    | OH    | moderate              |
| D25 | O-Hex | OH    | OH    | OH    | OH    | O-Hex | moderate              |
| D26 | OH    | O-Hex | OH    | OH    | OH    | O-Hex | moderate              |
| D27 | OH    | OH    | O-Hex | OH    | OH    | O-Hex | moderate              |
| D28 | OH    | OH    | OH    | O-Hex | OH    | O-Hex | moderate              |
| D29 | O-Hex | OH    | OH    | OH    | O-Hex | OH    | moderate              |
| D30 | OH    | O-Hex | OH    | OH    | O-Hex | OH    | moderate              |

-continued

|     | R1  | R2  | R5    | R8    | R17   | R18 | Cytotoxicity activity |
|-----|-----|-----|-------|-------|-------|-----|-----------------------|
| D31 | OH  | OH  | O-Hex | OH    | O-Hex | OH  | moderate              |
| D32 | OH  | OH  | OH    | O-Hex | O-Hex | OH  | moderate              |

Esterification of core compound E4A with 2-Ethylbutyryl chloride and isolation of the compounds with HPLC give the following compounds: wherein Eth=2-Ethylbutyryl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| E1  | OH    | OH    | OH    | OH    | O-Eth | OH    | moderate              |
| E2  | OH    | OH    | OH    | OH    | OH    | O-Eth | moderate              |
| E3  | OH    | OH    | OH    | OH    | O-Eth | O-Eth | strong                |
| E4  | O-Eth | OH    | OH    | OH    | O-Eth | O-Eth | moderate              |
| E5  | OH    | O-Eth | OH    | OH    | O-Eth | O-Eth | moderate              |
| E6  | OH    | OH    | O-Eth | OH    | O-Eth | O-Eth | moderate              |
| E7  | OH    | OH    | OH    | O-Eth | O-Eth | O-Eth | moderate              |
| E8  | O-Eth | O-Eth | OH    | OH    | O-Eth | O-Eth | weak                  |
| E9  | OH    | O-Eth | O-Eth | OH    | O-Eth | O-Eth | weak                  |
| E10 | OH    | OH    | O-Eth | O-Eth | O-Eth | O-Eth | weak                  |
| E11 | O-Eth | OH    | O-Eth | OH    | O-Eth | O-Eth | weak                  |
| E12 | OH    | OH    | OH    | O-Eth | O-Eth | O-Eth | weak                  |
| E13 | O-Eth | OH    | OH    | O-Eth | O-Eth | O-Eth | weak                  |
| E14 | OH    | O-Eth | O-Eth | OH    | O-Eth | O-Eth | weak                  |
| E15 | O-Eth | O-Eth | O-Eth | OH    | O-Eth | O-Eth | weak                  |
| E16 | O-Eth | O-Eth | OH    | OH    | O-Eth | O-Eth | weak                  |
| E17 | O-Eth | OH    | O-Eth | O-Eth | O-Eth | O-Eth | weak                  |
| E18 | OH    | O-Eth | O-Eth | O-Eth | O-Eth | O-Eth | weak                  |
| E19 | O-Eth | O-Eth | O-Eth | O-Eth | O-Eth | O-Eth | none                  |
| E20 | O-Eth | O-Eth | OH    | OH    | OH    | O-Eth | moderate              |
| E21 | O-Eth | O-Eth | OH    | OH    | O-Eth | OH    | moderate              |
| E22 | O-Eth | O-Eth | OH    | O-Eth | OH    | OH    | moderate              |
| E23 | O-Eth | O-Eth | O-Eth | OH    | OH    | OH    | moderate              |
| E24 | O-Eth | O-Eth | OH    | OH    | OH    | OH    | moderate              |
| E25 | O-Eth | OH    | OH    | OH    | OH    | O-Eth | moderate              |
| E26 | OH    | O-Eth | OH    | OH    | OH    | O-Eth | moderate              |
| E27 | OH    | OH    | O-Eth | OH    | OH    | O-Eth | moderate              |
| E28 | OH    | OH    | OH    | O-Eth | OH    | O-Eth | moderate              |
| E29 | O-Eth | OH    | OH    | OH    | O-Eth | OH    | moderate              |
| E30 | OH    | O-Eth | OH    | OH    | O-Eth | OH    | moderate              |
| E31 | OH    | OH    | O-Eth | OH    | O-Eth | OH    | moderate              |
| E32 | OH    | OH    | OH    | O-Eth | O-Eth | OH    | moderate              |

Esterification of core compound E4A with Acetyl chloride (H) and isolation of the compounds with HPLC give the following compounds: wherein Acy=Acetyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| H1  | OH    | OH    | OH    | OH    | O-Acy | OH    | moderate              |
| H2  | OH    | OH    | OH    | OH    | OH    | O-Acy | moderate              |
| H3  | OH    | OH    | OH    | OH    | O-Acy | O-Acy | strong                |
| H4  | O-Acy | OH    | OH    | OH    | O-Acy | O-Acy | moderate              |
| H5  | OH    | O-Acy | OH    | OH    | O-Acy | O-Acy | moderate              |
| H6  | OH    | OH    | O-Acy | OH    | O-Acy | O-Acy | moderate              |
| H7  | OH    | OH    | OH    | O-Acy | O-Acy | O-Acy | moderate              |
| H8  | O-Acy | O-Acy | OH    | OH    | O-Acy | O-Acy | weak                  |
| H9  | OH    | O-Acy | O-Acy | OH    | O-Acy | O-Acy | weak                  |
| H10 | OH    | OH    | O-Acy | O-Acy | O-Acy | O-Acy | weak                  |
| H11 | O-Acy | OH    | O-Acy | OH    | O-Acy | O-Acy | weak                  |
| H12 | OH    | O-Acy | OH    | O-Acy | O-Acy | O-Acy | weak                  |
| H13 | O-Acy | OH    | OH    | O-Acy | O-Acy | O-Acy | weak                  |
| H14 | OH    | O-Acy | O-Acy | OH    | O-Acy | O-Acy | weak                  |
| H15 | O-Acy | O-Acy | O-Acy | OH    | O-Acy | O-Acy | weak                  |
| H16 | O-Acy | O-Acy | OH    | O-Acy | O-Acy | O-Acy | weak                  |
| H17 | O-Acy | OH    | O-Acy | O-Acy | O-Acy | O-Acy | weak                  |
| H18 | OH    | O-Acy | O-Acy | O-Acy | O-Acy | O-Acy | weak                  |
| H19 | O-Acy | O-Acy | O-Acy | O-Acy | O-Acy | O-Acy | none                  |
| H20 | O-Acy | O-Acy | OH    | OH    | OH    | O-Acy | moderate              |

-continued

|     | R1    | R2    | R5    | R8    | R17   | R18   | Cytotoxicity activity |
|-----|-------|-------|-------|-------|-------|-------|----------------------|
| H21 | O-Acy | O-Acy | OH    | OH    | O-Acy | OH    | moderate |
| H22 | O-Acy | O-Acy | OH    | O-Acy | OH    | OH    | moderate |
| H23 | O-Acy | O-Acy | O-Acy | OH    | OH    | OH    | moderate |
| H24 | O-Acy | O-Acy | OH    | OH    | OH    | OH    | moderate |
| H25 | O-Acy | OH    | OH    | OH    | OH    | O-Acy | moderate |
| H26 | OH    | O-Acy | OH    | OH    | OH    | O-Acy | moderate |
| H27 | OH    | OH    | O-Acy | OH    | OH    | O-Acy | moderate |
| H28 | OH    | OH    | OH    | O-Acy | OH    | O-Acy | moderate |
| H29 | O-Acy | OH    | OH    | OH    | O-Acy | OH    | moderate |
| H30 | OH    | O-Acy | OH    | OH    | O-Acy | OH    | moderate |
| H31 | OH    | OH    | O-Acy | OH    | O-Acy | OH    | moderate |
| H32 | OH    | OH    | OH    | O-Acy | O-Acy | OH    | moderate |

Esterification of core compound E4A with Crotonoyl chloride and isolation of the compounds with HPLC give the following compounds: wherein Cro=Crotonoyl

|      | R1    | R2    | R5    | R8    | R17   | R18   | Cytotoxicity activity |
|------|-------|-------|-------|-------|-------|-------|----------------------|
| E4A  | OH    | OH    | OH    | OH    | OH    | OH    | none |
| I1   | OH    | OH    | OH    | OH    | O-Cro | OH    | moderate |
| I2   | OH    | OH    | OH    | OH    | OH    | O-Cro | moderate |
| I3   | OH    | OH    | OH    | OH    | O-Cro | O-Cro | strong |
| I4   | O-Cro | OH    | OH    | OH    | O-Cro | O-Cro | moderate |
| I5   | OH    | O-Cro | OH    | OH    | O-Cro | O-Cro | moderate |
| I6   | OH    | OH    | O-Cro | OH    | O-Cro | O-Cro | moderate |
| I7   | OH    | OH    | OH    | O-Cro | O-Cro | O-Cro | moderate |
| I8   | O-Cro | O-Cro | OH    | OH    | O-Cro | O-Cro | weak |
| I9   | OH    | O-Cro | O-Cro | OH    | O-Cro | O-Cro | weak |
| I10  | OH    | OH    | O-Cro | O-Cro | O-Cro | O-Cro | weak |
| I11  | O-Cro | OH    | O-Cro | OH    | O-Cro | O-Cro | weak |
| I12  | OH    | O-Cro | OH    | O-Cro | O-Cro | O-Cro | weak |
| I13  | O-Cro | OH    | OH    | O-Cro | O-Cro | O-Cro | weak |
| I14  | OH    | O-Cro | O-Cro | OH    | O-Cro | O-Cro | weak |
| I15  | O-Cro | O-Cro | O-Cro | OH    | O-Cro | O-Cro | weak |
| I16  | O-Cro | O-Cro | OH    | O-Cro | O-Cro | O-Cro | weak |
| I17  | O-Cro | OH    | O-Cro | O-Cro | O-Cro | O-Cro | weak |
| I18  | OH    | O-Cro | O-Cro | O-Cro | O-Cro | O-Cro | weak |
| I19  | O-Cro | O-Cro | O-Cro | O-Cro | O-Cro | O-Cro | none |
| I20  | O-Cro | O-Cro | OH    | OH    | OH    | O-Cro | moderate |
| I21  | O-Cro | O-Cro | OH    | OH    | O-Cro | OH    | moderate |
| I22  | O-Cro | O-Cro | OH    | O-Cro | OH    | OH    | moderate |
| I23  | O-Cro | O-Cro | O-Cro | OH    | OH    | OH    | moderate |
| I24  | O-Cro | O-Cro | OH    | OH    | OH    | OH    | moderate |
| I25  | O-Cro | OH    | OH    | OH    | OH    | O-Cro | moderate |
| I26  | OH    | O-Cro | OH    | OH    | OH    | O-Cro | moderate |
| I27  | OH    | OH    | O-Cro | OH    | OH    | O-Cro | moderate |
| I28  | OH    | OH    | OH    | O-Cro | OH    | O-Cro | moderate |
| I29  | O-Cro | OH    | OH    | OH    | O-Cro | OH    | moderate |
| I30  | OH    | O-Cro | OH    | OH    | O-Cro | OH    | moderate |
| I31  | OH    | OH    | O-Cro | OH    | O-Cro | OH    | moderate |
| I32  | OH    | OH    | OH    | O-Cro | O-Cro | OH    | moderate |

Esterification of core compound E4A with Cinnamoyl chloride and isolation of the compounds with HPLC give the following compounds: wherein Cin=Cinnamoyl

|      | R1    | R2    | R5    | R8    | R17   | R18   | Cytotoxicity activity |
|------|-------|-------|-------|-------|-------|-------|----------------------|
| E4A  | OH    | OH    | OH    | OH    | OH    | OH    | none |
| J1   | OH    | OH    | OH    | OH    | O-Cin | OH    | moderate |
| J2   | OH    | OH    | OH    | OH    | OH    | O-Cin | moderate |
| J3   | OH    | OH    | OH    | OH    | O-Cin | O-Cin | strong |
| J4   | O-Cin | OH    | OH    | OH    | O-Cin | O-Cin | moderate |
| J5   | OH    | O-Cin | OH    | OH    | O-Cin | O-Cin | moderate |
| J6   | OH    | OH    | O-Cin | OH    | O-Cin | O-Cin | moderate |
| J7   | OH    | OH    | OH    | O-Cin | O-Cin | O-Cin | moderate |
| J8   | O-Cin | O-Cin | OH    | OH    | O-Cin | O-Cin | weak |
| J9   | OH    | O-Cin | O-Cin | OH    | O-Cin | O-Cin | weak |
| J10  | OH    | OH    | O-Cin | O-Cin | O-Cin | O-Cin | weak |

-continued

| | R1 | R2 | R5 | R8 | R17 | R18 | Cytotoxicity activity |
|---|---|---|---|---|---|---|---|
| J11 | O-Cin | OH | O-Cin | OH | O-Cin | O-Cin | weak |
| J12 | OH | O-Cin | OH | O-Cin | O-Cin | O-Cin | weak |
| J13 | O-Cin | OH | OH | O-Cin | O-Cin | O-Cin | weak |
| J14 | OH | O-Cin | O-Cin | OH | O-Cin | O-Cin | weak |
| J15 | O-Cin | O-Cin | O-Cin | OH | O-Cin | O-Cin | weak |
| J16 | O-Cin | O-Cin | OH | O-Cin | O-Cin | O-Cin | weak |
| J17 | O-Cin | OH | O-Cin | O-Cin | O-Cin | O-Cin | weak |
| J18 | OH | O-Cin | O-Cin | O-Cin | O-Cin | O-Cin | weak |
| J19 | O-Cin | O-Cin | O-Cin | O-Cin | O-Cin | O-Cin | none |
| J20 | O-Cin | O-Cin | OH | OH | OH | O-Cin | moderate |
| J21 | O-Cin | O-Cin | OH | OH | O-Cin | OH | moderate |
| J22 | O-Cin | O-Cin | OH | O-Cin | OH | OH | moderate |
| J23 | O-Cin | O-Cin | O-Cin | OH | OH | OH | moderate |
| J24 | O-Cin | O-Cin | OH | OH | OH | OH | moderate |
| J25 | O-Cin | OH | OH | OH | OH | O-Cin | moderate |
| J26 | OH | O-Cin | OH | OH | OH | O-Cin | moderate |
| J27 | OH | OH | O-Cin | OH | OH | O-Cin | moderate |
| J28 | OH | OH | OH | O-Cin | OH | O-Cin | moderate |
| J29 | O-Cin | OH | OH | OH | O-Cin | OH | moderate |
| J30 | OH | O-Cin | OH | OH | O-Cin | OH | moderate |
| J31 | OH | OH | O-Cin | OH | O-Cin | OH | moderate |
| J32 | OH | OH | OH | O-Cin | O-Cin | OH | moderate |

Esterification of core compound E4A with benzoyl chloride and isolation of the compounds with HPLC give the following compounds: wherein Ben=benzoyl

| | R1 | R2 | R5 | R8 | R17 | R18 | Cytotoxicity activity |
|---|---|---|---|---|---|---|---|
| E4A | OH | OH | OH | OH | OH | OH | None |
| K1 | OH | OH | OH | OH | O-Ben | OH | moderate |
| K2 | OH | OH | OH | OH | OH | O-Ben | moderate |
| K3 | OH | OH | OH | OH | O-Ben | O-Ben | strong |
| K4 | O-Ben | OH | OH | OH | O-Ben | O-Ben | moderate |
| K5 | OH | O-Ben | OH | OH | O-Ben | O-Ben | moderate |
| K6 | OH | OH | O-Ben | OH | O-Ben | O-Ben | moderate |
| K7 | OH | OH | OH | O-Ben | O-Ben | O-Ben | moderate |
| K8 | O-Ben | O-Ben | OH | OH | O-Ben | O-Ben | weak |
| K9 | OH | O-Ben | O-Ben | OH | O-Ben | O-Ben | weak |
| K10 | OH | OH | O-Ben | O-Ben | O-Ben | O-Ben | weak |
| K11 | O-Ben | OH | O-Ben | OH | O-Ben | O-Ben | weak |
| K12 | OH | O-Ben | OH | O-Ben | O-Ben | O-Ben | weak |
| K13 | O-Ben | OH | OH | O-Ben | O-Ben | O-Ben | weak |
| K14 | OH | O-Ben | O-Ben | OH | O-Ben | O-Ben | weak |
| K15 | O-Ben | O-Ben | O-Ben | OH | O-Ben | O-Ben | weak |
| K16 | O-Ben | O-Ben | OH | O-Ben | O-Ben | O-Ben | weak |
| K17 | O-Ben | OH | O-Ben | O-Ben | O-Ben | O-Ben | weak |
| K18 | OH | O-Ben | O-Ben | O-Ben | O-Ben | O-Ben | weak |
| K19 | O-Ben | O-Ben | O-Ben | O-Ben | O-Ben | O-Ben | none |
| K20 | O-Ben | O-Ben | OH | OH | OH | O-Ben | moderate |
| K21 | O-Ben | O-Ben | OH | OH | O-Ben | OH | moderate |
| K22 | O-Ben | O-Ben | OH | O-Ben | OH | OH | moderate |
| K23 | O-Ben | O-Ben | O-Ben | OH | OH | OH | moderate |
| K24 | O-Ben | O-Ben | OH | OH | OH | OH | moderate |
| K25 | O-Ben | OH | OH | OH | OH | O-Ben | moderate |
| K26 | OH | O-Ben | OH | OH | OH | O-Ben | moderate |
| K27 | OH | OH | O-Ben | OH | OH | O-Ben | moderate |
| K28 | OH | OH | OH | O-Ben | OH | O-Ben | moderate |
| K29 | O-Ben | OH | OH | OH | O-Ben | OH | moderate |
| K30 | OH | O-Ben | OH | OH | O-Ben | OH | moderate |
| K31 | OH | OH | O-Ben | OH | O-Ben | OH | moderate |
| K32 | OH | OH | OH | O-Ben | O-Ben | OH | moderate |

Esterification of core compound E4A with Propionyl chloride and isolation of the compounds with HPLC give the following compounds: wherein Ppi=Propionyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Ppi | OH | moderate |
| K2 | OH | OH | OH | OH | OH | O-Ppi | moderate |
| K3 | OH | OH | OH | OH | O-Ppi | O-Ppi | strong |
| K4 | O-Ppi | OH | OH | OH | O-Ppi | O-Ppi | moderate |
| K5 | OH | O-Ppi | OH | OH | O-Ppi | O-Ppi | moderate |

-continued

| | R1 | R2 | R5 | R8 | R17 | R18 | Cytotoxicity activity |
|---|---|---|---|---|---|---|---|
| K6 | OH | OH | O-Ppi | OH | O-Ppi | O-Ppi | moderate |
| K7 | OH | OH | OH | O-Ppi | O-Ppi | O-Ppi | moderate |
| K8 | O-Ppi | O-Ppi | OH | OH | O-Ppi | O-Ppi | weak |
| K9 | OH | O-Ppi | O-Ppi | OH | O-Ppi | O-Ppi | weak |
| K10 | OH | OH | O-Ppi | O-Ppi | O-Ppi | O-Ppi | weak |
| K11 | O-Ppi | OH | O-Ppi | OH | O-Ppi | O-Ppi | weak |
| K12 | OH | O-Ppi | OH | O-Ppi | O-Ppi | O-Ppi | weak |
| K13 | O-Ppi | OH | OH | O-Ppi | O-Ppi | O-Ppi | weak |
| K14 | OH | O-Ppi | O-Ppi | OH | O-Ppi | O-Ppi | weak |
| K15 | O-Ppi | O-Ppi | O-Ppi | OH | O-Ppi | O-Ppi | weak |
| K16 | O-Ppi | O-Ppi | OH | O-Ppi | O-Ppi | O-Ppi | weak |
| K17 | O-Ppi | OH | O-Ppi | O-Ppi | O-Ppi | O-Ppi | weak |
| K18 | OH | O-Ppi | O-Ppi | O-Ppi | O-Ppi | O-Ppi | weak |
| K19 | O-Ppi | O-Ppi | O-Ppi | O-Ppi | O-Ppi | O-Ppi | none |
| K20 | O-Ppi | O-Ppi | OH | OH | OH | O-Ppi | moderate |
| K21 | O-Ppi | O-Ppi | OH | OH | O-Ppi | OH | moderate |
| K22 | O-Ppi | O-Ppi | OH | O-Ppi | OH | OH | moderate |
| K23 | O-Ppi | O-Ppi | O-Ppi | OH | OH | OH | moderate |
| K24 | O-Ppi | O-Ppi | OH | OH | OH | OH | moderate |
| K25 | O-Ppi | OH | OH | OH | OH | O-Ppi | moderate |
| K26 | OH | O-Ppi | OH | OH | OH | O-Ppi | moderate |
| K27 | OH | OH | O-Ppi | OH | OH | O-Ppi | moderate |
| K28 | OH | OH | OH | O-Ppi | OH | O-Ppi | moderate |
| K29 | O-Ppi | OH | OH | OH | O-Ppi | OH | moderate |
| K30 | OH | O-Ppi | OH | OH | O-Ppi | OH | moderate |
| K31 | OH | OH | O-Ppi | OH | O-Ppi | OH | moderate |
| K32 | OH | OH | OH | O-Ppi | O-Ppi | OH | moderate |

Esterification of core compound E4A with 2-propenoyl chloride and isolation of the compounds with HPLC give the following compounds: wherein Ppe=Propenoyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Ppe | OH | moderate |
| K2 | OH | OH | OH | OH | OH | O-Ppe | moderate |
| K3 | OH | OH | OH | OH | O-Ppe | O-Ppe | strong |
| K4 | O-Ppe | OH | OH | OH | O-Ppe | O-Ppe | moderate |
| K5 | OH | O-Ppe | OH | OH | O-Ppe | O-Ppe | moderate |
| K6 | OH | OH | O-Ppe | OH | O-Ppe | O-Ppe | moderate |
| K7 | OH | OH | OH | O-Ppe | O-Ppe | O-Ppe | moderate |
| K8 | O-Ppe | O-Ppe | OH | OH | O-Ppe | O-Ppe | weak |
| K9 | OH | O-Ppe | O-Ppe | OH | O-Ppe | O-Ppe | weak |
| K10 | OH | OH | O-Ppe | O-Ppe | O-Ppe | O-Ppe | weak |
| K11 | O-Ppe | OH | O-Ppe | OH | O-Ppe | O-Ppe | weak |
| K12 | OH | O-Ppe | OH | O-Ppe | O-Ppe | O-Ppe | weak |
| K13 | O-Ppe | OH | OH | O-Ppe | O-Ppe | O-Ppe | weak |
| K14 | OH | O-Ppe | O-Ppe | OH | O-Ppe | O-Ppe | weak |
| K15 | O-Ppe | O-Ppe | O-Ppe | OH | O-Ppe | O-Ppe | weak |
| K16 | O-Ppe | O-Ppe | OH | O-Ppe | O-Ppe | O-Ppe | weak |
| K17 | O-Ppe | OH | O-Ppe | O-Ppe | O-Ppe | O-Ppe | weak |
| K18 | OH | O-Ppe | O-Ppe | O-Ppe | O-Ppe | O-Ppe | weak |
| K19 | O-Ppe | O-Ppe | O-Ppe | O-Ppe | O-Ppe | O-Ppe | none |
| K20 | O-Ppe | O-Ppe | OH | OH | OH | O-Ppe | moderate |
| K21 | O-Ppe | O-Ppe | OH | OH | O-Ppe | OH | moderate |
| K22 | O-Ppe | O-Ppe | OH | O-Ppe | OH | OH | moderate |
| K23 | O-Ppe | O-Ppe | O-Ppe | OH | OH | OH | moderate |
| K24 | O-Ppe | O-Ppe | OH | OH | OH | OH | moderate |
| K25 | O-Ppe | OH | OH | OH | OH | O-Ppe | moderate |
| K26 | OH | O-Ppe | OH | OH | OH | O-Ppe | moderate |
| K27 | OH | OH | O-Ppe | OH | OH | O-Ppe | moderate |
| K28 | OH | OH | OH | O-Ppe | OH | O-Ppe | moderate |
| K29 | O-Ppe | OH | OH | OH | O-Ppe | OH | moderate |
| K30 | OH | O-Ppe | OH | OH | O-Ppe | OH | moderate |
| K31 | OH | OH | O-Ppe | OH | O-Ppe | OH | moderate |
| K32 | OH | OH | OH | O-Ppe | O-Ppe | OH | moderate |

Esterification of core compound E4A with Isobutyryl chloride and isolation of the compounds with HPLC give the following compounds: wherein Iso=Isobutyryl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Iso | OH | moderate |
| K2 | OH | OH | OH | OH | OH | O-Iso | moderate |
| K3 | OH | OH | OH | OH | O-Iso | O-Iso | strong |
| K4 | O-Iso | OH | OH | OH | O-Iso | O-Iso | moderate |
| K5 | OH | O-Iso | OH | OH | O-Iso | O-Iso | moderate |
| K6 | OH | OH | O-Iso | OH | O-Iso | O-Iso | moderate |
| K7 | OH | OH | OH | O-Iso | O-Iso | O-Iso | moderate |
| K8 | O-Iso | O-Iso | OH | OH | O-Iso | O-Iso | weak |
| K9 | OH | O-Iso | O-Iso | OH | O-Iso | O-Iso | weak |
| K10 | OH | OH | O-Iso | O-Iso | O-Iso | O-Iso | weak |
| K11 | O-Iso | OH | O-Iso | OH | O-Iso | O-Iso | weak |
| K12 | OH | O-Iso | OH | O-Iso | O-Iso | O-Iso | weak |
| K13 | O-Iso | OH | OH | O-Iso | O-Iso | O-Iso | weak |
| K14 | OH | O-Iso | O-Iso | OH | O-Iso | O-Iso | weak |
| K15 | O-Iso | O-Iso | O-Iso | OH | O-Iso | O-Iso | weak |
| K16 | O-Iso | O-Iso | OH | O-Iso | O-Iso | O-Iso | weak |
| K17 | O-Iso | OH | O-Iso | O-Iso | O-Iso | O-Iso | weak |
| K18 | OH | O-Iso | O-Iso | O-Iso | O-Iso | O-Iso | weak |
| K19 | O-Iso | O-Iso | O-Iso | O-Iso | O-Iso | O-Iso | none |
| K20 | O-Iso | O-Iso | OH | OH | OH | O-Iso | moderate |
| K21 | O-Iso | O-Iso | OH | OH | O-Iso | OH | moderate |
| K22 | O-Iso | O-Iso | OH | O-Iso | OH | OH | moderate |
| K23 | O-Iso | O-Iso | O-Iso | OH | OH | OH | moderate |
| K24 | O-Iso | O-Iso | OH | OH | OH | OH | moderate |

|  | R1 | R2 | R5 | R8 | R17 | R18 | Cytotoxicity activity |
|---|---|---|---|---|---|---|---|
| K25 | O-Iso | OH | OH | OH | OH | O-Iso | moderate |
| K26 | OH | O-Iso | OH | OH | OH | O-Iso | moderate |
| K27 | OH | OH | O-Iso | OH | OH | O-Iso | moderate |
| K28 | OH | OH | OH | O-Iso | OH | O-Iso | moderate |
| K29 | O-Iso | OH | OH | OH | O-Iso | OH | moderate |
| K30 | OH | O-Iso | OH | OH | O-Iso | OH | moderate |
| K31 | OH | OH | O-Iso | OH | O-Iso | OH | moderate |
| K32 | OH | OH | OH | O-Iso | O-Iso | OH | moderate |

Esterification of core compound E4A with Butyryl chloride and isolation of the compounds with HPLC give the following compounds: wherein But=Butyryl

|  | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-But | OH | moderate |
| K2 | OH | OH | OH | OH | OH | O-But | moderate |
| K3 | OH | OH | OH | OH | O-But | O-But | strong |
| K4 | O-But | OH | OH | OH | O-But | O-But | moderate |
| K5 | OH | O-But | OH | OH | O-But | O-But | moderate |
| K6 | OH | OH | O-But | OH | O-But | O-But | moderate |
| K7 | OH | OH | OH | O-But | O-But | O-But | moderate |
| K8 | O-But | O-But | OH | OH | O-But | O-But | weak |
| K9 | OH | O-But | O-But | OH | O-But | O-But | weak |
| K10 | OH | OH | O-But | O-But | O-But | O-But | weak |
| K11 | O-But | OH | O-But | OH | O-But | O-But | weak |
| K12 | OH | O-But | OH | O-But | O-But | O-But | weak |
| K13 | O-But | OH | OH | O-But | O-But | O-But | weak |
| K14 | OH | O-But | O-But | OH | O-But | O-But | weak |
| K15 | O-But | O-But | O-But | OH | O-But | O-But | weak |
| K16 | O-But | O-But | OH | O-But | O-But | O-But | weak |
| K17 | O-But | OH | O-But | O-But | O-But | O-But | weak |
| K18 | OH | O-But | O-But | O-But | O-But | O-But | weak |
| K19 | O-But | O-But | O-But | O-But | O-But | O-But | none |
| K20 | O-But | O-But | OH | OH | OH | O-But | moderate |
| K21 | O-But | O-But | OH | OH | O-But | OH | moderate |
| K22 | O-But | O-But | OH | O-But | OH | OH | moderate |
| K23 | O-But | O-But | O-But | OH | OH | OH | moderate |
| K24 | O-But | O-But | OH | OH | OH | OH | moderate |
| K25 | O-But | OH | OH | OH | OH | O-But | moderate |
| K26 | OH | O-But | OH | OH | OH | O-But | moderate |
| K27 | OH | OH | O-But | OH | OH | O-But | moderate |
| K28 | OH | OH | OH | O-But | OH | O-But | moderate |
| K29 | O-But | OH | OH | OH | O-But | OH | moderate |
| K30 | OH | O-But | OH | OH | O-But | OH | moderate |
| K31 | OH | OH | O-But | OH | O-But | OH | moderate |
| K32 | OH | OH | OH | O-But | O-But | OH | moderate |

Esterification of core compound E4A with (2E)-2-pentenoyl chloride and isolation of the compounds with HPLC give the following compounds: wherein 2pe=2-pentenoyl

|  | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-2pe | OH | moderate |
| K2 | OH | OH | OH | OH | OH | O-2pe | moderate |
| K3 | OH | OH | OH | OH | O-2pe | O-2pe | strong |
| K4 | O-2pe | OH | OH | OH | O-2pe | O-2pe | moderate |
| K5 | OH | O-2pe | OH | OH | O-2pe | O-2pe | moderate |
| K6 | OH | OH | O-2pe | OH | O-2pe | O-2pe | moderate |
| K7 | OH | OH | OH | O-2pe | O-2pe | O-2pe | moderate |
| K8 | O-2pe | O-2pe | OH | OH | O-2pe | O-2pe | weak |
| K9 | OH | O-2pe | O-2pe | OH | O-2pe | O-2pe | weak |
| K10 | OH | OH | O-2pe | O-2pe | O-2pe | O-2pe | weak |
| K11 | O-2pe | OH | O-2pe | OH | O-2pe | O-2pe | weak |
| K12 | OH | O-2pe | OH | O-2pe | O-2pe | O-2pe | weak |
| K13 | O-2pe | OH | OH | O-2pe | O-2pe | O-2pe | weak |
| K14 | OH | O-2pe | O-2pe | OH | O-2pe | O-2pe | weak |
| K15 | O-2pe | O-2pe | O-2pe | OH | O-2pe | O-2pe | weak |
| K16 | O-2pe | O-2pe | OH | O-2pe | O-2pe | O-2pe | weak |
| K17 | O-2pe | OH | O-2pe | O-2pe | O-2pe | O-2pe | weak |
| K18 | OH | O-2pe | O-2pe | O-2pe | O-2pe | O-2pe | weak |
| K19 | O-2pe | O-2pe | O-2pe | O-2pe | O-2pe | O-2pe | none |
| K20 | O-2pe | O-2pe | OH | OH | OH | O-2pe | moderate |
| K21 | O-2pe | O-2pe | OH | OH | O-2pe | OH | moderate |

-continued

|     | R1    | R2    | R5    | R8    | R17   | R18   | Cytotoxicity activity |
|-----|-------|-------|-------|-------|-------|-------|----------------------|
| K22 | O-2pe | O-2pe | OH    | O-2pe | OH    | OH    | moderate |
| K23 | O-2pe | O-2pe | O-2pe | OH    | OH    | OH    | moderate |
| K24 | O-2pe | O-2pe | OH    | OH    | OH    | OH    | moderate |
| K25 | O-2pe | OH    | OH    | OH    | OH    | O-2pe | moderate |
| K26 | OH    | O-2pe | OH    | OH    | OH    | O-2pe | moderate |
| K27 | OH    | OH    | O-2pe | OH    | OH    | O-2pe | moderate |
| K28 | OH    | OH    | OH    | O-2pe | OH    | O-2pe | moderate |
| K29 | O-2pe | OH    | OH    | OH    | O-2pe | OH    | moderate |
| K30 | OH    | O-2pe | OH    | OH    | O-2pe | OH    | moderate |
| K31 | OH    | OH    | O-2pe | OH    | O-2pe | OH    | moderate |
| K32 | OH    | OH    | OH    | O-2pe | O-2pe | OH    | moderate |

Esterification of core compound E4A with Octanoyl chloride and isolation of the compounds with HPLC give the following compounds: wherein Oct=Octanoyl

|     | R1    | R2    | R5    | R8    | R17   | R18   | Cytotoxicity activity |
|-----|-------|-------|-------|-------|-------|-------|----------------------|
| E4A | OH    | OH    | OH    | OH    | OH    | OH    | none |
| K1  | OH    | OH    | OH    | OH    | O-Oct | OH    | moderate |
| K2  | OH    | OH    | OH    | OH    | OH    | O-Oct | moderate |
| K3  | OH    | OH    | OH    | OH    | O-Oct | O-Oct | strong |
| K4  | O-Oct | OH    | OH    | OH    | O-Oct | O-Oct | moderate |
| K5  | OH    | O-Oct | OH    | OH    | O-Oct | O-Oct | moderate |
| K6  | OH    | OH    | O-Oct | OH    | O-Oct | O-Oct | moderate |
| K7  | OH    | OH    | OH    | O-Oct | O-Oct | O-Oct | moderate |
| K8  | O-Oct | O-Oct | OH    | OH    | O-Oct | O-Oct | weak |
| K9  | OH    | O-Oct | O-Oct | OH    | O-Oct | O-Oct | weak |
| K10 | OH    | OH    | O-Oct | O-Oct | O-Oct | O-Oct | weak |
| K11 | O-Oct | OH    | O-Oct | OH    | O-Oct | O-Oct | weak |
| K12 | OH    | O-Oct | OH    | O-Oct | O-Oct | O-Oct | weak |
| K13 | O-Oct | OH    | OH    | O-Oct | O-Oct | O-Oct | weak |
| K14 | OH    | O-Oct | O-Oct | OH    | O-Oct | O-Oct | weak |
| K15 | O-Oct | O-Oct | O-Oct | OH    | O-Oct | O-Oct | weak |
| K16 | O-Oct | O-Oct | OH    | O-Oct | O-Oct | O-Oct | weak |
| K17 | O-Oct | OH    | O-Oct | O-Oct | O-Oct | O-Oct | weak |
| K18 | OH    | O-Oct | O-Oct | O-Oct | O-Oct | O-Oct | weak |
| K19 | O-Oct | O-Oct | O-Oct | O-Oct | O-Oct | O-Oct | none |
| K20 | O-Oct | O-Oct | OH    | OH    | OH    | O-Oct | moderate |
| K21 | O-Oct | O-Oct | OH    | OH    | O-Oct | OH    | moderate |
| K22 | O-Oct | O-Oct | OH    | O-Oct | OH    | OH    | moderate |
| K23 | O-Oct | O-Oct | O-Oct | OH    | OH    | OH    | moderate |
| K24 | O-Oct | O-Oct | OH    | OH    | OH    | OH    | moderate |
| K25 | O-Oct | OH    | OH    | OH    | OH    | O-Oct | moderate |
| K26 | OH    | O-Oct | OH    | OH    | OH    | O-Oct | moderate |
| K27 | OH    | OH    | O-Oct | OH    | OH    | O-Oct | moderate |
| K28 | OH    | OH    | OH    | O-Oct | OH    | O-Oct | moderate |
| K29 | O-Oct | OH    | OH    | OH    | O-Oct | OH    | moderate |
| K30 | OH    | O-Oct | OH    | OH    | O-Oct | OH    | moderate |
| K31 | OH    | OH    | O-Oct | OH    | O-Oct | OH    | moderate |
| K32 | OH    | OH    | OH    | O-Oct | O-Oct | OH    | moderate |

Esterification of core compound E4A with Decanoyl chloride and isolation of the compounds with HPLC give the following compounds: wherein Dec=Decanoyl

|     | R1    | R2    | R5    | R8    | R17   | R18   | Cytotoxicity activity |
|-----|-------|-------|-------|-------|-------|-------|----------------------|
| E4A | OH    | OH    | OH    | OH    | OH    | OH    | none |
| K1  | OH    | OH    | OH    | OH    | O-Dec | OH    | moderate |
| K2  | OH    | OH    | OH    | OH    | OH    | O-Dec | moderate |
| K3  | OH    | OH    | OH    | OH    | O-Dec | O-Dec | strong |
| K4  | O-Dec | OH    | OH    | OH    | O-Dec | O-Dec | moderate |
| K5  | OH    | O-Dec | OH    | OH    | O-Dec | O-Dec | moderate |
| K6  | OH    | OH    | O-Dec | OH    | O-Dec | O-Dec | moderate |
| K7  | OH    | OH    | OH    | O-Dec | O-Dec | O-Dec | moderate |
| K8  | O-Dec | O-Dec | OH    | OH    | O-Dec | O-Dec | weak |
| K9  | OH    | O-Dec | O-Dec | OH    | O-Dec | O-Dec | weak |
| K10 | OH    | OH    | O-Dec | O-Dec | O-Dec | O-Dec | weak |
| K11 | O-Dec | OH    | O-Dec | OH    | O-Dec | O-Dec | weak |

-continued

|  | R1 | R2 | R5 | R8 | R17 | R18 | Cytotoxicity activity |
|---|---|---|---|---|---|---|---|
| K12 | OH | O-Dec | OH | O-Dec | O-Dec | O-Dec | weak |
| K13 | O-Dec | OH | OH | O-Dec | O-Dec | O-Dec | weak |
| K14 | OH | O-Dec | O-Dec | OH | O-Dec | O-Dec | weak |
| K15 | O-Dec | O-Dec | O-Dec | OH | O-Dec | O-Dec | weak |
| K16 | O-Dec | O-Dec | OH | O-Dec | O-Dec | O-Dec | weak |
| K17 | O-Dec | OH | O-Dec | O-Dec | O-Dec | O-Dec | weak |
| K18 | OH | O-Dec | O-Dec | O-Dec | O-Dec | O-Dec | weak |
| K19 | O-Dec | O-Dec | O-Dec | O-Dec | O-Dec | O-Dec | none |
| K20 | O-Dec | O-Dec | OH | OH | OH | O-Dec | moderate |
| K21 | O-Dec | O-Dec | OH | OH | O-Dec | OH | moderate |
| K22 | O-Dec | O-Dec | OH | O-Dec | OH | OH | moderate |
| K23 | O-Dec | O-Dec | O-Dec | OH | OH | OH | moderate |
| K24 | O-Dec | O-Dec | OH | OH | OH | OH | moderate |
| K25 | O-Dec | OH | OH | OH | OH | O-Dec | moderate |
| K26 | OH | O-Dec | OH | OH | OH | O-Dec | moderate |
| K27 | OH | OH | O-Dec | OH | OH | O-Dec | moderate |
| K28 | OH | OH | OH | O-Dec | OH | O-Dec | moderate |
| K29 | O-Dec | OH | OH | OH | O-Dec | OH | moderate |
| K30 | OH | O-Dec | OH | OH | O-Dec | OH | moderate |
| K31 | OH | OH | O-Dec | OH | O-Dec | OH | moderate |
| K32 | OH | OH | OH | O-Dec | O-Dec | OH | moderate |

Esterification of core compound E4A with Myristoyl chloride and isolation of the compounds with HPLC give the following compounds: wherein Myr=Myristoyl

|  | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Myr | OH | moderate |
| K2 | OH | OH | OH | OH | OH | O-Myr | moderate |
| K3 | OH | OH | OH | OH | O-Myr | O-Myr | strong |
| K4 | O-Myr | OH | OH | OH | O-Myr | O-Myr | moderate |
| K5 | OH | O-Myr | OH | OH | O-Myr | O-Myr | moderate |
| K6 | OH | OH | O-Myr | OH | O-Myr | O-Myr | moderate |
| K7 | OH | OH | OH | O-Myr | O-Myr | O-Myr | moderate |
| K8 | O-Myr | O-Myr | OH | OH | O-Myr | O-Myr | weak |
| K9 | OH | O-Myr | O-Myr | OH | O-Myr | O-Myr | weak |
| K10 | OH | OH | O-Myr | O-Myr | O-Myr | O-Myr | weak |
| K11 | O-Myr | OH | O-Myr | OH | O-Myr | O-Myr | weak |
| K12 | OH | O-Myr | OH | O-Myr | O-Myr | O-Myr | weak |
| K13 | O-Myr | OH | OH | O-Myr | O-Myr | O-Myr | weak |
| K14 | OH | O-Myr | O-Myr | OH | O-Myr | O-Myr | weak |
| K15 | O-Myr | O-Myr | O-Myr | OH | O-Myr | O-Myr | weak |
| K16 | O-Myr | O-Myr | OH | O-Myr | O-Myr | O-Myr | weak |
| K17 | O-Myr | OH | O-Myr | O-Myr | O-Myr | O-Myr | weak |
| K18 | OH | O-Myr | O-Myr | O-Myr | O-Myr | O-Myr | weak |
| K19 | O-Myr | O-Myr | O-Myr | O-Myr | O-Myr | O-Myr | none |
| K20 | O-Myr | O-Myr | OH | OH | OH | O-Myr | moderate |
| K21 | O-Myr | O-Myr | OH | OH | O-Myr | OH | moderate |
| K22 | O-Myr | O-Myr | OH | O-Myr | OH | OH | moderate |
| K23 | O-Myr | O-Myr | O-Myr | OH | OH | OH | moderate |
| K24 | O-Myr | O-Myr | OH | OH | OH | OH | moderate |
| K25 | O-Myr | OH | OH | OH | OH | O-Myr | moderate |
| K26 | OH | O-Myr | OH | OH | OH | O-Myr | moderate |
| K27 | OH | OH | O-Myr | OH | OH | O-Myr | moderate |
| K28 | OH | OH | OH | O-Myr | OH | O-Myr | moderate |
| K29 | O-Myr | OH | OH | OH | O-Myr | OH | moderate |
| K30 | OH | O-Myr | OH | OH | O-Myr | OH | moderate |
| K31 | OH | OH | O-Myr | OH | O-Myr | OH | moderate |
| K32 | OH | OH | OH | O-Myr | O-Myr | OH | moderate |

Esterification of E4A-Tig-N with senecioyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Sen-1 | OH | OH | OH | OH | O-Tig | O-Sen | strong |

-continued

|          | R1    | R2    | R5    | R8  | R17   | R18   | Cytotoxicity activity |
|----------|-------|-------|-------|-----|-------|-------|----------------------|
| Tig-Sen-2 | O-Sen | OH    | OH    | OH  | O-Tig | O-Sen | moderate |
| Tig-Sen-3 | OH    | O-Sen | OH    | OH  | O-Tig | O-Sen | moderate |
| Tig-Sen-4 | OH    | OH    | O-Sen | OH  | O-Tig | O-Sen | moderate |
| Tig-Sen-5 | O-Sen | OH    | OH    | OH  | O-Tig | OH    | moderate |
| Tig-Sen-6 | OH    | O-Sen | OH    | OH  | O-Tig | OH    | moderate |

Esterification of E4A-Tig-N with Crotonoyl chloride and isolation of the compounds with HPLC give the following compounds:

|          | R1    | R2    | R5    | R8  | R17   | R18   | Cytotoxicity activity |
|----------|-------|-------|-------|-----|-------|-------|----------------------|
| E4A-Tig-N | OH    | OH    | OH    | OH  | O-Tig | OH    | moderate |
| Tig-Cro-1 | OH    | OH    | OH    | OH  | O-Tig | O-Cro | strong |
| Tig-Cro-2 | O-Cro | OH    | OH    | OH  | O-Tig | O-Cro | moderate |
| Tig-Cro-3 | OH    | O-Cro | OH    | OH  | O-Tig | O-Cro | moderate |
| Tig-Cro-4 | OH    | OH    | O-Cro | OH  | O-Tig | O-Cro | moderate |
| Tig-Cro-5 | O-Cro | OH    | OH    | OH  | O-Tig | OH    | moderate |
| Tig-Cro-6 | OH    | O-Cro | OH    | OH  | O-Tig | OH    | moderate |

Esterification of E4A-Tig-N with Acetyl chloride and isolation of the compounds with HPLC give the following compounds:

|          | R1    | R2    | R5    | R8  | R17   | R18   | Cytotoxicity activity |
|----------|-------|-------|-------|-----|-------|-------|----------------------|
| E4A-Tig-N | OH    | OH    | OH    | OH  | O-Tig | OH    | moderate |
| Tig-Acy-1 | OH    | OH    | OH    | OH  | O-Tig | O-Acy | strong |
| Tig-Acy-2 | O-Acy | OH    | OH    | OH  | O-Tig | O-Acy | moderate |
| Tig-Acy-3 | OH    | O-Acy | OH    | OH  | O-Tig | O-Acy | moderate |
| Tig-Acy-4 | OH    | OH    | O-Acy | OH  | O-Tig | O-Acy | moderate |
| Tig-Acy-5 | O-Acy | OH    | OH    | OH  | O-Tig | OH    | moderate |
| Tig-Acy-6 | OH    | O-Acy | OH    | OH  | O-Tig | OH    | moderate |

Esterification of E4A-Tig-N with 4-Pentenoyl chloride and isolation of the compounds with HPLC give the following compounds:

|          | R1    | R2    | R5    | R8    | R17   | R18   | Cytotoxicity activity |
|----------|-------|-------|-------|-------|-------|-------|----------------------|
| E4A-Tig-N | OH    | OH    | OH    | OH    | O-Tig | OH    | moderate |
| Tig-Pen-1 | OH    | OH    | OH    | OH    | O-Tig | O—Pen | strong |
| Tig-Pen-2 | O—Pen | OH    | OH    | OH    | O-Tig | O—Pen | moderate |
| Tig-Pen-3 | OH    | O—Pen | OH    | OH    | O-Tig | O—Pen | moderate |
| Tig-Pen-4 | OH    | OH    | O—Pen | OH    | O-Tig | O—Pen | moderate |
| Tig-Pen-5 | O—Pen | OH    | OH    | OH    | O-Tig | OH    | moderate |
| Tig-Pen-6 | OH    | O—Pen | OH    | OH    | O-Tig | OH    | moderate |

Esterification of E4A-Tig-N with Hexanoly chloride and isolation of the compounds with HPLC give the following compounds:

|          | R1    | R2    | R5    | R8    | R17   | R18   | Cytotoxicity activity |
|----------|-------|-------|-------|-------|-------|-------|----------------------|
| E4A-Tig-N | OH    | OH    | OH    | OH    | O-Tig | OH    | moderate |
| Tig-Hex-1 | OH    | OH    | OH    | OH    | O-Tig | O—Hex | strong |
| Tig-Hex-2 | O—Hex | OH    | OH    | OH    | O-Tig | O—Hex | moderate |
| Tig-Hex-3 | OH    | O—Hex | OH    | OH    | O-Tig | O—Hex | moderate |
| Tig-Hex-4 | OH    | OH    | O—Hex | OH    | O-Tig | O—Hex | moderate |
| Tig-Hex-5 | O—Hex | OH    | OH    | OH    | O-Tig | OH    | moderate |
| Tig-Hex-6 | OH    | O—Hex | OH    | OH    | O-Tig | OH    | moderate |

Esterification of E4A-Tig-N with Cinnamoyl chloride and isolation of the compounds with HPLC give the following compounds:

|           | R1    | R2    | R5    | R8  | R17   | R18   | Cytotoxicity activity |
|-----------|-------|-------|-------|-----|-------|-------|-----------------------|
| E4A-Tig-N | OH    | OH    | OH    | OH  | O-Tig | OH    | moderate              |
| Tig-Cin-1 | OH    | OH    | OH    | OH  | O-Tig | O-Cin | strong                |
| Tig-Cin-2 | O-Cin | OH    | OH    | OH  | O-Tig | O-Cin | moderate              |
| Tig-Cin-3 | OH    | O-Cin | OH    | OH  | O-Tig | O-Cin | moderate              |
| Tig-Cin-4 | OH    | OH    | O-Cin | OH  | O-Tig | O-Cin | moderate              |
| Tig-Cin-5 | O-Cin | OH    | OH    | OH  | O-Tig | OH    | moderate              |
| Tig-Cin-6 | OH    | O-Cin | OH    | OH  | O-Tig | OH    | moderate              |

Esterification of E4A-Tig-N with Angeloyl chloride and isolation of the compounds with HPLC give the following compounds:

|           | R1    | R2    | R5    | R8  | R17   | R18   | Cytotoxicity activity |
|-----------|-------|-------|-------|-----|-------|-------|-----------------------|
| E4A-Tig-N | OH    | OH    | OH    | OH  | O-Tig | OH    | moderate              |
| Tig-Ang-1 | OH    | OH    | OH    | OH  | O-Tig | O-Ang | strong                |
| Tig-Ang-2 | O-Ang | OH    | OH    | OH  | O-Tig | O-Ang | moderate              |
| Tig-Ang-3 | OH    | O-Ang | OH    | OH  | O-Tig | O-Ang | moderate              |
| Tig-Ang-4 | OH    | OH    | O-Ang | OH  | O-Tig | O-Ang | moderate              |
| Tig-Ang-5 | O-Ang | OH    | OH    | OH  | O-Tig | OH    | moderate              |
| Tig-Ang-6 | OH    | O-Ang | OH    | OH  | O-Tig | OH    | moderate              |

Esterification of E4A-Tig-N with 2-Ethylbutyryl chloride and isolation of the compounds with HPLC give the following compounds:

|           | R1    | R2    | R5    | R8  | R17   | R18   | Cytotoxicity activity |
|-----------|-------|-------|-------|-----|-------|-------|-----------------------|
| E4A-Tig-N | OH    | OH    | OH    | OH  | O-Tig | OH    | moderate              |
| Tig-Eth-1 | OH    | OH    | OH    | OH  | O-Tig | O-Eth | strong                |
| Tig-Eth-2 | O-Eth | OH    | OH    | OH  | O-Tig | O-Eth | moderate              |
| Tig-Eth-3 | OH    | O-Eth | OH    | OH  | O-Tig | O-Eth | moderate              |
| Tig-Eth-4 | OH    | OH    | O-Eth | OH  | O-Tig | O-Eth | moderate              |
| Tig-Eth-5 | O-Eth | OH    | OH    | OH  | O-Tig | OH    | moderate              |
| Tig-Eth-6 | OH    | O-Eth | OH    | OH  | O-Tig | OH    | moderate              |

Esterification of E4A-Tig-R with senecioyl chloride and isolation of the compounds with HPLC give the following compounds:

|             | R1    | R2    | R5    | R8  | R17   | R18   | Cytotoxicity activity |
|-------------|-------|-------|-------|-----|-------|-------|-----------------------|
| E4A-Tig-R   | OH    | OH    | OH    | OH  | O-Tig | O-Tig | strong                |
| Tig-R-Sen-1 | O-Sen | O-Sen | OH    | OH  | O-Tig | O-Tig | weak                  |
| Tig-R-Sen-2 | O-Sen | OH    | OH    | OH  | O-Tig | O-Tig | moderate              |
| Tig-R-Sen-3 | OH    | O-Sen | OH    | OH  | O-Tig | O-Tig | moderate              |
| Tig-R-Sen-4 | OH    | OH    | O-Sen | OH  | O-Tig | O-Tig | moderate              |
| Tig-R-Sen-5 | O-Sen | OH    | O-Sen | OH  | O-Tig | O-Tig | weak                  |
| Tig-R-Sen-6 | OH    | O-Sen | O-Sen | OH  | O-Tig | O-Tig | weak                  |

Esterification of E4A-Tig-R with Crotonoyl chloride and isolation of the compounds with HPLC give the following compounds:

|             | R1    | R2    | R5  | R8  | R17   | R18   | Cytotoxicity activity |
|-------------|-------|-------|-----|-----|-------|-------|-----------------------|
| E4A-Tig-R   | OH    | OH    | OH  | OH  | O-Tig | O-Tig | strong                |
| Tig-R-Cro-1 | O-Cro | O-Cro | OH  | OH  | O-Tig | O-Tig | weak                  |
| Tig-R-Cro-2 | O-Cro | OH    | OH  | OH  | O-Tig | O-Tig | moderate              |
| Tig-R-Cro-3 | OH    | O-Cro | OH  | OH  | O-Tig | O-Tig | moderate              |

-continued

|  | R1 | R2 | R5 | R8 | R17 | R18 | Cytotoxicity activity |
|---|---|---|---|---|---|---|---|
| Tig-R-Cro-4 | OH | OH | O-Cro | OH | O-Tig | O-Tig | moderate |
| Tig-R-Cro-5 | O-Cro | OH | O-Cro | OH | O-Tig | O-Tig | weak |
| Tig-R-Cro-6 | OH | O-Cro | O-Cro | OH | O-Tig | O-Tig | weak |

Esterification of E4A-Tig-R with Acetyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Acy-1 | O-Acy | O-Acy | OH | OH | O-Tig | O-Tig | weak |
| Tig-R-Acy-2 | O-Acy | OH | OH | OH | O-Tig | O-Tig | moderate |
| Tig-R-Acy-3 | OH | O-Acy | OH | OH | O-Tig | O-Tig | moderate |
| Tig-R-Acy-4 | OH | OH | O-Acy | OH | O-Tig | O-Tig | moderate |
| Tig-R-Acy-5 | O-Acy | OH | O-Acy | OH | O-Tig | O-Tig | weak |
| Tig-R-Acy-6 | OH | O-Acy | O-Acy | OH | O-Tig | O-Tig | weak |

Esterification of E4A-Tig-R with 4-Pentenoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Pen-1 | O—Pen | O—Pen | OH | OH | O-Tig | O-Tig | weak |
| Tig-R-Pen-2 | O—Pen | OH | OH | OH | O-Tig | O-Tig | moderate |
| Tig-R-Pen-3 | OH | O—Pen | OH | OH | O-Tig | O-Tig | moderate |
| Tig-R-Pen-4 | OH | OH | O—Pen | OH | O-Tig | O-Tig | moderate |
| Tig-R-Pen-5 | O—Pen | OH | O—Pen | OH | O-Tig | O-Tig | weak |
| Tig-R-Pen-6 | OH | O—Pen | O—Pen | OH | O-Tig | OH | weak |

Esterification of E4A-Tig-R with Hexanoly chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Hex-1 | O—Hex | O—Hex | OH | OH | O-Tig | O-Tig | weak |
| Tig-R-Hex-2 | O—Hex | OH | OH | OH | O-Tig | O-Tig | moderate |
| Tig-R-Hex-3 | OH | O—Hex | OH | OH | O-Tig | O-Tig | moderate |
| Tig-R-Hex-4 | OH | OH | O—Hex | OH | O-Tig | O-Tig | moderate |
| Tig-R-Hex-5 | O—Hex | OH | O—Hex | OH | O-Tig | O-Tig | weak |
| Tig-R-Hex-6 | OH | O—Hex | O—Hex | OH | O-Tig | O-Tig | weak |

Esterification of E4A-Tig-R with Cinnamoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Cin-1 | O-Cin | O-Cin | OH | OH | O-Tig | O-Tig | weak |
| Tig-R-Cin-2 | O-Cin | OH | OH | OH | O-Tig | O-Tig | moderate |
| Tig-R-Cin-3 | OH | O-Cin | OH | OH | O-Tig | O-Tig | moderate |
| Tig-R-Cin-4 | OH | OH | O-Cin | OH | O-Tig | O-Tig | moderate |
| Tig-R-Cin-5 | O-Cin | OH | O-Cin | OH | O-Tig | O-Tig | weak |
| Tig-R-Cin-6 | OH | O-Cin | O-Cin | OH | O-Tig | O-Tig | weak |

Esterification of E4A-Tig-R with Angeloyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Ang-1 | O-Ang | O-Ang | OH | OH | O-Tig | O-Tig | weak |
| Tig-R-Ang-2 | O-Ang | OH | OH | OH | O-Tig | O-Tig | moderate |
| Tig-R-Ang-3 | OH | O-Ang | OH | OH | O-Tig | O-Tig | moderate |
| Tig-R-Ang-4 | OH | OH | O-Ang | OH | O-Tig | O-Tig | moderate |
| Tig-R-Ang-5 | O-Ang | OH | O-Ang | OH | O-Tig | O-Tig | weak |
| Tig-R-Ang-6 | OH | O-Ang | O-Ang | OH | O-Tig | O-Tig | weak |

Esterification of E4A-Tig-R with 2-Ethylbutyryl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Eth-1 | O-Eth | O-Eth | OH | OH | O-Tig | O-Tig | weak |
| Tig-R-Eth-2 | O-Eth | OH | OH | OH | O-Tig | O-Tig | moderate |
| Tig-R-Eth-3 | OH | O-Eth | OH | OH | O-Tig | O-Tig | moderate |
| Tig-R-Eth-4 | OH | OH | O-Eth | OH | O-Tig | O-Tig | moderate |
| Tig-R-Eth-5 | O-Eth | OH | O-Eth | OH | O-Tig | O-Tig | weak |
| Tig-R-Eth-6 | OH | O-Eth | O-Eth | OH | O-Tig | O-Tig | weak |

Esterification of compound (A), (B), (C), (D1), (D2), (E), (F), (G), (H1), (H2), terpene, isoprene, triterpenes, hydroxylated triterpenes, with acyl halide, wherein the halide comprise chloride, bromide, fluoride and iodide, wherein the acyl halide comprise acyl chloride, wherein acyl chloride comprise tigloyl chloride, angeloyl chloride, acetyl chloride, crotonoyl chloride, 3,3-dimethylartyloyl chloride, senecioyl chloride, cinnamoyl chloride, pentenoyl chloride, hexanoyl chloride, benzoyl chloride, ethylbutyryl chloride, propionyl chloride, 2-propenoyl chloride, isobutyryl chloride, butyryl chloride, (2E)-2-pentenoyl chloride, 4-Pentenoyl chloride, 5-hexenoyl chloride, heptanoyl chloride, octanoyl chloride, nonanoyl chloride, decanoyl chloride, Lauroyl chloride, myristoyl chloride, oleoyl chloride. The compounds vary in composition when the time or temperature of the reaction is changed. The peaks, fractions and compounds are selected according to the activities of times studies and the changes of peaks. The compounds having strong to weak activities are selected and isolated. The anti cancer activities (Cytotoxic Assay) are the MTT studies of bone (U2OS), lung (H460), bladder (HTB-9), ovary (ES2), colon (HCT116), pancreas (Capan), ovary (OVCAR3), prostate (DU145), skin (SK-Mel-5), mouth (KB), kidney (A498), breast (MCF-7), liver (HepG2), brain (T98G), luekemia (K562), cervix (HeLa). The active esterification products are purified with HPLC. The reaction product of mixtures and individual compounds are tested with MTT Cytotoxic Assay. Details of method are in Experiment 3 of the present application. A second esterification of compound can be selected from the above experiment results to produce new active compounds. A partial esterification compound is selected from the above experiments to perform a second or repeated with a third esterification with different acyl chloride in order to produce new active compounds with the experiments in the present application.

A method is 1) Dissolving core compound or triterpenes core, hydroxylated triterpenes core, in pyridine; 2) Adding acyl halide or acyl chloride; 3, The mixture is stirred for length of time including 5 sec, 10 sec, 20 sec, 30 sec, 40 sec, 1 min, 2 min, 5 min, 10 min, 30 min, 1 hr, 2 hr, 18 hr, 2 days or 3 days at different temperature; 4) At the end of reaction, aqueous solution of acid or weak base, or water is added to the reaction mixture; 5) The solution is then extracted of ethyl acetate and ethyl acetate is removed by evaporation and lyophilization; 6) Dissolving the reaction product in acetonitrile with Trifluoroacetic acid or DMSO; 7) Testing the reaction product of mixtures and individual fractions with MTT cytotoxic assay; 8) Selecting the HPLC fractions for isolation is according to the cytotoxic activity of the reaction product obtained at a specific reaction time; 10) Purifiing the active esterification products with HPLC; 11) Collecting the products; 12) Testing the products; wherein the core compound is terpene, isoprene, or triterpene core or hydroxylated triterpenes core; wherein the core compound was dissolved in pyridine; wherein the acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride, Ethylbutyryl chloride, Propionyl chloride, 2-Propenoyl chloride, Isobutyryl chloride, Butyryl chloride, (2E)-2-pentenoyl chloride, 4-Pentenoyl chloride, 5-Hexenoyl chloride, Heptanoyl chloride, Octanoyl chloride, Nonanoyl chloride, Decanoyl chloride, Lauroyl chloride, Myristoyl chloride, and Oleoyl chloride; wherein the reaction time for the mixture is stirred for 5 sec, 10 sec, 20 sec, 30 sec, 40 sec, 1 min, 2 min, 5 min, 10 min, 30 min, 1 hr, 2 hr, 18 hr, 2 days or 3 days; wherein the temperature is 0 C, 25 C, 50 or 75 C temperature; wherein the acid including HCl or the base including NaHCO3 is added to the reaction mixture; wherein the solution is then extracted 3 times with ethyl acetate and lyophilization; wherein the reaction product is dissolved in 80% acetonitrile-0.005% Trifluoroacetic acid or DMSO; wherein selecting the HPLC fractions for isolation is according to the cytotoxic activity of the reaction product obtained at a reaction time of 5 sec, 10 sec, 20 sec, 30 sec, 40 sec, 1 min, 2 min, 5 min, 10 min, 30 min, 1 hr, 2 hr, 18 hr, 2 days or 3 days. In an embodiment, the reaction time may be ove 3 days. In an embodiment, the experiment may be performed under 0 C. In an embodiment, the experiment may be performed over 75 C.

The anti-cancer activities of Tig-R compound: IC50 of bone (U2OS) is 4.5 ug/ml, lung (H460) is 4.8 ug/ml, bladder (HTB-9) is 2.5 ug/ml, ovary (ES2) is 2.8 ug/ml, colon (HCT116) is 5.2 ug/ml, pancreas (Capan) 2.4 ug/ml, ovary (OVCAR3) is 5.8, prostate (DU145) is 3.6 ug/ml, skin (SK-Mel-5) is 5.1 ug/ml, mouth (KB) is 3 ug/ml, kidney (A498) is 3.5 ug/ml, breast (MCF-7) is 4.5 ug/ml, liver (HepG2) is 6 ug/ml, brain (T98G) is 8 ug/ml), leukemia (K562) is 2 ug/ml, cervix (HeLa) is 5 ug/ml.

The anti-cancer activities of Tig-V compound: IC50 of bone (U2OS) is 7 ug/ml, lung (H460) is 6.8 ug/ml, bladder (HTB-9) is 4 ug/ml, ovary (ES2) is 2 ug/ml, colon (HCT116) is 8 ug/ml, pancreas (Capan) 5 ug/ml, ovary (OVCAR3) is 9, prostate (DU145) is 4 ug/ml, skin (SK-Mel-5) is 6 ug/ml, mouth (KB) is 4.5 ug/ml, kidney (A498) is 4.8 ug/ml, breast (MCF-7) is 9 ug/ml, liver (HepG2) is 12 ug/ml, brain (T98G) is 14 ug/ml), leukemia (K562) is 4 ug/ml, cervix (HeLa) is 7 ug/ml.

The anti-cancer activities of Tig-N compound: IC50 of bone (U2OS) is 15 ug/ml, lung (H460) is 13 ug/ml, bladder (HTB-9) is 7.5 ug/ml, ovary (ES2) is 9 ug/ml, colon (HCT116) is 15 ug/ml, pancreas (Capan) 8 ug/ml, ovary (OVCAR3) is 18, prostate (DU145) is 4.8 ug/ml, skin (SK-Mel-5) is 15 ug/ml, mouth (KB) is 9 ug/ml, kidney (A498) is 11 ug/ml, breast (MCF-7) is 13 ug/ml, liver (HepG2) is 18 ug/ml, brain (T98G) is 19 ug/ml), leukemia (K562) is 6 ug/ml, cervix (HeLa) is 15 ug/ml.

The anti-cancer activities of Tig-Q compound: IC50 of bone (U2OS) is 20 ug/ml, lung (H460) is 18 ug/ml, bladder (HTB-9) is 10 ug/ml, ovary (ES2) is 12 ug/ml, colon (HCT116) is 22 ug/ml, pancreas (Capan) 9 ug/ml, ovary (OVCAR3) is 23, prostate (DU145) is 15 ug/ml, skin (SK-Mel-5) is 20 ug/ml, mouth (KB) is 12 ug/ml, kidney (A498) is 13 ug/ml, breast (MCF-7) is 18 ug/ml, liver (HepG2) is 24 ug/ml, brain (T98G) is 29 ug/ml), leukemia (K562) is 6 ug/ml, cervix (HeLa) is 20 ug/ml.

The anti-cancer activities of Tig-T compound: IC50 of bone (U2OS) is 20 ug/ml, lung (H460) is 21 ug/ml, bladder (HTB-9) is 12 ug/ml, ovary (ES2) is 14 ug/ml, colon (HCT116) is 23 ug/ml, pancreas (Capan) 10 ug/ml, ovary (OVCAR3) is 25, prostate (DU145) is 16 ug/ml, skin (SK-Mel-5) is 22 ug/ml, mouth (KB) is 13 ug/ml, kidney (A498) is 15 ug/ml, breast (MCF-7) is 20 ug/ml, liver (HepG2) is 26 ug/ml, brain (T98G) is 26 ug/ml), leukemia (K562) is 9 ug/ml, cervix (HeLa) is 18 ug/ml.

The anti-cancer activities of Tig-S compound: IC50 of bone (U2OS) is 5.2 ug/ml, lung (H460) is 5.6 ug/ml, bladder (HTB-9) is 3.5 ug/ml, ovary (ES2) is 0.1 ug/ml, colon (HCT116) is 6.6 ug/ml, pancreas (Capan) 2.9 ug/ml, ovary (OVCAR3) is 6.5, prostate (DU145) is 4.3 ug/ml, skin (SK-Mel-5) is 5.8 ug/ml, mouth (KB) is 4 ug/ml, kidney (A498) is 4.8 ug/ml, breast (MCF-7) is 6.3 ug/ml, liver (HepG2) is 8.5 ug/ml, brain (T98G) is 9 ug/ml), leukemia (K562) is 4.3 ug/ml, cervix (HeLa) is 7 ug/ml.

The anti-cancer activities of Tig-U compound: IC50 of bone (U2OS) is 23 ug/ml, lung (H460) is 19 ug/ml, bladder (HTB-9) is 15 ug/ml, ovary (ES2) is 17 ug/ml, colon (HCT116) is 26 ug/ml, pancreas (Capan) 9 ug/ml, ovary (OVCAR3) is 27, prostate (DU145) is 15 ug/ml, skin (SK-Mel-5) is 24 ug/ml, mouth (KB) is 16 ug/ml, kidney (A498) is 18 ug/ml, breast (MCF-7) is 25 ug/ml, liver (HepG2) is 23 ug/ml, brain (T98G) is 22 ug/ml), leukemia (K562) is 10 ug/ml, cervix (HeLa) is 17 ug/ml.

The IC50 of Tig-R in normal human fibroblast cells (WI38) is about 10-15 ug/ml. This I050 value is 3 times higher than those in ovary ES2 (2.8 ug/ml) and lung (H460) is 4.8 ug/ml.

Swiss3T3 cells are mouse normal fibroblast which were used in this experiment to compare with ES2 (human ovarian cancer) in Tig-R cytotoxicity determination. The preliminary results indicate that the IC50 of Tig-R in SW3T3 cells is above 20 ug/ml while the corresponding 1050 in ES2 cells is about 2.8 ug/ml.

This invention provides compounds, methods, or uses of a compound for the manufacture of a medicament, or uses of a compound for medicament selected from formula (2A), for treating cancer, inhibiting cancer growth, inhibiting cancer invasion, inhibiting cancer metastasis, modulating cell adhesion, modulating cell attachment, wherein the compounds with reduced heamolytic character/characteristic, using compounds selected from the following:

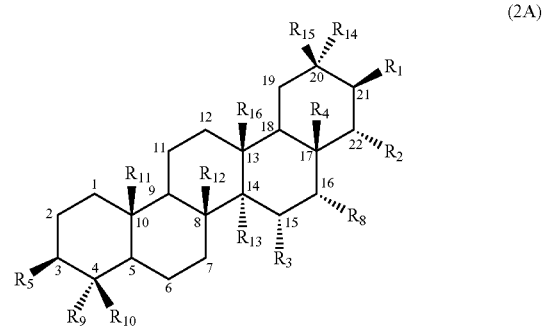

(2A)

R1, R2, R3, R4, R5, R8, R9, R10, R11, R12, R13, R14, R15 are independently selected from the group of hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C (2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O-C(2-18) Acyl, alkane, alkene and sugar moiety or derivatives thereof; or wherein the structure (2A) comprises at least 2 groups selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; or wherein R1 and R2 are selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; or wherein R4 and R10 are selected from CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O-C(2-18) Acyl. In an embodiment, wherein the R1 and R2 are attached OH. In an embodiment, wherein R4, R10 are attached a CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, or CH2O-Ethylbutyryl. In an embodiment, wherein the R3 and R8 is hydrogen or hydroxyl, In an embodiment, wherein the R9, R11, R12, R13, R14, R15 are independently attached with a methyl. In an embodiment, wherein R4 represents CH3, CHO, CH2R6 or CORE, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl and derivatives thereof; In an embodiment, wherein R3 is H or OH; In an embodiment, wherein R8 is H or OH; In an embodiment, wherein R16 is H, CH3, OH, or R4 and R16 may together form —CH2O—X—, CH(OH)—X— or C(=O)—X—, wherein the —X— may be O or NH or S; wherein when the C12-13 of ring 3 of the triterpene has a double bond then R16 is absent. In an embodiment, wherein R10 represents CH3, CHO, or CH2R6, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl and derivatives thereof; In an embodiment, wherein R5 is a hydrogen, hydroxyl, heterocyclic or O-sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof; wherein R9, R10, R11, R12, R13, R14, R15 are independently attached a group selecting from $CH_3$, $CH_2OH$, CHO, COOH, COO-alkyl, COO-aryl, COO-heterocyclic, COO-heteroaryl, $CH_2O$aryl, CH2O— heterocyclic, CH2O— heteroaryl, alkyls group, hydroxyl, acetyl group; wherein R4 and R16 form a divalent radical of formula CH2O, CH(OR7)O, or COOR7, wherein R7 is hydrogen, alkyl, angeloyl, tigloyl, senecioyl, dibenzoyl, benzoyl, alkanoyl, alkenoyl, benzoyl alkyl substituted alkanoyl, aryl, acyl, heterocylic, heteroraryl, and derivatives thereof; wherein at least two of R1, R2 and R6 are attached a group selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl and derivatives thereof; or at least one of R1, R2, and R4 is a sugar moiety having at least two groups selected from a group consisting of angeloyl, acetyl, tigloyl, senecioyl, Crotonoyl, 3,3-Dimethylartyloyl, Cinnamoyl, Pentenoyl, Hexanoyl, benzoyl, Ethylbutyryl, benzoyl, dibenzoyl, alkanoyl, alkenoyl, benzoyl alkyl substituted alkanoyl, aryl, acyl, heterocylic, heteroraryl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, O—C(2-18) Acyl and their derivatives thereof; or wherein R4 represents $CH_2R6$, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, In an embodiment, wherein R5 is a hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof. In an embodiment, R1, R2, R3, R4, R5, R8, R9, R10, R11, R12, R13, R14 or R15 comprise of one or more sugar moieties. In an embodiment, R1, R2, R3, R4, R5, R8, R9, R10, R11, R12, R13, R14 or R15 comprise of one or more acids. In an embodiment, at least 1, or 2, or 3, or 4 of R1, R2, R3, R4, R5, R8, R9, R10, R11, R12, R13, R14 and R15 is hydroxyl. In an embodiment, at least 2, or 3, or 4, or 5, or 6, or 7 of R1, R2, R3, R4, R5, R8, R9, R10, R11, R12, R13, R14 and R15 are independently attached a group selected from the group of O-acetyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, alkane, alkene and derivatives thereof, wherein the group is attached to the triterpene directly or by connecting moiety(ies); In an embodiment, at least 1 or 2, or 3, or 4, or 5, or 6, or 7 of R1, R2, R3, R4, R5, R8 and R10 are independently attached a group selected from the group of O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, $CH_3$, $CH_2OH$, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl and derivatives thereof, wherein the group is attached to the triterpene directly or by connecting moiety(ies). In an embodiment, the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer; wherein the cells comprise breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphhatic cell, pancreatic cell, stomach cell and thyroid cell. In an embodiment, the compound is selected from the structure:

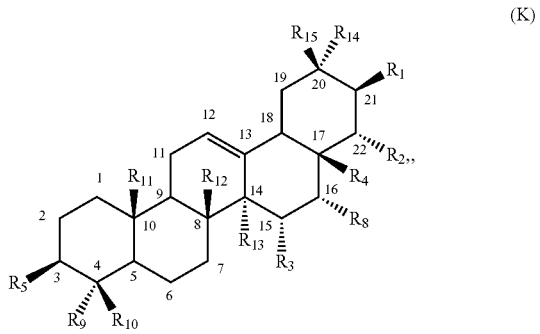

(K)

$R_1$, $R_2$, $R_3$, $R_4$, $R_5$, $R_8$, $R_9$, $R_{10}$, $R_{11}$, $R_{12}$, $R_{13}$, $R_{14}$, $R_{15}$ are independently selected from the group of CH3, CH2OH, COOH, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-alkane, O-alkene, O-sugar moiety, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-alkane, CH2O-alkene and CH2O-sugar moiety, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl, (CnH2n)O-angeloyl, (CnH2n)O-tigloyl, (CnH2n)O-senecioyl, (CnH2n)O-acetyl, (CnH2n)O-Crotonoyl, (CnH2n)O-3,3-Dimethylartyloyl, (CnH2n)O-Cinnamoyl, (CnH2n)O-Pentenoyl, (CnH2n)O-Hexanoyl, (CnH2n)O-benzoyl, (CnH2n)O-Ethylbutyryl, (CnH2n)O-alkyl, (CnH2n)O-dibenzoyl, (CnH2n)O-benzoyl, (CnH2n)O-alkanoyl, (CnH2n)O-alkenoyl, (CnH2n)O-benzoyl alkyl substituted O-alkanoyl, (CnH2n)O-alkanoyl substituted phenyl, (CnH2n)O-alkenoyl substituted phenyl, (CnH2n)O-aryl, (CnH2n)O-acyl, (CnH2n)O-heterocylic, (CnH2n)O-heteroraryl, (CnH2n)O-alkenylcarbonyl, (CnH2n)O-alkane, (CnH2n)O-alkene and (CnH2n)O-sugar moiety, wherein n is 1 or 2 or 3 or 4 or over 5 or derivatives thereof; or wherein any 1 or 2 or 3 or 4 of $R_1$, $R_2$, $R_3$, $R_4$, $R_5$, $R_8$ and $R_{10}$ are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, D-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein $R_9$, $R_{11}$, $R_{12}$, $R_{13}$, $R_{14}$, $R_{15}$ are independently attached a CH3; or wherein $R_{10}$ is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein R4 and/or R10 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; wherein R3 is OH or H or absent; wherein R1, R2, R3, R5, R8 are OH or H or absent; wherein R9, R11, R12, R13, R14, and R15 are CH3; or wherein R1, R2, R5, R8 represent OH; R3 represents OH, H or absent; or wherein R4, R10 represent CH2Oangeloyl; R9, R11, R12, R13, R14, R15 represent CH3; or wherein R1, R2, R5, R8 represent OH or O-tigloyl; R3 represents OH, H, or absent; or wherein R4, R10 represent CH2O tigloyl; R9, R11, R12, R13, R14, R15 represent CH3; wherein the group attaching to the core compound selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl are interchangeable; wherein the attached group can be the same group or in combination thereof; wherein the connecting group between the core compound and attached group may be O, S, S(O), S(O)$_2$, C(O), C(O)O, NH, N-alkyl, CH2 or CH2O. In an embodiment, R4 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl, In an embodiment, the connecting group between the functional group of angeloyl, tigloyl, senecioyl, acetyl, Crotonoyl, 3,3-Dimethylartyloyl, Cinnamoyl, Pentenoyl, Hexanoyl, benzoyl, Ethylbutyryl, alkyl, dibenzoyl, benzoyl, alkanoyl, alkenoyl, benzoyl alkyl substituted alkanoyl, alkanoyl substituted phenyl, alkenoyl substituted phenyl, aryl, acyl, heterocylic, heteroraryl, and alkenylcarbonyl ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl can be O, S, S(O), S(O)$_2$, C(O), C(O)O, NH, N-alkyl, CH2 or CH2O. In an embodiment, wherein any 1 or 2 or 3 or 4 or 5 or 6 of R1, R2, R3, R4, R5, R8, R9, R10, R11, R12, R13, R14, R15 are independently selected from the group of A-B, wherein A can be O, S, S(O), S(O)$_2$, C(O), C(O)O, NH, N-alkyl, CH2 or CH2O; wherein B is selected from the group of acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl and C(2-18) Acyl. In an enbodiment, R1 is A-B. In an enbodiment, R2 is A-B. In an enbodiment, R3 is A-B. In an enbodiment, R4 is A-B. In an enbodiment, R5 is A-B. In an enbodiment, R6 is A-B. In an enbodiment, R7 is A-B. In an enbodiment, R8 is A-B. In an enbodiment, R9 is A-B. In an enbodiment, R10 is A-B. In an enbodiment, R11 is A-B. In an enbodiment, R12 is A-B. In an enbodiment, R13 is A-B. In an enbodiment, R14 is A-B. In an enbodiment, R15 is A-B.

Liposome is artificially prepared vesicles which made up of a lipid bilayer. Certain sizes of liposome can enter tumour sites from blood due to the enhanced permeability and retention effect. While human blood vessels are all surrounded by endothelial cells bound by tight junctions, those tight junctions binding tumour vessels are leakier than those binding other vessels and thus liposomes are able to enter these vessels to enhance the delivery, efficacy, bioavailability and absorption of liposome enclosed drug. This invention provides methods to use liposomes or nanoparticles capsules as a carrier delivering the compound as medicament, wherein the size of liposomes or nanoparticles capsules is less than 200 nm or 100-200 nm or 50-100 nm or 5-50 nm or less than 50 nm, wherein the medicament is included but not limited for treating cancer, inhibiting cancer growth, inhibiting cancer invasion, inhibiting cancer metastasis, modulating cell adhesion, modulating cell attachment, wherein the compound is selected from formula (2A) or formula (K) at the above.

Substitution, deletion and/or addition of any group in the above-described compounds by other group(s) will be apparent to one of ordinary skill in the art based on the teachings of this application. In a further embodiment, the substitution, deletion and/or addition of the group(s) in the compound of the invention does not substantially affect the biological function of the compound is included in the invention.

In an embodiment, the compound is selected from the structures:

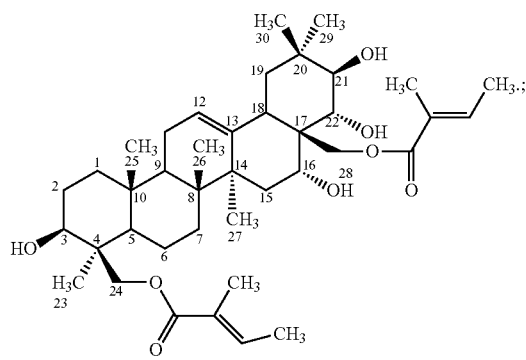

Compound E4A-Tig-R

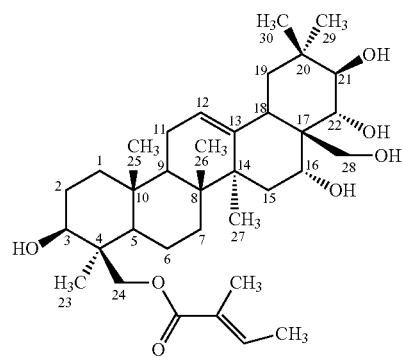

Compound E4A-Tig-N

-continued

Compound E4A-Tig-Q

Compound E4A-Tig-V

Compound E4A-Tig-T

Compound E4A-Tig-U

Compound E4A-Tig-S

Compound E4A-Ang-R

Compound E4A-Ang-V

Compound E4A-Ang-Q

Compound E4A-Ang-N
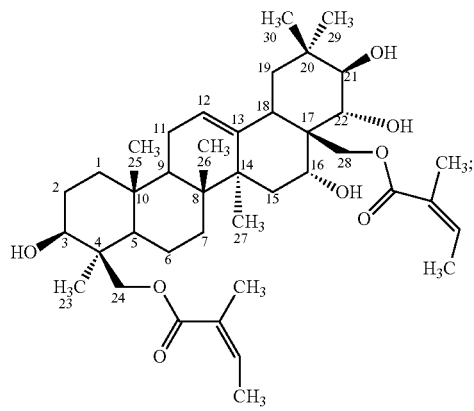
Compound E4A-Ang-T
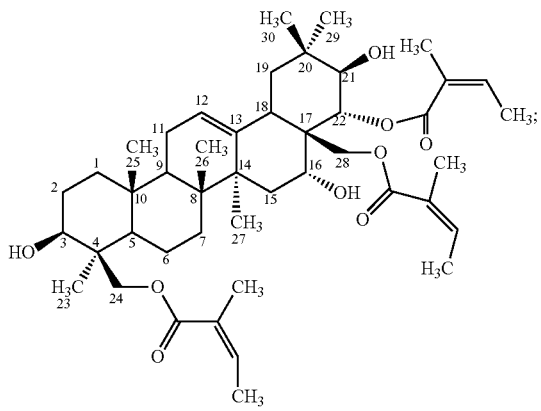
Compound E4A-Ang-U
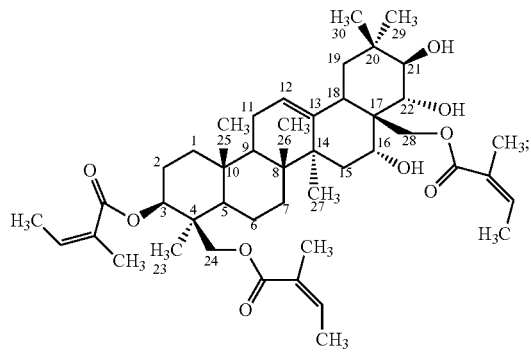
Compound E4A-Ang-S
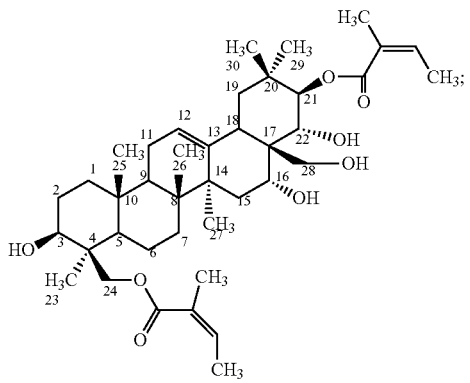
Compound E4A-Sen-R
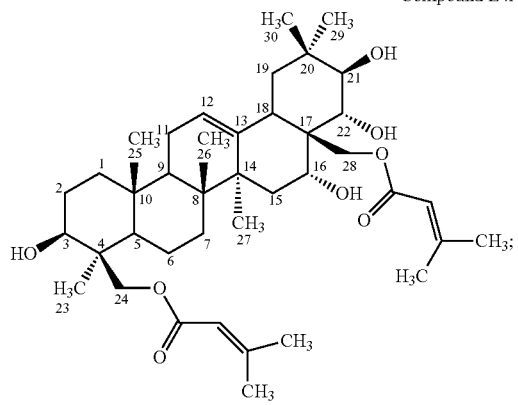
Compound E4A-Sen-V
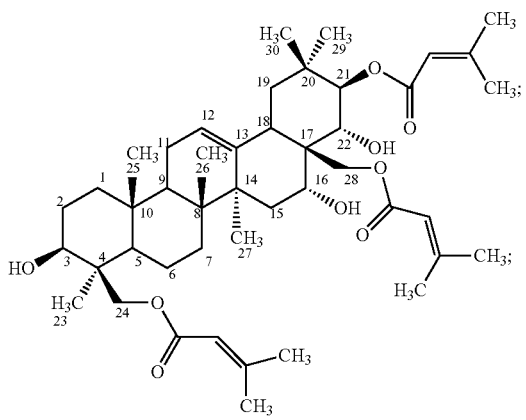

-continued
Compound E4A-Sen-N
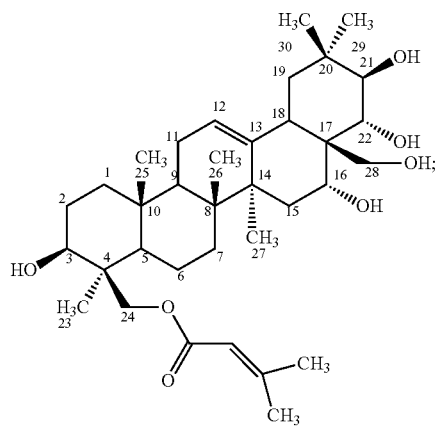
Compound E4A-Sen-Q
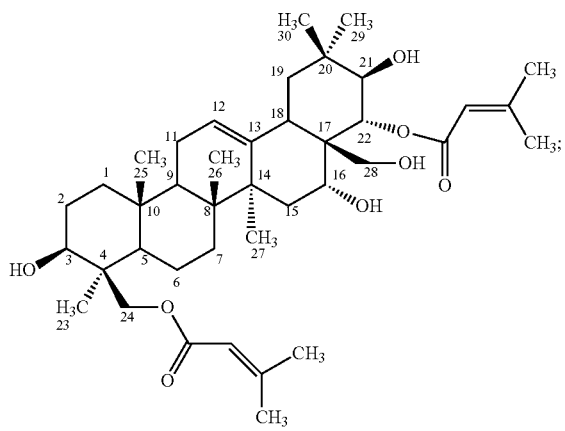
Compound E4A-Sen-S
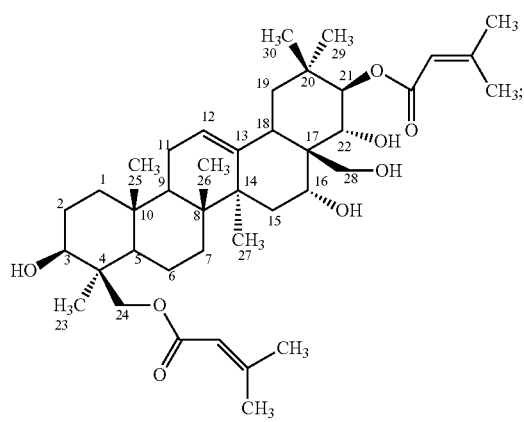
Compound E4A-Sen-T
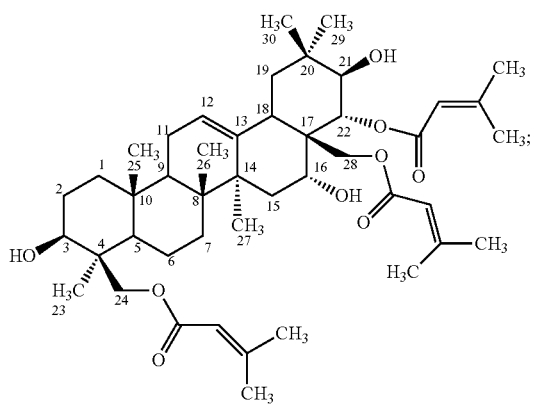
Compound E4A-Sen-U
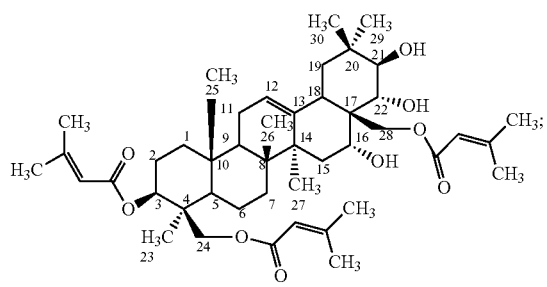
Compound E4A-Cro-R
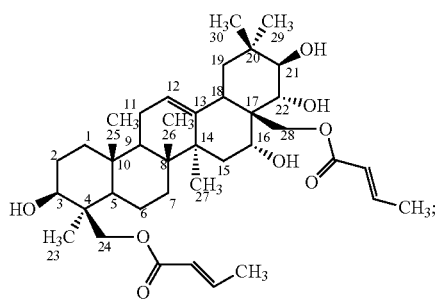
Compound E4A-Cro-V
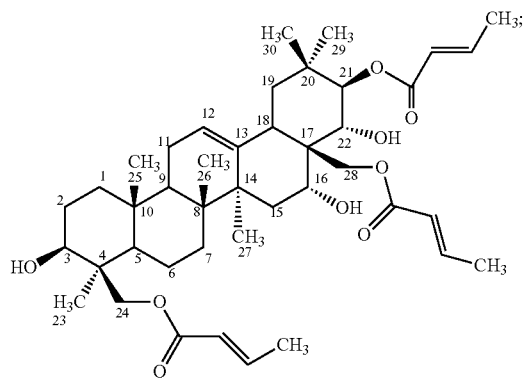
Compound E4A-Cro-N
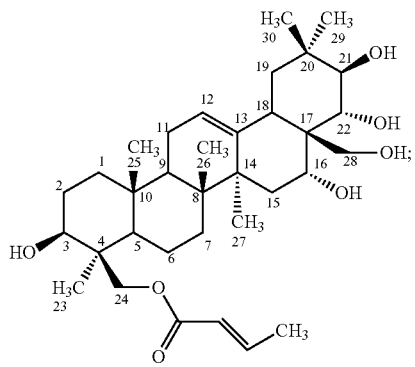

-continued
Compound E4A-Cro-Q
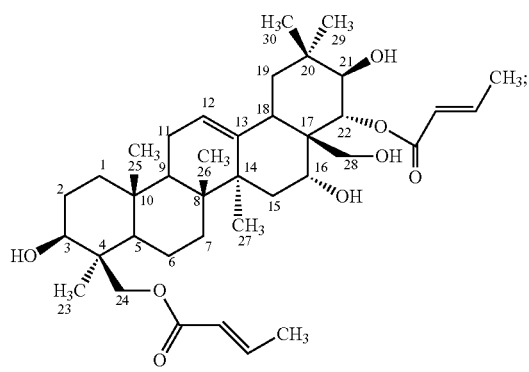
Compound E4A-Cro-S
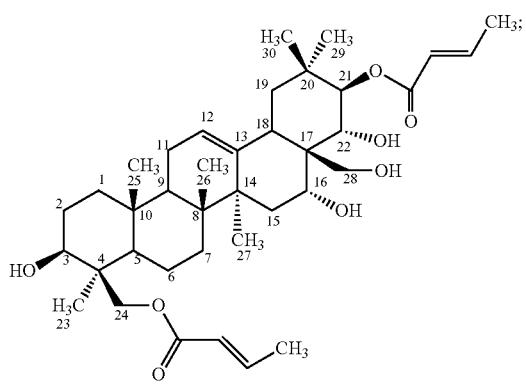
Compound E4A-Cro-T
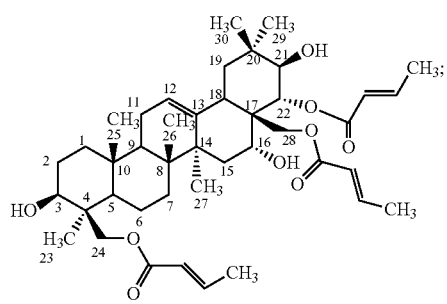
Compound E4A-Cro-U
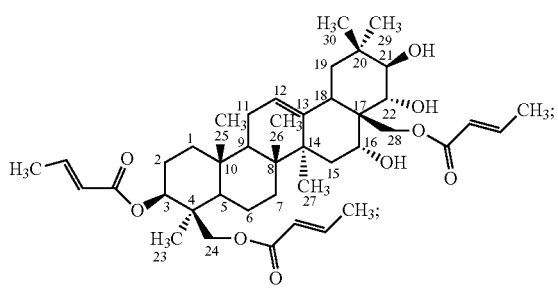
Compound E4A-Acy-R
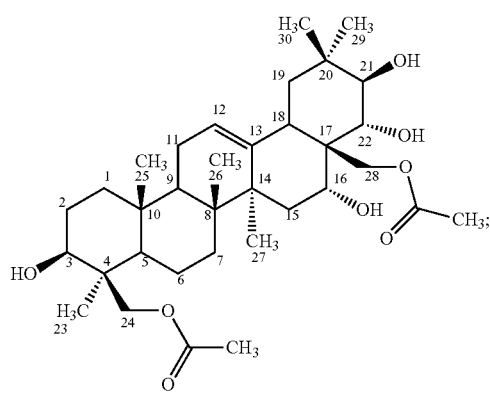
Compound E4A-Acy-V
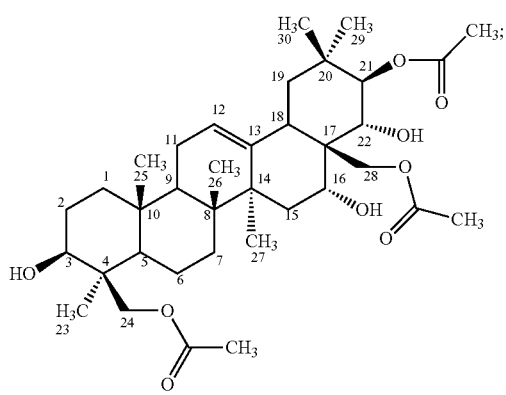
Compound E4A-Acy-N
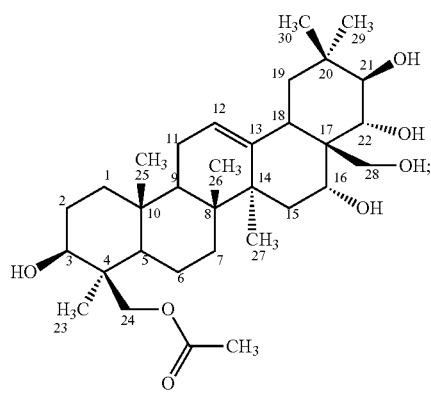
Compound E4A-Acy-Q
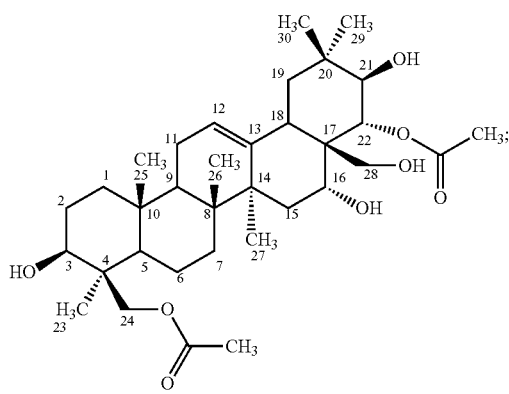

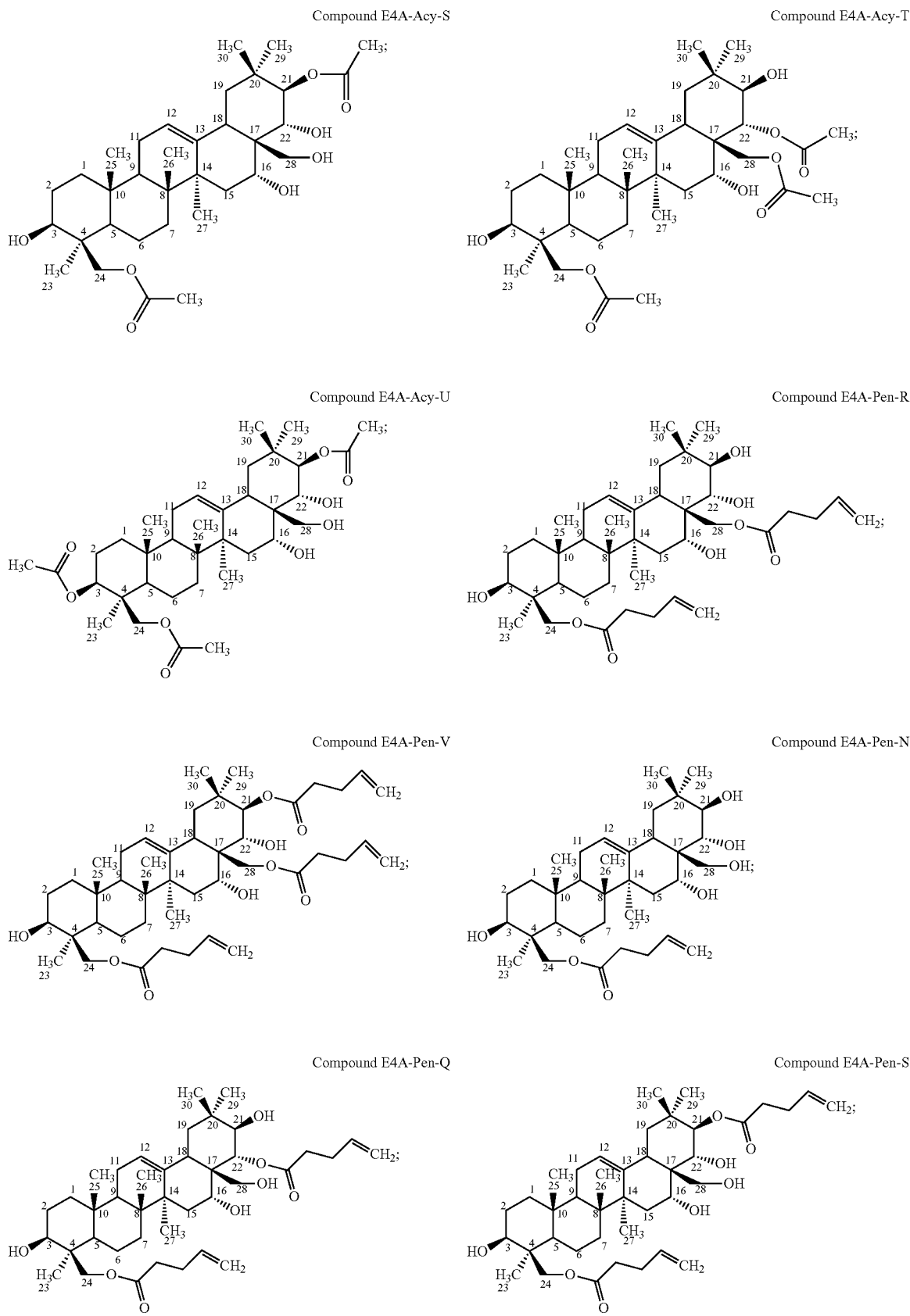

-continued
Compound E4A-Pen-T
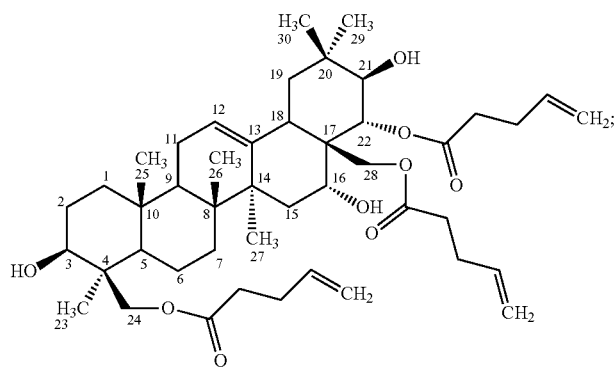
Compound E4A-Pen-U
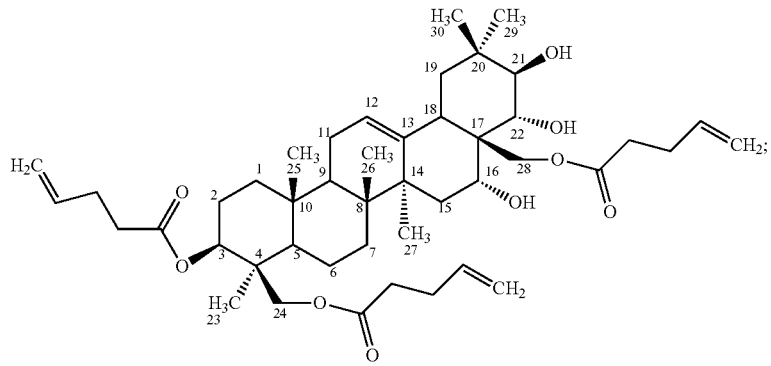
Compound E4A-Cin-R
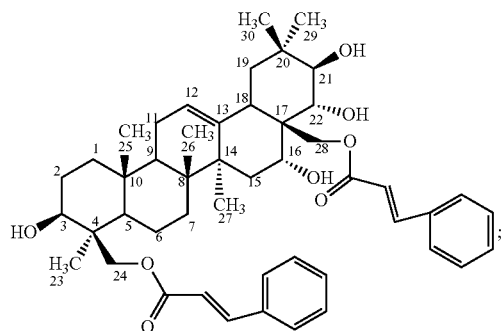
Compound E4A-Cin-V
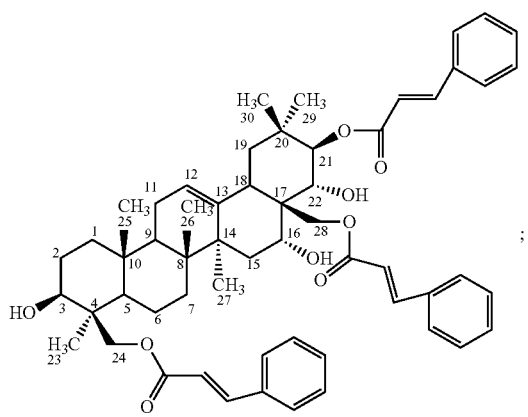
Compound E4A-Cin-N
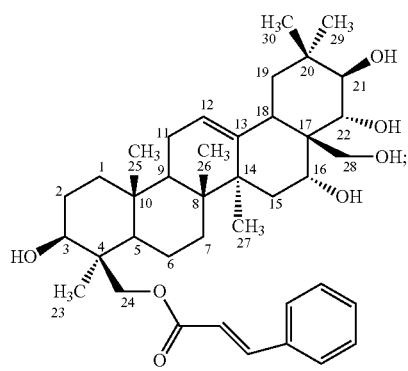
Compound E4A-Cin-Q
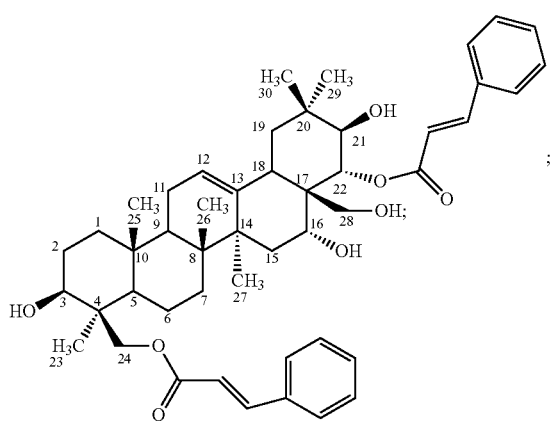

-continued
Compound E4A-Cin-S
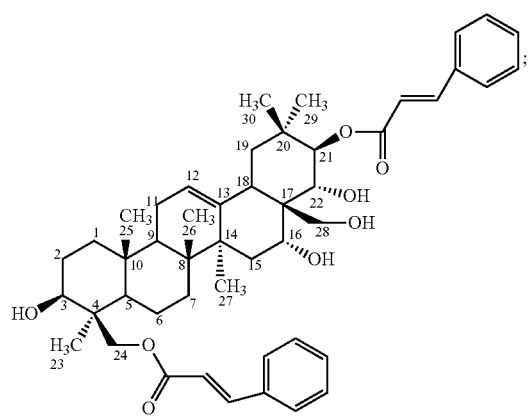
Compound E4A-Cin-T
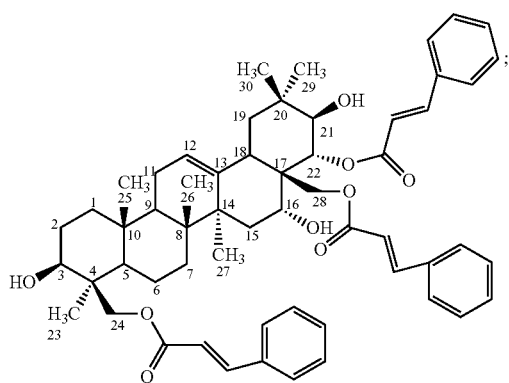
Compound E4A-Cin-U
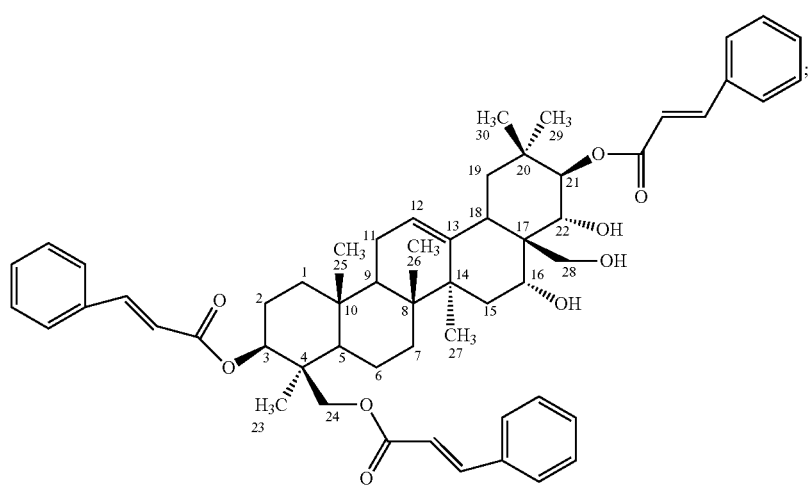
Tig-Sen-1
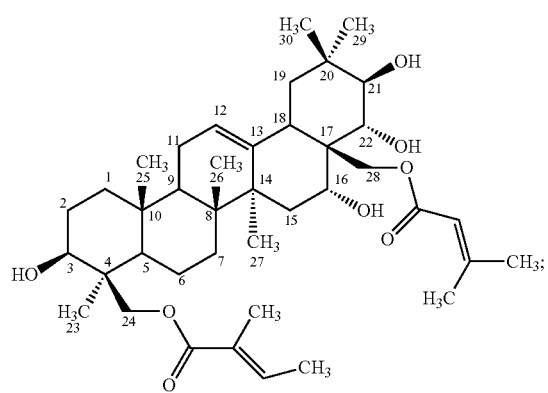
Tig-Cro-1
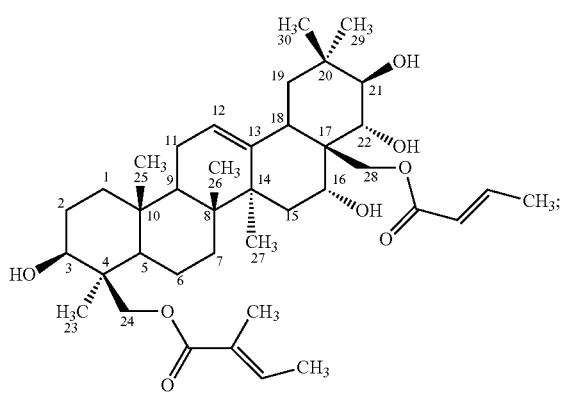
Tig-Ang-1
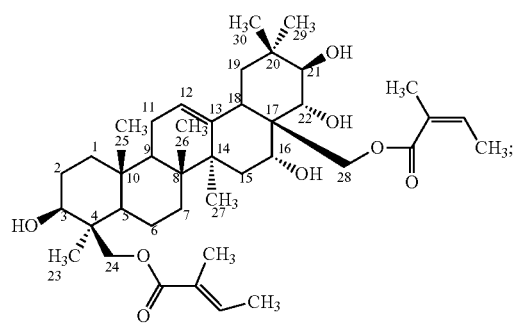
Tig-Pen-1
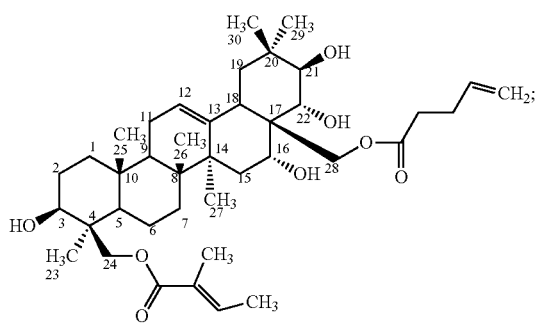

Tig-Acy-1

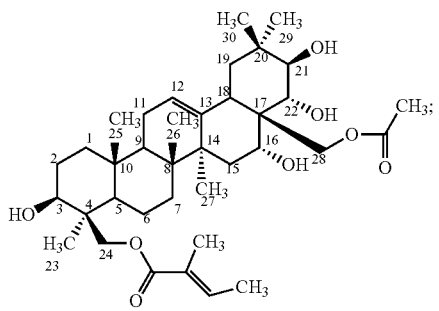

Tig-Hex-1

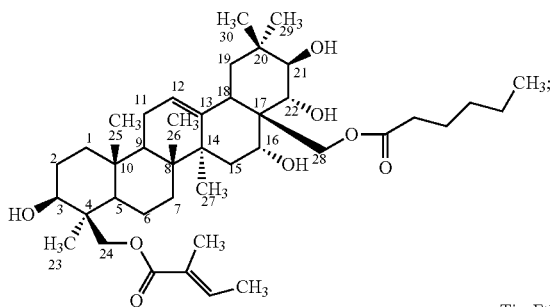

Tig-Eth-1

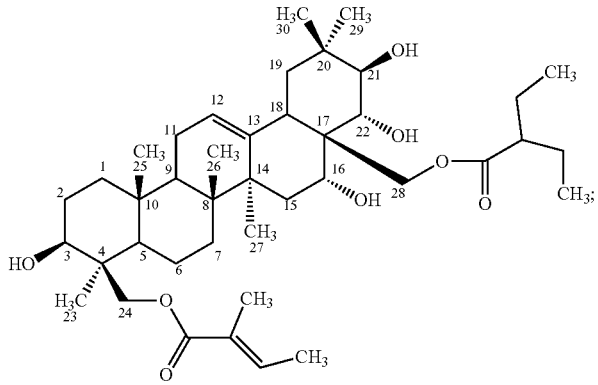

This invention provides compounds by esterification of core compound (C) or (D1) with acetyl chloride, angeloyl chloride, tigloyl chloride, senecioyl chloride, Crotonoyl chloride, O-3,3-Dimethylartyloyl chloride, Cinnamoyl chloride, Pentenoyl chloride, Hexanoyl chloride, benzoyl chloride, Ethylbutyryl chloride, and isolation of the compounds with HPLC, for treating cancer, inhibiting cancer growth, inhibiting cancer invasion, inhibiting cancer metastasis, modulating cell adhesion, modulating cell attachment, wherein the core compound selected from the following:

(C)

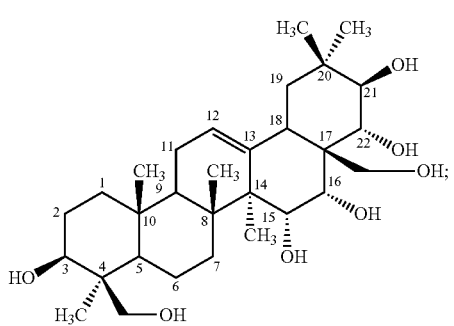

(A)

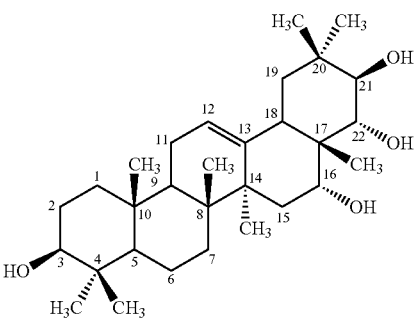

Esterification of compounds (A), (C), or (D1) with acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride, Ethylbutyryl chloride, ethanoyl chloride, propanoyl chloride, propenoyl chloride, butanoyl chloride, butenoyl chloride, pentanoyl chloride, hexenoyl chloride, heptanoyl chloride, heptenoyl chloride, octanoyl chloride, octenoyl chloride, nonanoyl chloride, nonenoyl chloride, decanoyl chloride, decenoyl chloride, propionyl chloride, 2-propenoyl chloride, 2-butenoyl chloride, Isobutyryl chloride, 2-methylpropanoyl chloride, 2-ethylbutyryl chloride, ethylbutanoyl chloride, 2-ethylbutanoyl chloride, butyryl chloride, (E)-2,3-Dimethylacryloyl chloride, (E)-2-Methylcrotonoyl chloride, 3-cis-Methyl-methacryloyl chloride, 3-Methyl-2-butenoyl chloride, 3-Methylcrotonoyl chloride, 4-Pentenoyl chloride, (2E)-2-pentenoyl chloride, Caproyl chloride, 5-Hexenoyl chloride, Capryloyl chloride, Lauroyl chloride, Dodecanoyl chloride, Myristoyl chloride, Tetradecanoyl chloride, Oleoyl chloride, C(2-18) Acyl chloride, The compounds vary in composition when the time or temperature of the reaction is changed. The peaks, fractions and compounds are selected according to the activities of times studies and the changes of peaks. The compounds having strong to weak activities are selected and isolated. The anti cancer activities are the MTT studies of bone (U2OS), lung (H460), bladder (HTB-9), ovary (ES2), colon (HCT116), ovary (OVCAR3), pancreas (Capan), prostate (DU145), skin (SK-Mel-5), mouth (KB), kidney (A498), breast (MCF-7), liver (HepG2), brain (T98G), luekemia (K562), cervix (HeLa). The active esterification products are purified with HPLC. The reaction product of mixtures and individual compounds are tested with MTT Cytotoxic Assay. Details of method are in Experiment 3 of the present application. A second esterification of compound can be selected from the above experiment results to produce new active compounds. A partial esterification compound is selected from the above experiments to perform a second or repeated with a third esterification with different acyl chloride in order to produce new active compounds with the experiments in the present application, wherein the compound can be selected from K, (H1) or (H2):

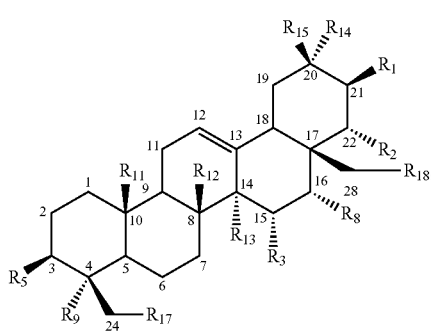
(H1)

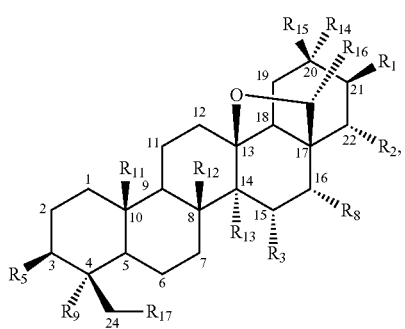
(H2)

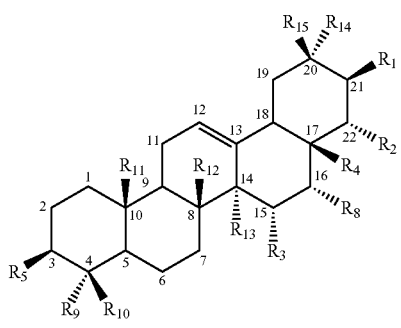
(K)

R1, R2, R3, R4, R5, R8, R9, R10, R11, R12, R13, R14, R15, R16, R17, R18 are independently selected from the group of CH3, CH2OH, COOH, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-alkane, O-alkene, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C (2-18) Acyl; or wherein any 1 or 2 or 3 or 4 of R1, R2, R3, R4, R5, R8, R10, R16, R17, R18 is/are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, D-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; R9, R11, R12, R13, R14, R15 are independently attached a CH3; or wherein R10 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein R4 and R10 are independently attached an O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein R17 and R18 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; wherein R3 is OH or H or absent; wherein R1, R2, R3, R5, R8 are OH or H or absent; wherein R9, R11, R12, R13, R14, and R15 are CH3; or wherein R1, R2, R5, R8 represent OH; R3 represents OH, H or absent; R4, R10 represent CH2Oangeloyl; R9, R11, R12, R13, R14, R15 represent CH3; or wherein R1, R2, R5, R8 represent OH or O-tigloyl; R3 represents OH, H, or absent; R4, R10 represent CH2O tigloyl; R9, R11, R12, R13, R14, R15 represent CH3; wherein the group attaching to the core compound selected from acetyl, angeloyl, tigloyl, senecioyl, Crotonoyl, O-3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl and alkenylcarbonyl are interchangeable or replaceable thereof. They can be the same group or in combination thereof.

A composition comprising an effective amount of compound selected from the above formula or a salt, ester, metabolite or derivative thereof can be used as a medicament for blocking the invasion, migration, metastasis of cancer cells, inhibiting tumor or cancer cell growth and for treating cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer.

This invention provides a composition comprising the compounds provided in the invention for treating cancers; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemonhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitis, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increase the expression of the genes: ANGPT2, DDIT3, LIF and NFKB1Z, and manufacturing an adjuvant composition and venotonic treatment.

Alkenyl means unsaturated linear or branched structures and combinations thereof, having formula R2 C=CR2, one or more double bonds therein. Examples of alkenyl groups include vinyl, propenyl, isopropenyl, butenyl, s- and t-butenyl, pentenyl, hexenyl, butadienyl, pentadienyl, and hexadienyl. An aryl is a functional group of organic molecule derived from an aromatic compound such as benzene, a 6-14 membered carbocyclic aromatic ring system comprising 1-3 benzene rings. If two or more aromatic rings are present, then the rings are fused together, so that adjacent rings share a common bond. Examples include phenyl and naphthyl. The aryl group may be substituted with one or more substitutes independently selected from halogen, alkyl or alkoxy. Acyl is a functional group which can be obtained from an organic acid by the removal of the carboxyl. Acyl groups can be written using the general formula —COR, where there is a double bond between the carbon and oxygen. The names of acyl groups typically end in -yl, such as formyl, acetyl, propionyl, butyryl and benzoyl. Benzoyl is one of the acyls, $C_6H_5COR$, obtained from benzoic acid by the removal of the carboxyl. A heterocyclic compound is a compound containing a heterocyclic ring which refers to a non-aromatic ring having 1-4 heteroatoms, said ring being isolated or fused to a second ring selected from 3- to 7-membered alicyclic ring containing 0-4 heteroatoms, aryl and heteroaryl, wherein heterocyclic compounds include pyrrolidinyl, pipyrazinyl, morpholinyl, trahydrofuranyl, imidazolinyl, thiomorpholinyl, and the like. Heterocyclyl groups are derived from heteroarenes by removal of a hydrogen atom from any ring atom. Alkanoyl is the general name for an organic functional group RCO—, where R represents hydrogen or an alkyl group.

Examples of alkanoyls are acetyl, propionoyl, butyryl, isobutyryl, pentanoyl and hexanoyl. Alkenoyl is an alkenylcarbonyl in which the alkenyl is defined above. Examples are pentenoyl (tigloyl) and pentenoyl (angeloyl). Alkyl is a radical containing only carbon and hydrogen atoms arranged in a chain, branched, cyclic or bicyclic structure or their combinations, having 1-18 carbon atoms. Examples include but are not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl and cyclohexyl. Benzoyl alkyl substituted alkanoyl refers to straight or branched alkanoyl substituted with at least one benzoyl and at least one alkyl, wherein the benzoyl is attached to a straight or branched alkyl. An example of a benzoyl alkyl substituted alkanoyl is benzoyl methyl isobutanoyl. A sugar moiety is a segment of molecule comprising one or more sugars or derivatives thereof or alduronic acid thereof.

(Y)Y3, Y and Y3 represent the same compound. YM and (ACH-Y) represent the same compound. Connecting moiety is a substructure or a group of atoms which connect the functional group to a core compound. Example: angeloyl group is connected by a sugar moiety to a triterpene core.

Acetyl=ethanoyl; Propionyl=methylpropanoyl; Crotonoyl=2-butenoyl; Isobutyryl=2-methylpropanoyl; 2-Ethylbutyryl=2-Ethylbutanoyl; Butyryl=n-Butyryl=butanoyl=C-4 Acyl; trans-2-Methyl-2-butenoyl=(E)-2,3-Dimethylacryloyl chloride=(E)-2-Methylcrotonoyl=3-cis-Methyl-methacryloyl=Tigloyl; 3,3-Dimethylacryloyl=3-Methyl-2-butenoyl=3-Methylcrotonoyl=Senecioyl; Propionyl chloride=methylpropanoyl; Hexanoyl=Caproyl; Heptanoyl=Enanthic=Oenanthic; Octanoyl=Capryloyl; Dodecanoyl=Lauroyl; Tetradecanoyl=Myristoyl; C(2-18) Acyl is an acyl group having 2 to 18 carbons.

ethanoyl is a C-2 Acyl, propanoyl is a C-3 Acyl, propenoyl is a C-3 Acyl, propionyl is a C-3 Acyl, butanoyl is a C-4 Acyl, butenoyl is a C-4 Acyl, crotonoyl is a C-4 Acyl, pentanoyl is a C-5 Acyl, pentenoyl is a C-5 Acyl, angeloyl is C-5 Acyl, tigloyl is C-5 Acyl, senecioyl is C-5 Acyl, hexanoyl is a C-6 Acyl, hexenoyl is a C-6 Acyl, heptanoyl is a C-7 Acyl, heptenoyl is a C-7 Acyl, octanoyl is a C-8 Acyl, octenoyl is a C-8 Acyl, nonanoyl is a C-9 Acyl, nonenoyl is a C-9 Acyl, decanoyl is a C-10 Acyl, decenoyl is a C-10 Acyl, lauroyl is a C-12 Acyl, dodecanoyl is a C-12 Acyl, myristoyl is a C-14 Acyl, oleoyl is a C-18 Acyl.

The building blocks used in the invention including triterpenes, hydroxylated triterpenes, acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methylmethacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl and Oleoyl, or halides thereof, or chloride thereof.

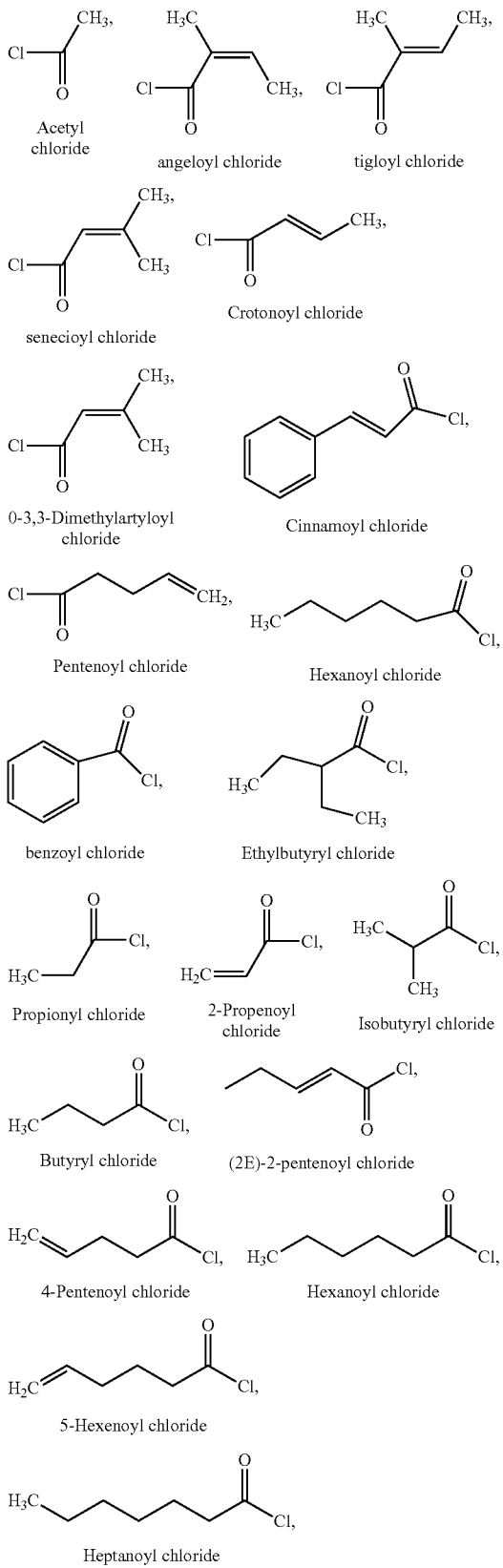

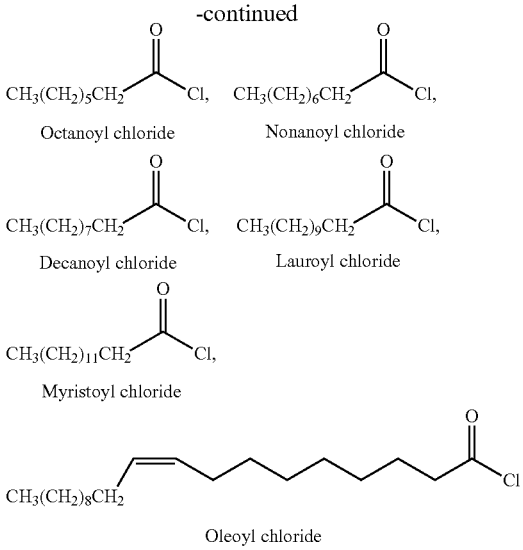

Acryloyl chloride [Synonym: 2-propenoly chloride]; Propionyl chloride [Synonym: methylpropanoyl chloride]; Crotonoyl chloride [Synonym: 2-butenoyl chloride]; Isobutyryl chloride [Synonym: 2-methylpropanoyl chloride]; 2-Ethylbutyryl chloride [Synonym: 2-Ethylbutanoyl chloride]; Butyryl chloride (Synonym: n-Butyryl chloride, butanoyl chloride, or C-4 Acyl halide); trans-2-Methyl-2-butenoyl chloride [Synonym: (E)-2,3-Dimethylacryloyl chloride, (E)-2-Methylcrotonoyl chloride, 3-cis-Methyl-methacryloyl chloride, Tigloyl chloride]; 3,3-Dimethylacryloyl chloride [Synonym: 3-Methyl-2-butenoyl chloride, 3-Methylcrotonoyl chloride, Senecioyl chloride]; Hexanoyl chloride [Synonym: Caproyl chloride]; Heptanoyl chloride [Synonym: Enanthic chloride, Oenanthic chloride] Octanoyl chloride [Synonym: Capryloyl chloride]

In the presented experiments, concentrations of drug that inhibit 15% cell-growth or less (i.e. 85% of control or above) as compared to the no-drug control (DMSO) are considered non-cytotoxic concentrations. In an embodiment, the concentrations of drug that inhibit 10% cell-growth or less (i.e. 90% of control or above) as compared to the no-drug control (DMSO) are considered non-cytotoxic concentrations. In an embodiment, the concentrations of drug that inhibit 5% cell-growth or less (i.e. 95% of control or above) as compared to the no-drug control (DMSO) are considered non-cytotoxic concentrations. In an embodiment, the concentrations of drug that inhibit 20% cell-growth or less (i.e. 80% of control or above) as compared to the no-drug control (DMSO) are considered non-cytotoxic concentrations. In an embodiment, the concentrations of drug that inhibit 25% cell-growth or less (i.e. 75% of control or above) as compared to the no-drug control (DMSO) are considered non-cytotoxic concentrations. In an embodiment, the concentrations of drug that inhibit 30% cell-growth or less as compared to the no-drug control (DMSO) are considered non-cytotoxic concentrations. In an embodiment, the concentrations of drug that inhibit 45% cell-growth or less as compared to the no-drug control (DMSO) are considered non-cytotoxic concentrations.

The triterpene compound or compounds selected from this invention can be administered to a subject in need thereof, treating the subject, wherein including preventing cancer, or providing an adjuvant effect to the subject, or inhibiting the initation or promotion of cancer, or killing the cancer/tumor cells, or inhibiting cancer cell invasion. In an embodiment the compounds inhibit the activation of Nuclear Factor-kB, wherein inhibiting the localization or wherein binding the DNA. In an embodiment the compounds induce apoptosis in cancer cells.

Determination of gene expression by Real-time PCR method (Brilliant QPCR, Agilent Technologies): The real-time polymerase chain reactions further confirm the results obtained from microarray analysis. The Real-time PCR results (shown below) confirmed that Compound Y3 and YM increase the expression of the genes: ANGPT2, DDIT3, LIF and NFKB1Z, wherein the results in Table 19-21 disclosed in PCT/US09/34115, filed Feb. 13, 2009.

The saponins are partially hydrolyzed into a mixture of products which can be separated by HPLC. Specific partial hydrolysis of saponins can also be achieved with enzymes. The glycosidases catalyze the hydrolysis of the glycosidic linkage. Galactosidase is an enzyme which catalyzes the hydrolysis of galactosides. Glucosidase is an enzyme which breaks glucose from saponin. Other enzyme examples are xylanases, lactase, amylase, chitinase, sucrase, maltase, and neuraminidase.

The sugar moiety of the triterpenoid saponin (example Xanifolia Y) can be removed by acid hydrolysis. The synthetic compound of ACH-Y is obtained. ACH-Y is a triterpene with acyl groups but no sugar moiety. The acyl group of the saponin (example Xanifolia Y) can be removed by alkaline hydrolysis. The synthetic compound AKOH-Y can be obtained. AKOH-Y is a pentacyclic triterpene with sugar moieties. A pentacyclic triterpene can be obtained by acid and alkaline hydroysis of saponins from natural sources. A pentacyclic triterpene can be obtained by synthetic methods (Reference: Surendra et al., Rapid and Enantioselective Synthetic Approches to Germanicol and Other Pentacyclic Triterpenes, Journal of the American Chemical Society, 2008, 130(27), 8865-8869). Pentacyclic triterpenes with sugar moieties can also be obtained by synthesis (Reference: Ple et al., Synthesis of L-arabinopyranose containing hederagenin saponins, Tetrahedron 61 (2005) 4347-4362). Acylation is the process of adding an acyl group to a compound. The Friedel-Crafts reaction is an example of this process. An active compound can be obtained by acylating a pentacyclic triterpenes, or hydroxylated triterpenes. In an embodiment, acylating C24, C28, C21 and C22 of a pentacyclic triterpenes, or hydroxylated triterpenes produce compounds for inhibiting cancer growth, cancer invasion, cell invasion, cancer cell invasion, molecular cell invasion, cell attachment adhesion, or cell circulation. In an embodiment, the acyl group(s) may be at C3. In an embodiment, a sugar moiety is at C21, 22, or 28, wherein the sugar moiety is attached with 2 acyl groups. In an embodiment, acylating the compounds of (A), (B), (C), (D1), (D2), (F), (G), (H), produce the compounds for inhibiting cancer invasion, cells invasion or cancer cell invasion; cancer metastasis; or cancer growth The building blocks in the present application are used to synthesise active saponins.

Acylating the compound (G) with angeloyl or tigloyl group gives the following compounds

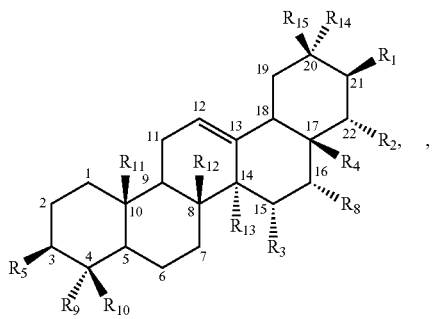

(K)

wherein R1, R2, R5, R8 represent OH or O-angeloyl; R3 represents OH, H or O-angeloyl; R4, R10 represent CH3, CH2OH or CH2Oangeloyl; R3 represents OH, H or O-angeloyl; R9, R11, R12, R13, R14, R15 represent CH3; or wherein R1, R2, R5, R8 represent OH or O-tigloyl; R3 represents OH, H or O— tigloyl; R4, R10 represent CH3, CH2OH or CH2O tigloyl; R9, R11, R12, R13, R14, R15 represent CH3; wherein the compounds inhibit cancer growth, cancer invasion, cells invasion or cancer cell invasion.

Acylating the compound (G) with angeloyl, tigloyl, senecioyl, acetyl, Crotonoyl, 3,3-Dimethylartyloyl, Cinnamoyl, Pentenoyl, Hexanoyl, benzoyl, Ethylbutyryl, alkyl, dibenzoyl, benzoyl, alkanoyl, alkenoyl, benzoyl alkyl substituted O-alkanoyl, alkanoyl substituted phenyl, alkenoyl substituted phenyl, aryl, acyl, heterocylic, heteroraryl, CH2O-alkenylcarbonyl, alkane, alkene give the compound (K) wherein R1, R2, R5, R8 represent OH, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; R4, R10 represent CH3, CH2OH, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, alkane, alkene; R3 is absent of represents OH, H, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; wherein R9, R11, R12, R13, R14, R15 represent CH3; wherein the compounds inhibit cancer growth, cancer invasion, cells invasion or cancer cell invasion; wherein the compound for use as mediator or inhibitor of adhesion protein or angiopoietin; wherein the compounds use as mediator modulating the secretion, expression, or synthesis of adhesion protein comprises reducing the fibronectin for inhibiting cell attachment, cell adhesion or cell circulation; wherein the adhesion proteins comprise fibronectin, integrins family, myosin, vitronectin, collagen, laminin, polyglycans, cadherin, heparin, tenascin, $CD_{54}$, and CAM; the compounds use for anti adhesion therapy and targeting adhesion molecules for therapy.

Applicant further states that anti-adhesion therapy and targeting adhesion molecules for therapy is a new direction for development of drugs. Some examples of anti-adhesion drugs in clinical trials are Efalizumab, Odulimomab, Alicaforsen, Aselizumab etc, which target varies adhesion proteins. Please see TEXT BOOK, Adhesion Molecules: Function and Inhibition, (Reference 2), edited by Klaus Ley page 289-291, 297.

Adhesion molecules in inflammatory disease, (Reference 4), Abstract, line 7-8 "Blockade of the function of expression of CAM has emerged as a new therapeutic target in inflammatory diseases". Applicants' invention is an anti-adhesion therapy which is a new use of the compound as a mediator or inhibitor of adhesion proteins and angiopoietins. It inhibits excess adhesion and inhibits cell attachment.

In the present application, Applicants have used compounds selected from structure (2A) for anti adhesion therapy, as a mediator or inhibitor of adhesion proteins and angiopoietins, and modulation of the cell attachment, and cell adhesion.

This invention provide a simple semi-synthetic method to obtain semi-natural compounds by chemically removing functional groups of well studied complex natural products to the basic core structure before de-novo chemically adding on active groups directly or sequentially by reaction with the active group donating chemical under different reaction temperature and time to produce series of different active group modified core structure compounds that can be fractionated and easily structurally determined as well as screening for different bio-active efficacies and toxicities as potential new drug candidates.

EXPERIMENTAL DETAILS

Experiment details of herb extraction, analysis of extract components by HPLC, determination of the cell-growth activity effected by Xanifolia Y with cells derived from different human organs using MTT Assay, purification of the bioactive components from plant extract, fractionation of plant extracts with FPLC, isolation of component Ys with preparative HPLC, determination of the chemical structure, cell experiments and animal studying are disclosed in PCT/US05/31900, U.S. Ser. No. 11/289,142, U.S. Ser. No. 10/906,303, U.S. Ser. No. 11/131,551 and U.S. Ser. No. 11/683,198, filed on Mar. 7, 2007, PCT/US2007/077273, filed Aug. 30, 2007, U.S. Ser. No. 60/890,380, filed on Feb. 16, 2007, U.S. Nos. 60/947,705, filed on Jul. 3, 2007, PCT/US2008/002086, 1188-ALA-PCT, filed Feb. 15, 2008, App'l No. PCT/US09/34115, filed Feb. 13, 2009. Experiments 1-23 of PCT/US2008/002086, 1188-ALA-PCT, filed Feb. 15, 2008.

Experiment 1

Removal of the Sugar Moiety from Saponin by Acid Hydrolysis 15 mg saponin was dissolved in 1 ml of Methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (sugar-removed saponin) was achieved by HPLC with isocratic elution of 80-100% acetonitrile.

Experiment 2

Removal of the Acyl Group by Alkaline Hydrolysis

Methods: 20 mg of saponin was dissolved in 0.5 ml of 1N NaOH. The solution was incubated in 80 C water bath for 4 hours. It was cooled to room temperature before neutralized with 0.5 ml 1N HCl (adjust pH to about 3). The mixture was extracted with 2 ml 1-butanol 3 times. The butanol fractions were collected and lyophilized. The hydrolyzed saponin with further purified with HPLC in a C-18 column eluted with 25% acetonitrile.

Experiment 3

Adding the Acyl Group to Triterpene by Esterification

Method: 40 mg of triterpene core (fraction IV) was dissolved in 1 ml pyridine in a 50 ml tube. Reaction is started by adding 0.2 ml of acyl chloride (Tigloyl chloride, angeloyl chloride, Acetyl chloride, Crotonoyl chloride, 3,3-Dimethylartyloyl chloride (senecioyl chloride), Cinnamoyl chloride, Pentenoyl chloride, Hexanoyl chloride, benzoyl chloride or Ethylbutyryl chloride). The mixture is stirred for 5 sec, 1 min, 2 min, 5 min, 10 min, 30 min, 1 hr, 2 hr, 18 hr, 2 days or 3 days at 0 C, 25 C or 75 C temperature. At the end of reaction, 5 ml of 2N HCl or 1M NaHCO3 is added to the reaction mixture. The solution is then extracted 3 times with 10 ml of ethyl acetate which is then evaporated under vacuum and at 45 C and lyophilization. The reaction product is dissolved in 80% acetonitrile-0.005% Trifluoroacetic acid or DMSO; and was separated with HPLC. Selecting the HPLC fractions for isolation is according to the cytotoxic activity of the reaction product obtained at a specific reaction time. The active esterification products are purified with HPLC. The reaction product of mixtures and individual compounds are tested with MTT cytotoxic assay. Structures are determined with NMR. See examples FIGS. 1-12

Experiment 4

Preparation of E4A

1. Beta-Escin dissolved in 1M NaOH (20 mg/ml) was incubated at 70 C for 5 hours.
2. The hydrolyzed solution was neutralized with HCl and the water was evaporated by lyophilization.
3. The product was dissolved in 50% methanol and 1N HCl. The mixture was incubated at 70 C for 5 hours.
4. The solution was neutralized with NaOH.
5. The hydrolyzed product was extracted with ethylacetate, which was subsequently removed by evaporation.
6. Further purification of the hydrolyzed product (E4A) was archived with FPLC chromatography in a C18 column equilibrated with 70% acetonitrile/TFA at the flow rate of 1 ml/min.

Experiment 5

Esterification of E4A with Tigloyl Chloride 1. 50 mg of E4A in 1 ml pyridine, stir gently in a 50 ml tube. Esterification was carried out at 25 C by adding 200 ul Tigloyl chloride.
2. Stir for 1 minute; then immediately add 5 ml of 2N HCl.
3. Stir for 1 hour and sit at room-Temp over night.
4. Extract the esterification products with 10 ml ethylacetate.
5. Evaporate the ethylacetate.
6. Dissolve the sample with 1 ml DMSO.
7. Fractionate the reaction products with HPLC.
8. Collect samples.

Experiment 6

Isolation of E4A-Tig Active Compounds with HPLC

1. Column: ZORBAX ODS 9.4×250 mm, 5 um
2. Solvents: A: 45% AN/TFA; B: 100% AN/TFA
3. Chromatography conditions: a) Elution: Solvent A to B in 80 min; then with solvent B for 40 min; b) flow rate: 1 ml/mim. c) Monitor OD: at 207 nm;

Experiment 7

MTT Experiment

Cells. HTB-9 (bladder), HeLa-S3 (cervix), DU145 (prostate), H460 (lung), MCF-7 (breast), K562 (leukemia), HCT116 (colon), HepG2 (liver), U2OS (bone), T98G (brain), SK-MEL-5 (Skin) and OVCAR 3, ES2 (ovary), Pancreas (Capan), Mouth (KB), Kidney (A498).

MTT Assay. The procedure for MTT assay followed the method described by Carmichael et al. (1987) with modifications. The cells were seeded into a 96-well plate at for 24 hours before drug-treatment. The cells were then exposed to the drugs for 48, 72, or 96 hours. After the drug-treatment, MTT (0.5 mg/mL) was added to cultures and incubated for an hour. The formazan (product of the reduction of tetrazolium by viable cells) formed and was dissolved with DMSO and the O.D. at 490 nm, and was measured by an ELISA reader. The MTT level of the cells before drug-treatment was also measured (T0). The % cell-growth (% G) is calculated as: % G=(TD−T0/TC−T0)×100(1), where TC or TD represents O.D. readings of control or drug-treated cells.

When T0>TD, then the cytotoxicity (LC) expressed as % of the control is calculated as:

% $LC=(TD-T0/T0)\times100(2)$.

MTT Assay is performed to intermediate and final products from experiments.

Experiment 8

Chemical Synthesis, Isolation and Characterization of E4A-Tig-R

Chemical synthesis of E4A-Tig-R: 1. Preparation of E4A; 2. Esterification of E4A with Tigloyl Chloride; 3. Isolation of E4A-Tig-R with HPLC Cytotoxic activity determination: 1. MTT assay Chemical structure determination: 1. NMR analysis; 2. Mass Spectrum analysis Compound E4A-Tig-R: 24,28-O-Tigloyl-3β,16α,21β,22α,24β,28-hexahydroxyolean-12-ene

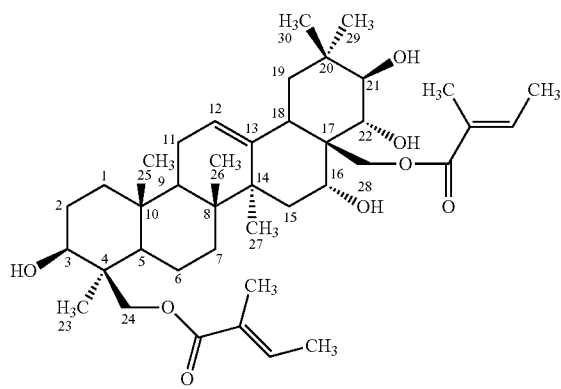

Experiment 9

Chemical Synthesis, Isolation and Characterization of E4A-Tig-N

Chemical synthesis of E4A-Tig-N: 1. Preparation of E4A; 2. Esterification of E4A with Tigloyl Chloride; 3. Isolation of E4A-Tig-N with HPLC Cytotoxic activity determination: 1. MTT assay Chemical structure determination: 1. NMR analysis; 2. Mass Spectrum analysis

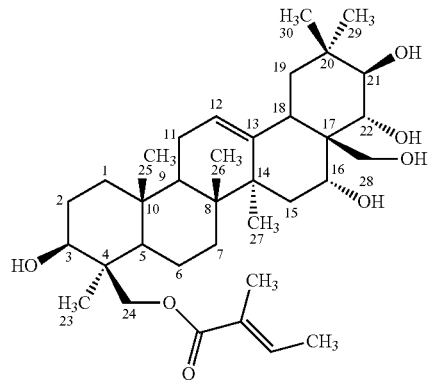

Experiment 10

Chemical Synthesis, Isolation and Characterization of E4A-Tig-Q

Chemical synthesis of E4A-Tig-Q: 1. Preparation of E4A; 2. Esterification of E4A with Tigloyl Chloride; 3. Isolation of E4A-Tig-Q with HPLC Cytotoxic activity determination: 1. MTT assay Chemical structure determination: 1. NMR analysis; 2. Mass Spectrum analysis

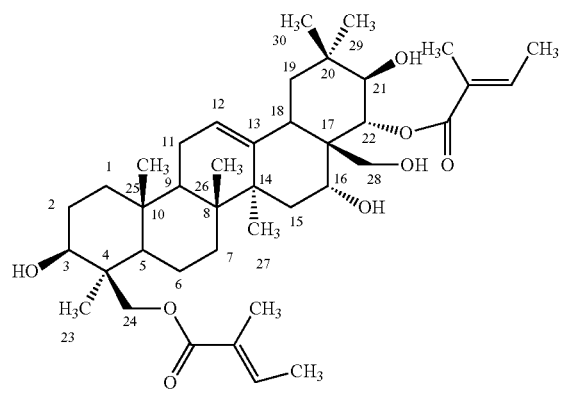

Experiment 11

Chemical Synthesis, Isolation and Characterization of E4A-Tig-V

Chemical synthesis of E4A-Tig-V: 1. Preparation of E4A; 2. Esterification of E4A with Tigloyl Chloride; 3. Isolation of E4A-Tig-V with HPLC Cytotoxic activity determination: 1. MTT assay Chemical structure determination: 1. NMR analysis; 2. Mass Spectrum analysis

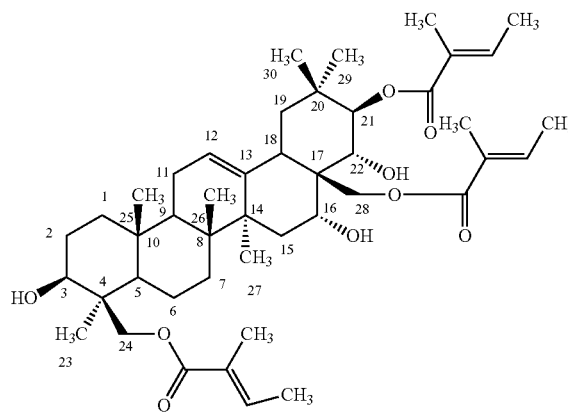

Experiment 12

Chemical Synthesis, Isolation and Characterization of E4A-Tig-T

Chemical synthesis of E4A-Tig-T: 1. Preparation of E4A; 2. Esterification of E4A with Tigloyl Chloride; 3. Isolation of E4A-Tig-T with HPLC Cytotoxic activity determination: 1. MTT assay Chemical structure determination: 1. NMR analysis; 2. Mass Spectrum analysis

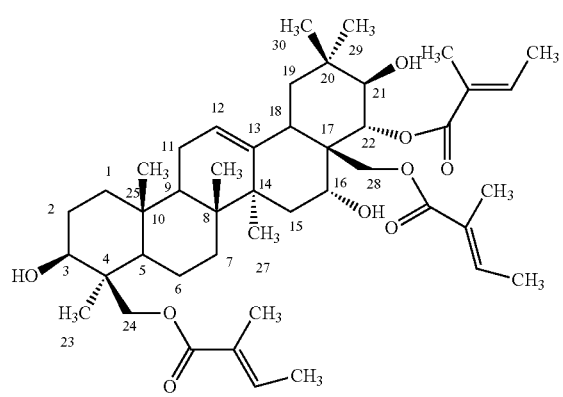

Experiment 13

Chemical Synthesis, Isolation and Characterization of E4A-Tig-U

Chemical synthesis of E4A-Tig-U: 1. Preparation of E4A; 2. Esterification of E4A with Tigloyl Chloride; 3. Isolation of E4A-Tig-U with HPLC Cytotoxic activity determination: 1. MTT assay Chemical structure determination: 1. NMR analysis; 2. Mass Spectrum analysis

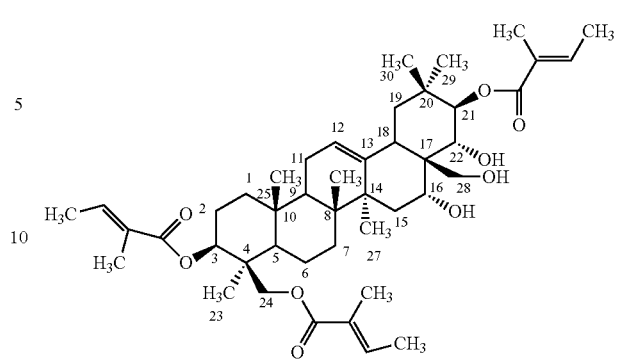

Experiment 14

Chemical Synthesis, Isolation and Characterization of E4A-Tig-S

Chemical synthesis of E4A-Tig-S: 1. Preparation of E4A; 2. Esterification of E4A with Tigloyl Chloride; 3. Isolation of E4A-Tig-S with HPLC Cytotoxic activity determination: 1. MTT assay Chemical structure determination: 1. NMR analysis; 2. Mass Spectrum analysis

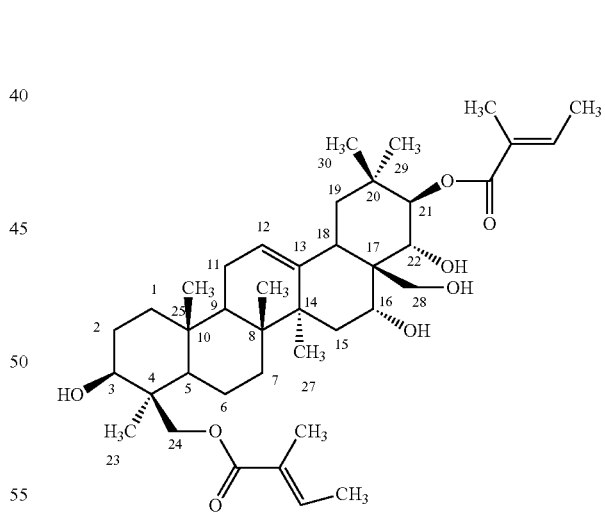

Experiment 15

Using method in Experiment 3, esterification of E4A with acetyl, angeloyl, tigloyl, senecioyl, Crotonoyl, Cinnamoyl, Pentenoyl gave the following compounds:

Compound E4A-Ang-R
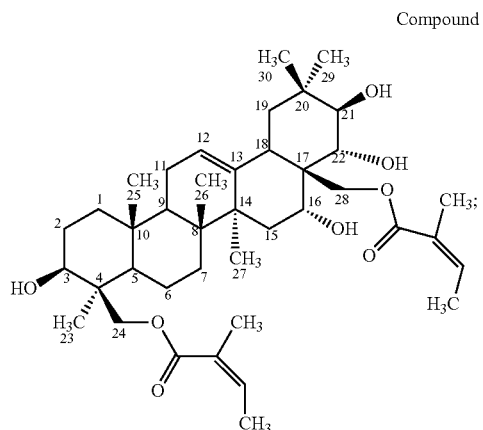
Compound E4A-Ang-V
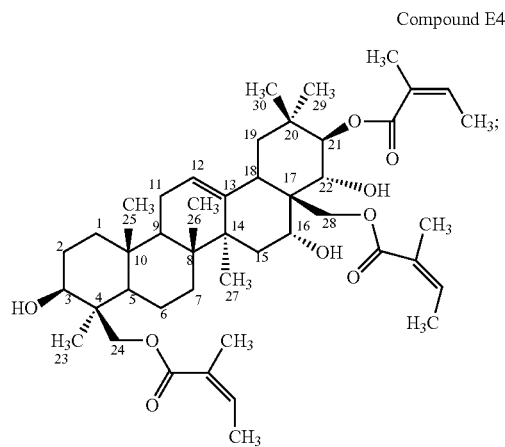
Compound E4A-Ang-Q
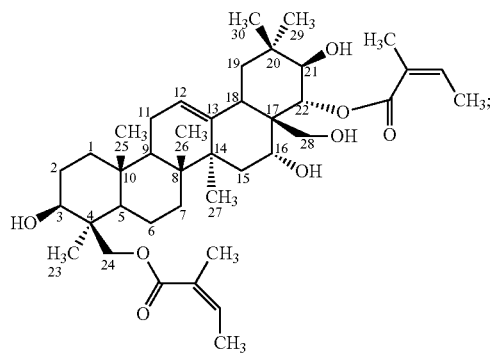
Compound E4A-Ang-N
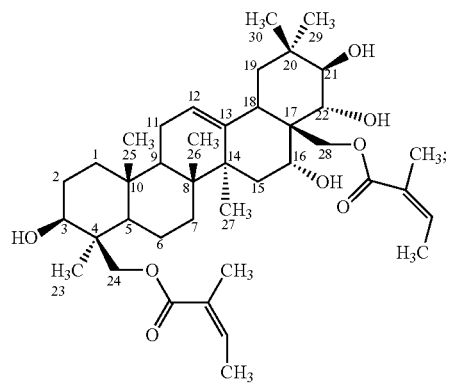
Compound E4A-Ang-T
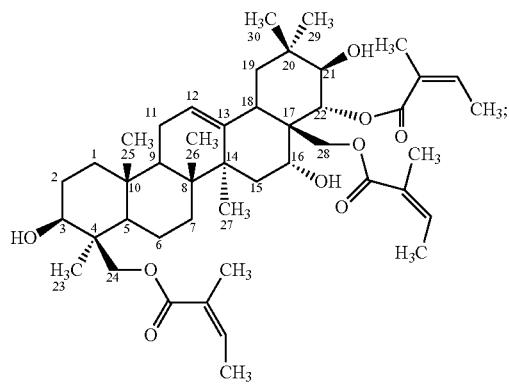
Compound E4A-Ang-U
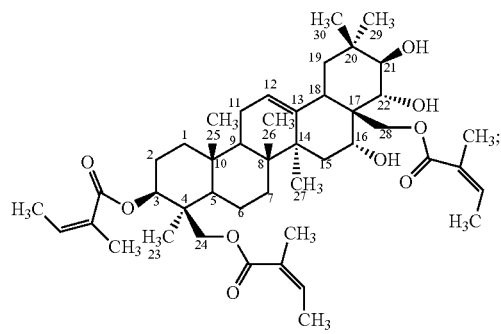
Compound E4A-Ang-S
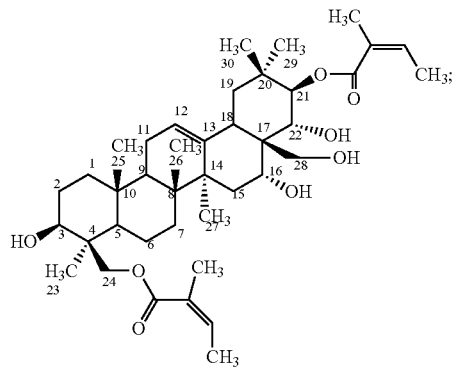
Compound E4A-Sen-R
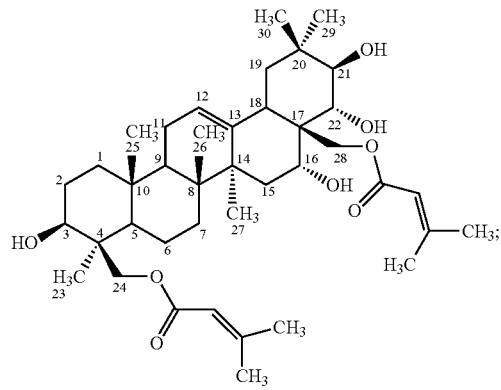

-continued
Compound E4A-Sen-V
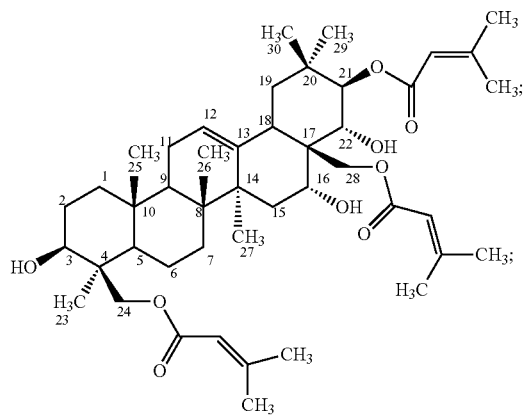
Compound E4A-Sen-N
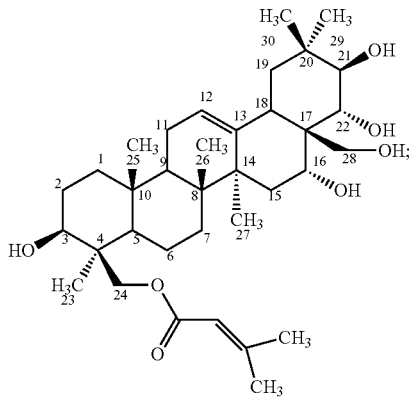
Compound E4A-Sen-Q
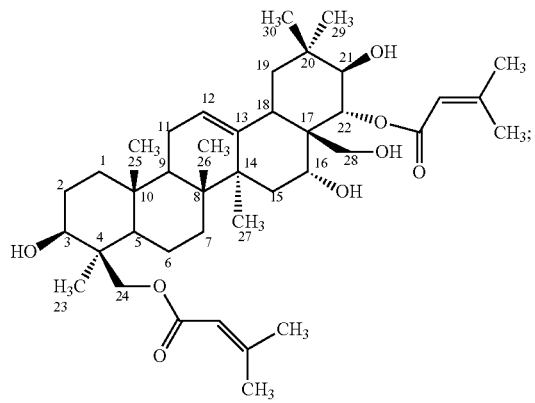
Compound E4A-Sen-S
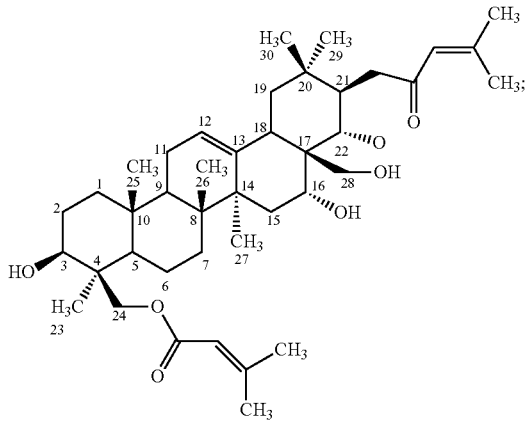
Compound E4A-Sen-T
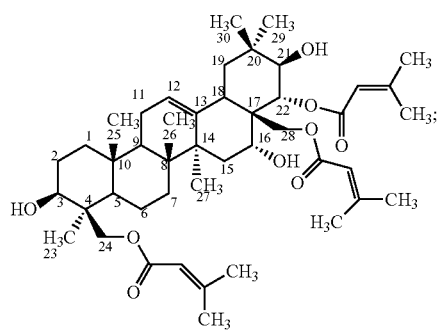
Compound E4A-Sen-U
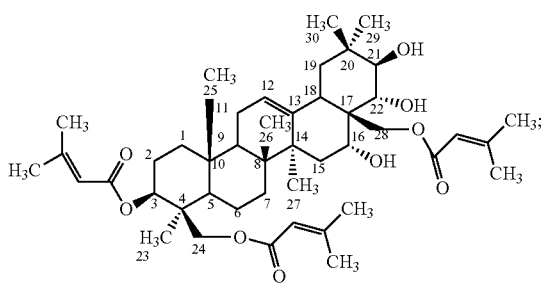
Compound E4A-Cro-R
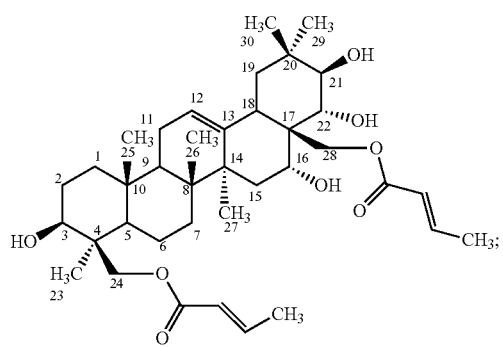
Compound E4A-Cro-V
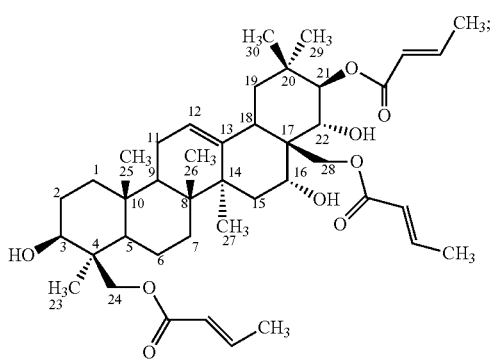

103
-continued
Compound E4A-Cro-N
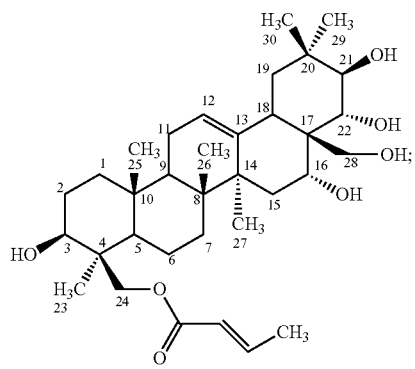
Compound E4A-Cro-Q
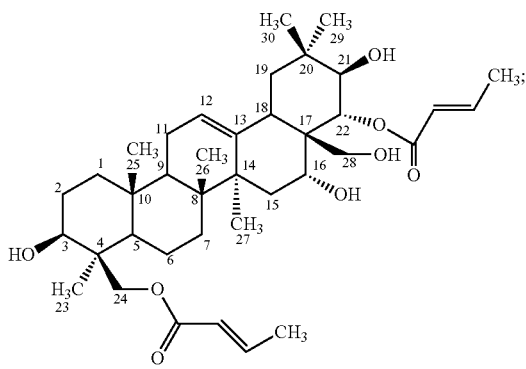
Compound E4A-Cro-S
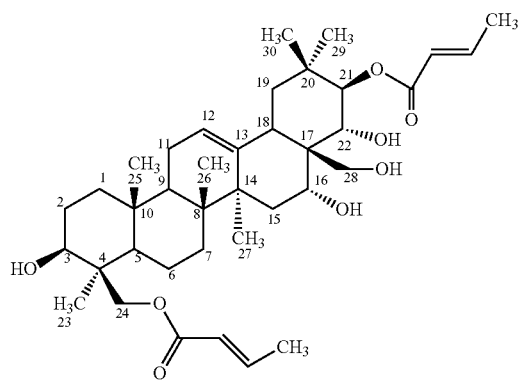
Compound E4A-Cro-T
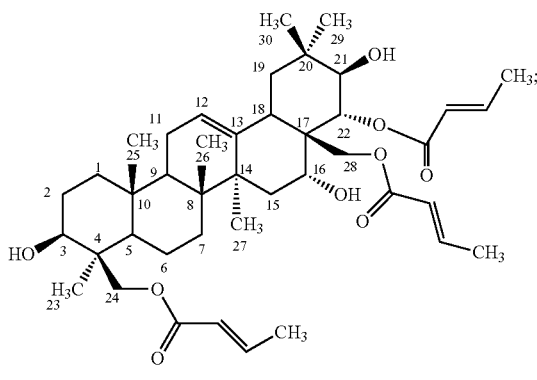
Compound E4A-Cr
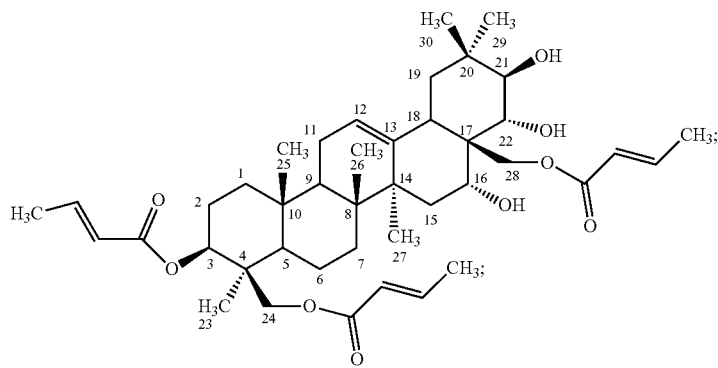
Compound E4A-Acy-R
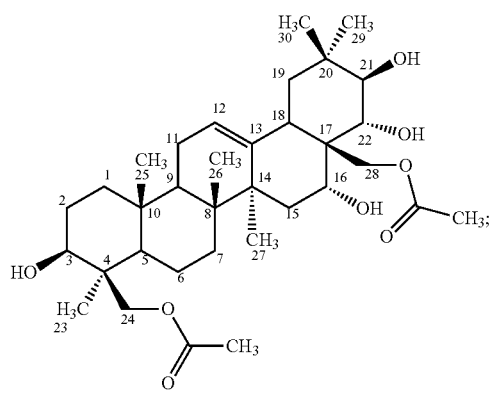
Compound E4A-Acy-V

Compound E4A-Acy-N
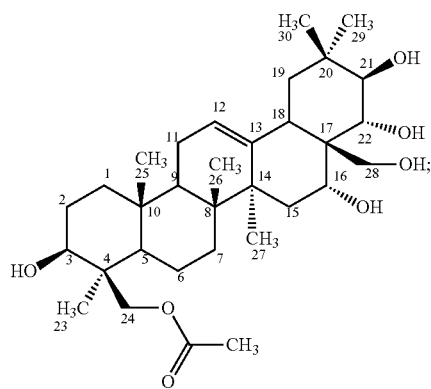
Compound E4A-Acy-Q
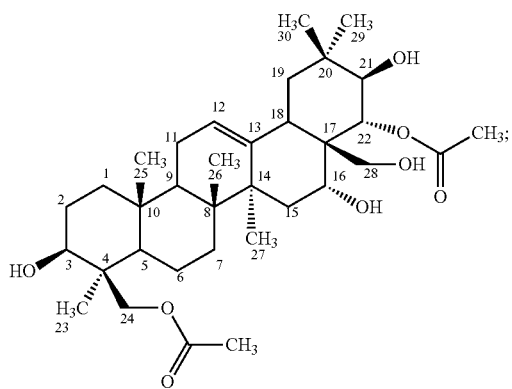
Compound E4A-Acy-S
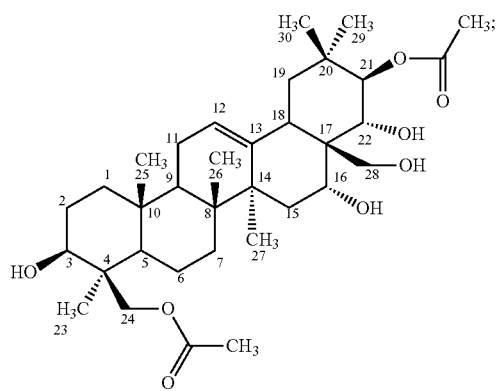
Compound E4A-Acy-T
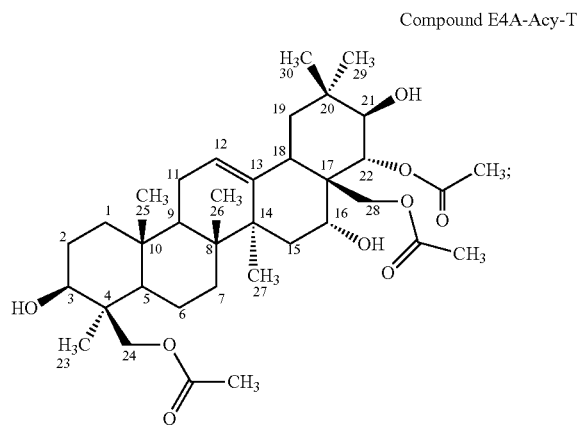
Compound E4A-Acy-U
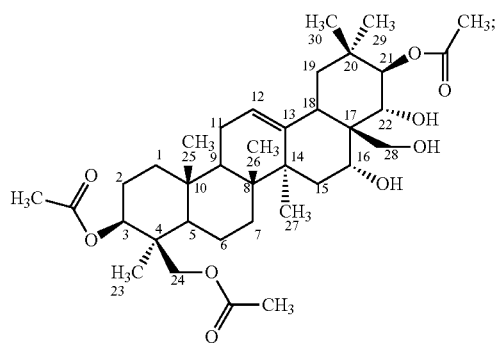
Compound E4A-Pen-R
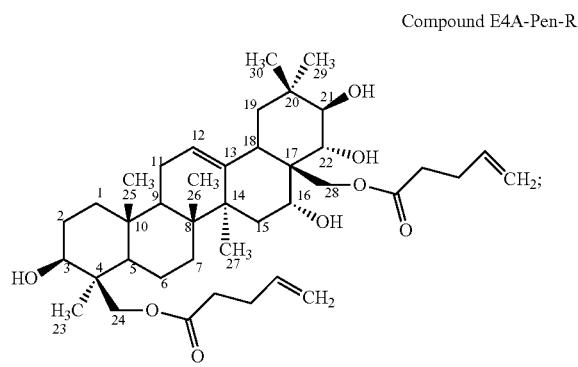
Compound E4A-Pen-V
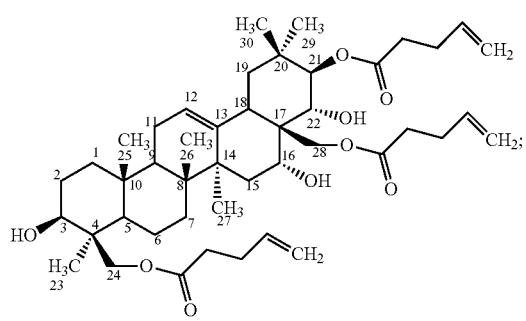
Compound E4A-Pen-N
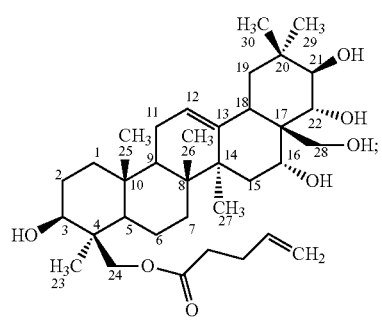

-continued
Compound E4A-Pen-Q
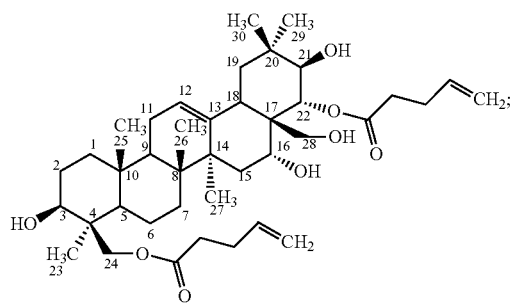
Compound E4A-Pen-S
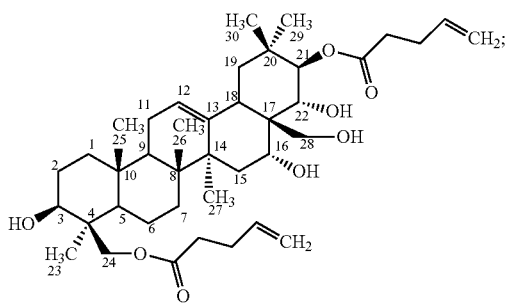
Compound E4A-Pen-T
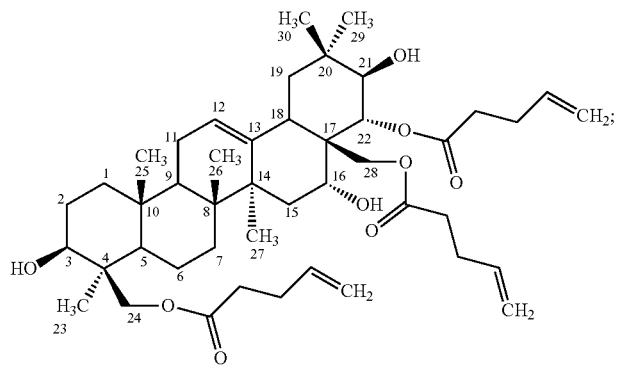
Compound E4A-Pen-U
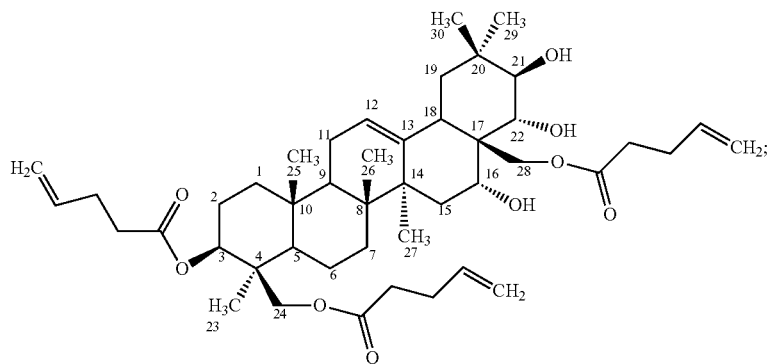
Compound E4A-Pen-R
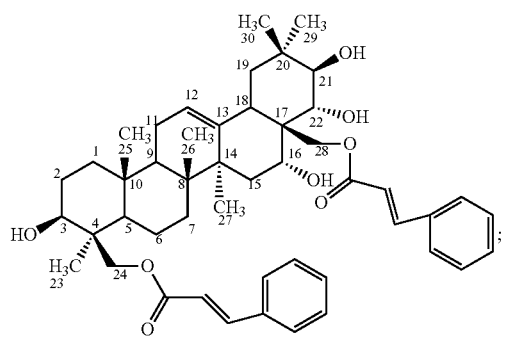
Compound E4A-Pen-V
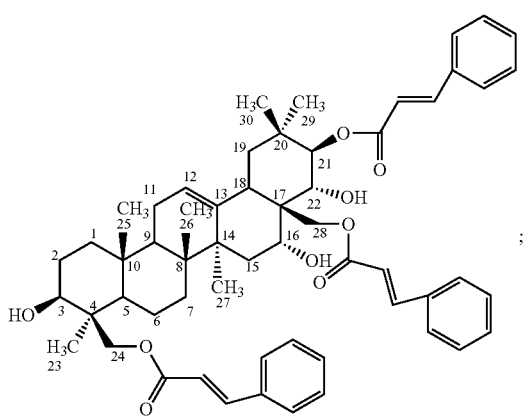

Compound E4A-Pen-N
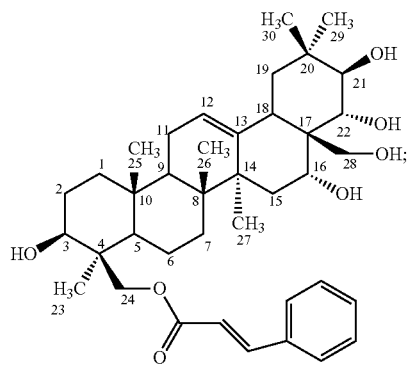
Compound E4A-Pen-Q
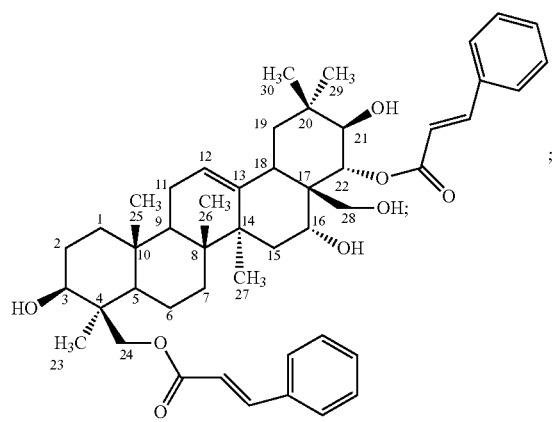
Compound E4A-Pen-S
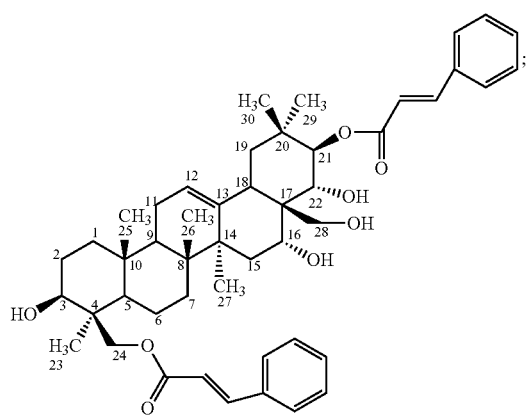
Compound E4A-Pen-T
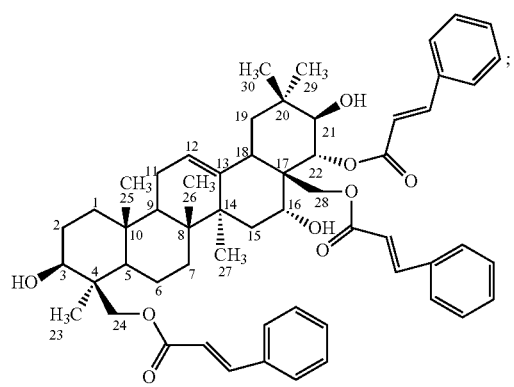
Compound E4A-Cin-U
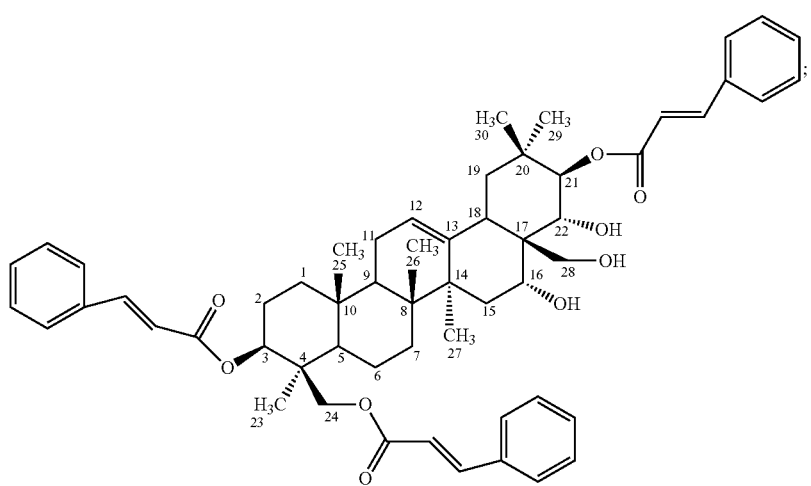

Experiment 16

Esterification of E4A-Tig-N with Senecioyl Chloride

Chemical synthesis of E4A-Tig-Sen-1:1. Esterification of E4A-Tig-N with Senecioyl Chloride; 3. Isolation of E4A-Tig-Sen-1 with HPLC
Cytotoxic activity determination: 1. MTT assay
Chemical structure determination: 1. NMR analysis; 2. Mass Spectrum analysis

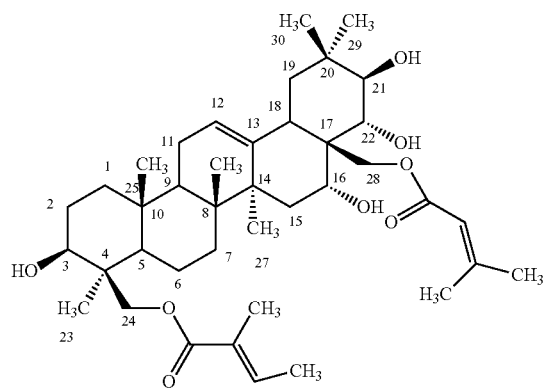

Experiment 17

Esterification of E4A-Tig-N with angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride or Ethylbutyryl chloride; Isolation with HPLC; Cytotoxic activity determination; Chemical structure determination with the method of Experiment 8, gave the following compounds:

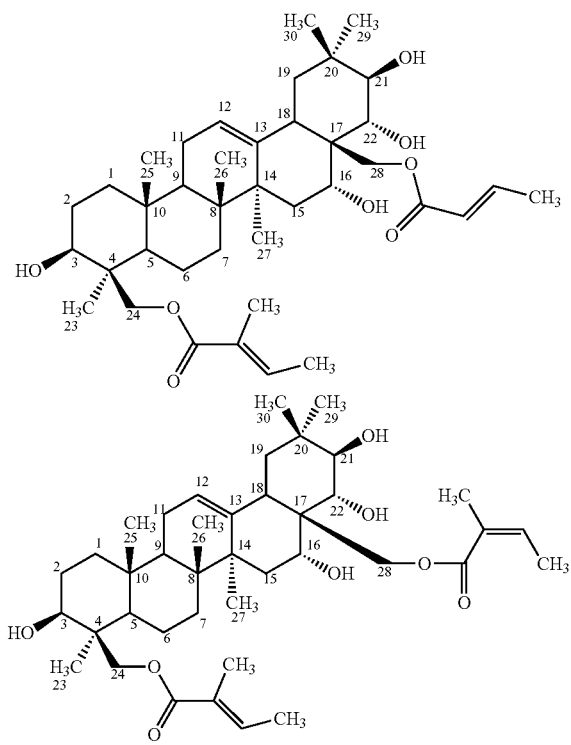

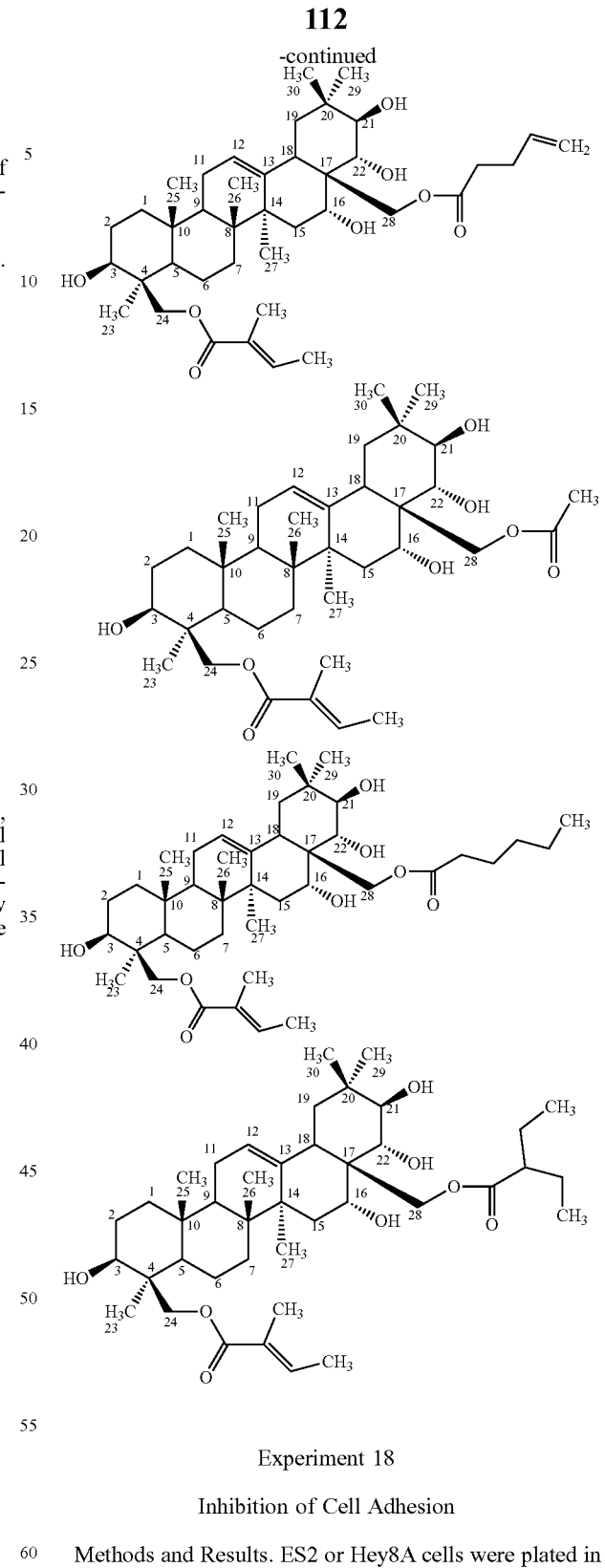

Experiment 18

Inhibition of Cell Adhesion

Methods and Results. ES2 or Hey8A cells were plated in T25 flasks with medium containing 5 ug/ml of compounds selected from structure (2A) including E4A-Tig-R, E4A-Tig-V, E4A-Tig-S, E4A-Tig-N, E4A-Tig-Q, E4A-Tig-T. Cultures were incubated for hours. Attached cells were removed from flasks by trypsinization and the numbers/amounts were counted. Compare to no drug controls, 80±4% of ES2 cells and 60±4% of Hey8A cells were found attached to flasks under this condition. At 5 ug/ml of above compounds, over 90% of unattached cells are alive as determined by the trypan Blue exclusion assay and by their ability to re-attach to flasks when plating in medium without tested compounds. However, with 10 ug/ml tested compounds, less than 40% of cells attached to flasks and many of them are dead cells. This experiment shows that tested compounds inhibit cells adhesion process.

Experiment 19

Fibronectin Secretion Experiment

Western blot is applied in this invention as a method to detect the specific proteins in treated and untreated cells with compounds in this invention, wherein the cells are bladder, cervix, prostate, lung, breast, leukemia, colon, liver, bone, brain, Skin, ovary, Pancreas (Capan), Mouth (KB), Kidney.

Cells: targeted cells were grown in RPMI 1640 medium. 1.5 million cells were seeded in a T25 flask and grown for 24 hours before drug-treatment.

Drug-treatment: Cells cultures were replaced with fresh RPMI medium containing either 2.5 ul of DMSO (as control) [D]; or 10, 20, 30, 40, 80 ug/ml of tested compounds.

After 24 hours, aliquot of culture medium was taken out for Fibronectin determination (Western blot method).

Cell viability at 24 hours was determined by MTT assay. Cultures were replaced with RPMI medium (5 ml) with MTT and incubated for an hour. The formation of formazan was dissolved in 10 ml of DMSO and OD at 570 nm was measured (MTT units).

Western Blot: Spent culture medium was mixed with SDS sample buffer, boiled for 3 minutes before loading to SDS gel. Samples were applied to a 6-10% SDS gel and electrophoresis was conducted with 100 volts for 2 hours. Protein was transferred to a nitrocellulose membrane electrophoretically. The nitrocellulose blot was incubated with the first antibody and second antibody (AP conjugated, Promega S3721). The immuno-bands were developed with BCIP/NBT color development system.

Determination of Western blot band intensity: The band-images of Western blot were captured with a digital camera and the intensity of bands was determined using "Image J" software.

Results show that compounds of E4A-Tig-R, E4A-Tig-V, E4A-Tig-S, E4A-Tig-N, E4A-Tig-Q, E4A-Tig-T inhibit fibronectin secretion from 20-40%. in bladder, cervix, prostate, lung, breast, leukemia, colon, liver, bone, brain, Skin, ovary, Pancreas (Capan), Mouth (KB), Kidney.

Experiment 20

Esterification of E4A with Propionyl Chloride

Methods: 50 mg of E4A in 1 ml pyridine, stir gently in a 50 ml tube. Esterification was carried out at 25 C by adding 200 ul Propionyl chloride, and immediately withdrawn 200 ul from the mixture and added to 1 ml of 2N HCl. (ASAP sample). At 1, 2, 5, 10 and 60 minutes afterward; 200 ul of reaction mixture was similarly withdrawn and add to 1 ml of 2N HCl. Mixtures were sit at room-Temp over night. Extract the esterification products with 2 ml ethylacetate. Evaporate the ethylacetate. Dissolve the sample with DMSO (final concentration of 40 mg/ml). Fractionate the reaction products with HPLC (C18 column, 1 ml/min).

HPLC condition: Column: C18 (9.4×250 mm, 5 um); Solvents: 80% Acetonitrile-0.005% TFA; Gradient: isocratic; Flow-rate: 1 ml/min; O.D.: 207 nm, AT=1024; Chart speed: 0.1 cm/min; Run time: 120 min; MTT assay (Cytotoxicity determination) condition: Cells: ES2 (ovarian cancer). Cell density: plate10K cells per well over night before addition of drug. Drug incubation time: 2 days.

Experiment 21

Esterification of E4A with Isobutyryl Chloride

Methods: 52 mg of E4A in 1 ml pyridine, stir gently in a 50 ml tube. Esterification was carried out at 25° C. by adding 200 ul of isobutyryl chloride. 2 minute later, 4 ml 2N HCl was added to the reaction mixture. Mixtures were kept at room-Temp over night. Extract the esterification products with 5 ml ethyl acetate. Evaporate the ethyl acetate. Dissolve the sample with DMSO (final concentration of 40 mg/ml). Fractionate the reaction products with HPLC (C18 column).

HPLC condition: Column: C18 (9.4×250 mm, 5 um); Solvents: 80% Acetonitrile-0.005% TFA; Gradient: isocratic; Flow-rate: 1 ml/min; O.D.: 207 nm, AT=1024; Chart speed: 0.1 cm/min; Run time: 200 min.

MTT assay (Cytotoxicity determination) condition: Cells: ES2 (ovarian cancer); Cell density: plate10K cells per well over night before addition of drug; Drug incubation time: 2 days.

Experiment 22

Esterification of E4A with 3,3-dimethylacryloly chloride from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature and 0 C. Fractionate the reaction products with HPLC (C18 column). Cytotoxic activity is determined with MTT. Chemical structure determined with NMR.

Experiment 23

Esterification of E4A with Pentenoyl chloride—from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature. Fractionate the reaction products with HPLC (C18 column). Cytotoxic activity is determined with MTT. Chemical structure determined with NMR.

Experiment 24

Esterification of E4A with Hexanoly chloride from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at 0 C. Fractionate the reaction products with HPLC (C18 column). Cytotoxic activity is determined with MTT. Chemical structure determined with NMR.

Experiment 25

Esterification of E4A with Acetyl chloride (H) from different times of esterification reaction. Reaction products obtained from each time of reaction (1 min, 2 min, 5 min and 10 min) were fractionated by HPLC. The profile is plotted according to HPLC elution time and optical density of fractions. Reaction was performed at Room temperature. Fractionate the reaction products with HPLC (C18 column). Cytotoxic activity is determined with MTT. Chemical structure determined with NMR.

Experiment 26

Esterification products of E4A with Crotonoyl chloride (I) from different times of esterification reaction. Reaction products obtained from each time of reaction (5 sec, 1 min, 2 min, 5 min and 10 min) were fractionated by HPLC. The profile is plotted according to HPLC elution time and optical density of fractions. Reaction was performed at Room temperature. Fractionate the reaction products with HPLC (C18 column). Cytotoxic activity is determined with MTT. Chemical structure determined with NMR.

Experiment 27

Esterification products of E4A with Cinnamoyl chloride (J) from different times of esterification reaction. Reaction products obtained from each time of reaction (1 min, 1 hour, 2 hours, 18 hours, 18 hours (heat)) were fractionated by HPLC. The profile is plotted according to HPLC elution time and optical density of fractions. Reaction was performed at Room temperature and 75 C. Fractionate the reaction products with HPLC (C18 column). Cytotoxic activity is determined with MTT. Chemical structure determined with NMR.

Experiment 28

Esterification products of E4A with pentenoyl, hexanoyl, benzoyl, ethylbutyryl, propionyl, 2-propenoyl, isobutyryl, butyryl, (2E)-2-pentenoyl, 4-Pentenoyl, 5-hexenoyl, heptanoyl, octanoyl, nonanoyl, decanoyl, Lauroyl, myristoyl, from different times of esterification reaction. Reaction products obtained from each time of reaction were fractionated by HPLC. The profile is plotted according to HPLC elution time and optical density of fractions. Fractionate the reaction products with HPLC (C18 column). Cytotoxic activity is determined with MTT. Chemical structure determined with NMR.

Experiment 29

Esterification products of E4A with propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl from different times of esterification reaction. Reaction products obtained from each time of reaction were fractionated by HPLC. The profile is plotted according to HPLC elution time and optical density of fractions. Fractionate the reaction products with HPLC (C18 column). Cytotoxic activity is determined with MTT. Chemical structure determined with NMR.

What is claimed is:
1. A compound selected from the structure:

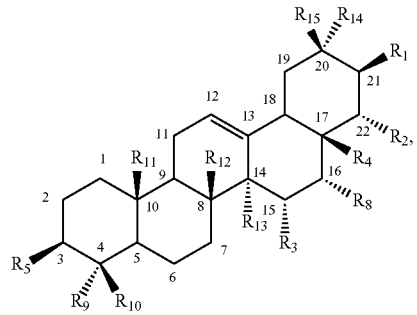

R1, R2, R3, R4, R5, R8, R9, R11, R12, R13, R14, R15 are independently selected from the group of CH3, CH2OH, COOH, hydrogen, hydroxyl, O-angeloyl, O-tigloyl, O-senecioyl, O-Crotonoyl, O-3,3-Dimethylacryloyl, O-Cinnamoyl, O-Pentenoyl, O-Hexanoyl, CH2O-angeloyl, CH2O-tigloyl, CH2O-senecioyl, CH2O-Crotonoyl, CH2O-3,3-Dimethylacryloyl, CH2O-Cinnamoyl, CH2O-Pentenoyl, and CH2O-Hexanoyl; wherein R10 is attached an O-angeloyl, O-tigloyl, O-senecioyl, O-Crotonoyl, O-3,3-Dimethylacryloyl, O-Cinnamoyl, O-Pentenoyl, O-Hexanoyl, CH2O-angeloyl, CH2O-tigloyl, CH2O-senecioyl CH2O-Crotonoyl, CH2O-3,3-Dimethylacryloyl, CH2O-Cinnamoyl, CH2O-Pentenoyl, or CH2O-Hexanoyl.

2. The compound of claim 1, wherein R10 and at least 1 or 2 of R1, R2, R3, R4, R5, R8, are independently attached an O-angeloyl, O-tigloyl, O-senecioyl, O-Crotonoyl, O-3,3-Dimethylacryloyl, O-Cinnamoyl, O-Pentenoyl, O-Hexanoyl, CH2O-angeloyl, CH2O-tigloyl, CH2O-senecioyl, CH2O-Crotonoyl, CH2O-3,3-Dimethylacryloyl, CH2O-Cinnamoyl, CH2O-Pentenoyl, or CH2O-Hexanoyl.

3. The compound of claim 1, wherein R1, R4 and R10 are independently attached an O-angeloyl, O-tigloyl, O-senecioyl, O-Crotonoyl, O-3,3-Dimethylacryloyl, O-Cinnamoyl, O-Pentenoyl, O-Hexanoyl, CH2O-angeloyl, CH2O-tigloyl, CH2O-senecioyl, CH2O-Crotonoyl, CH2O-3,3-Dimethylacryloyl, CH2O-Cinnamoyl, CH2O-Pentenoyl, or CH2O-Hexanoyl.

4. The compound of claim 1, wherein R4 and R10 are independently attached an O-angeloyl, O-tigloyl, O-senecioyl, O-Crotonoyl, O-3,3-Dimethylacryloyl, O-Cinnamoyl, O-Pentenoyl, O-Hexanoyl, CH2O-angeloyl, CH2O-tigloyl, CH2O-senecioyl, CH2O-Crotonoyl, CH2O-3,3-Dimethylacryloyl, CH2O-Cinnamoyl, CH2O-Pentenoyl, or CH2O-Hexanoyl.

5. The compound of claim 1, wherein R10 is attached an O-angeloyl, O-tigloyl, O-senecioyl, O-Crotonoyl, O-3,3-Dimethylacryloyl, O-Cinnamoyl, O-Pentenoyl, O-Hexanoyl, —CH2O-angeloyl, CH2O-tigloyl, CH2O-senecioyl, CH2O-Crotonoyl, CH2O-3,3-Dimethylacryloyl, CH2O-Cinnamoyl, CH2O-Pentenoyl, or CH2O-Hexanoyl.

6. The compound of claim 1, wherein R4 and R10 are independently attached an CH2O-angeloyl, CH2O-tigloyl, CH2O-senecioyl, CH2O-Crotonoyl, CH2O-3,3-Dimethylacryloyl, CH2O-Cinnamoyl, CH2O-Pentenoyl, CH2O-Hexanoyl, wherein R1, R2, R3, R5, R8 are OH or H or absent; wherein R9, R11, R12, R13, R14, and R15 are CH3.

7. The compound of claim 1, wherein R1 and R10 are independently attached an O-angeloyl, O-tigloyl, O-senecioyl, O-Crotonoyl, O-3,3-Dimethylacryloyl, O-Cinnamoyl, O-Pentenoyl, O-Hexanoyl, CH2O-angeloyl, CH2O-tigloyl, CH2O-senecioyl, CH2O-Crotonoyl, CH2O-3,3-Dimethylacryloyl, CH2O-Cinnamoyl, CH2O-Pentenoyl, or CH2O-Hexanoyl.

8. The compound of claim 1, wherein the compound is selected from the following:
   a) An isolated, purified or synthesized compound having structure:

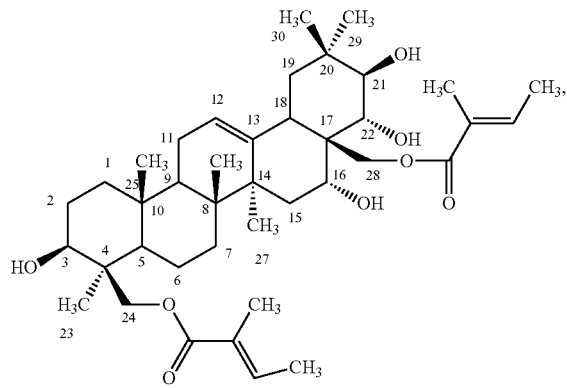

or chemical name: 24,28-O-Tigloyl-3β,16α,21β,22α,24β,28-hexahydroxyolean-12-ene.

9. A composition comprising the compound of claim 1 and a pharmaceutically acceptable carrier or diluent.

10. The compound of claim 1, for treating cancer, inhibiting cancer growth, inhibiting cancer invasion, inhibiting cancer metastasis, modulating cell adhesion, or modulating cell attachment, wherein the cancer is selected from the group consisting of breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; wherein said cell is selected from the group consisting of breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphatic cell, pancreatic cell, stomach cell and thyroid cell.

11. The compound of claim 1, for treating cancers, inhibition of cancer growth, cancer invasion, cells invasion, cancer cell invasion; cell adhesion, cell attachment, cell circulating; for inhibiting viruses; for preventing cerebral aging; for improving memory; improving cerebral functions; for curing enuresis, frequent micturition, urinary incontinence; for treating dementia, Alzheimer's disease, autism, brain trauma, Parkinson's disease or other neurodegenerative diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular disease; inhibiting NF-kappa B activation; for treating brain edema, severe acute respiratory syndrome, respiratory viral diseases, chronic venous insufficiency, hypertension, chronic venous disease, oedema, inflammation, hemorrhoids, peripheral edema formation, varicose vein disease, flu, post traumatic edema and post-operative swelling; for inhibiting blood clots, for inhibiting ethanol absorption; for lowering blood sugar; for regulating adrenocorticotropin and corticosterone levels; for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increasing the expression of the genes: ANGPT2, DDIT3, LIF and NFKB1Z, and manufacturing an adjuvant composition and venotonic treatment.

12. The compound of claim 1, for anti-adhesion therapy.

13. A composition comprising an effective amount of the compound of claim 1 as a medicament.

14. The compound of claim 1, wherein the compound can be obtained with a method comprising the following steps:
   1. Dissolving a hydroxylated triterpene core in pyridine,
   2. Adding acyl chloride,
   3. The mixture is stirred for a length of time including 5 sec, 10 sec, 20 sec, 30 sec, 40 sec, 1 min, 2 min, 5 min, 10 min, 30 min, 1 hr, 2 hr, 18 hr, 2 days and 3 days at different temperature,
   4. At the end of reaction, an aqueous solution of acid or base, or water is added to the reaction mixture,
   5. The solution is then extracted with ethyl acetate, and ethyl acetate is removed by evaporation and lyophilization,
   6. Dissolving the reaction product in acetonitrile with trifluoroacetic acid or DMSO to give a reaction product mixture,
   7. Separating the reaction product mixture with HPLC,
   8. Selecting the HPLC fractions for isolation according to their cytotoxic activity,
   9. Purifying the active esterification products with HPLC, and
   10. Collecting the products.

15. The compound of claim 14, wherein the core compound is terpene, isoprene, or triterpene core; wherein the core compound is hydroxylated; wherein the core compound was dissolved in pyridine; wherein the acyl chloride including Tigloyl chloride, angeloyl chloride, Acetyl chloride, Crotonoyl chloride, 3,3-Dimethylacryloyl chloride, senecioyl chloride, Cinnamoyl chloride, Pentenoyl chloride, Hexanoyl chloride, benzoyl chloride and Ethylbutyryl chloride; wherein the reaction time for the mixture is stirred for 5 sec, 1 min, 2 min, 5 min, 10 min, 30 min, 1 hr, 2 hr, 18 hr, 2 days or 3 days; wherein the temperature is 0, 25, 50 or 75° C.; wherein the acid including HCl or the base is a weak base including NaHCO3 is added to the reaction mixture; wherein the solution is then extracted 3 times with ethyl acetate and lyophilization; wherein the reaction product is dissolved in 80% acetonitrile-0.005% trifluoroacetic acid or DMSO; wherein selecting the HPLC fractions for isolation is according to the cytotoxic activity of the reaction product obtained at a reaction time of 5 sec, 1 min, 2 min, 5 min, 10 min, 30 min, 1 hr, 2 hr, 18 hr, 2 days or 3 days.

16. The compound of claim 1, wherein said compound is present in a concentration of 0.01 ug/ml to ug/ml, or wherein said compound is present in a concentration of 0.01 ug/ml to 30 ug/ml, or wherein said compound is present in a concentration of 0.01 ug/ml to 10 ug/ml, or wherein said compound is present in a concentration of 0.01 ug/ml to 5 ug/ml, or wherein said compound is present in a concentration of 5 ug/ml to 10 ug/ml, or wherein said compound is present in a concentration of 0.1 ug/ml to 5 ug/ml, or wherein said compound is present in a concentration of 0.1 ug/ml to 7.5 ug/ml, or wherein said compound is present in a concentration of 0.1 ug/ml to 10 ug/ml, or wherein said compound is present in a concentration of 0.1 ug/ml to 15 ug/ml, or wherein said compound is present in a concentration of 0.1 ug/ml to 20 ug/ml, or wherein said compound is present in a concentration of 0.1 ug/ml to 30 ug/ml, or wherein said compound is present in a concentration of 1 ug/ml to 5 ug/ml, or wherein said compound is present in a concentration of 1 ug/ml to 7.5 ug/ml, or wherein said compound is present in a concentration of 1 ug/ml to 10 ug/ml, or wherein said compound is present in a concentration of 1 ug/ml to 15 ug/ml, or wherein said compound is present in a concentration of 1 ug/ml to 20 ug/ml, or wherein said compound is present in a concentration of 1 ug/ml to 30 ug/ml, or wherein said compound is present in a concentration of 3 ug/ml to 5 ug/ml, or wherein said compound is present in a concentration of 3 ug/ml to 7.5 ug/ml, or wherein said compound is present in a concentration of 3 ug/ml to 10 ug/ml, or wherein said compound is present in a concentration of 3 ug/ml to 15 ug/ml, or wherein said compound is present in a concentration of 3 ug/ml to 20 ug/ml, or wherein said compound is present in a concentration of 3 ug/ml to 30 ug/ml; or present in a concentration of 4 ug/ml to 5 ug/ml, or wherein said compound is present in a concentration of 4 ug/ml to 7.5 ug/ml, or wherein said compound is present in a concentration of 4 ug/ml to 10 ug/ml, or wherein said compound is present in a concentration of 4 ug/ml to 15 ug/ml, or wherein said compound is present in a concentration of 4 ug/ml to 20 ug/ml, or wherein said compound is present in a concentration of 4 ug/ml to 30 ug/ml, or present in a concentration of 5 ug/ml to 8 ug/ml, or wherein said compound is present in a concentration of 5 ug/ml to 9 ug/ml, or wherein said compound is present in a concentration of 5 ug/ml to 10 ug/ml, or wherein said compound is present in a concentration of 5 ug/ml to 15 ug/ml, or wherein said compound is present in a concentration of 5 ug/ml to 20 ug/ml, or wherein said compound is present in a concentration of 5 ug/ml to 30 ug/ml, or present in a concentration of 7 ug/ml to 8 ug/ml, or wherein said compound is present in a concentration of 7 ug/ml to 9 ug/ml, or wherein said compound is present in a concentration of 7 ug/ml to 10 ug/ml, or wherein said compound is present in a concentration of 7 ug/ml to 15 ug/ml, or wherein said compound is present in a concentration of 7 ug/ml to 20 ug/ml, or wherein said compound is present in a concentration of 7 ug/ml to 30 ug/ml; or wherein administration is by intravenous drip: 0.003-0.03 mg/kg body weight of compound dissolved in 250 ml of 10% glucose solution or in 250 ml of 0.9% NaCl solution, or by intravenous injection: 0.003-0.03 mg/kg body weight per day of compound dissolved in 10-20 ml of 10% glucose solution or of 0.9% NaCl solution, or 0.01-0.03 mg/kg body weight of compound dissolved in 250 ml of 10% glucose solution or in 250 ml of 0.9% NaCl solution, or by intravenous injection: 0.01-0.03 mg/kg body weight per day of compound dissolved in 10-20 ml of 10% glucose solution or of 0.9% NaCl solution, or 0.01-0.05 mg/kg body weight of compound dissolved in 250 ml of 10% glucose solution or in 250 ml of 0.9% NaCl solution, or by intravenous injection: 0.01-0.05 mg/kg body weight per day of compound dissolved in 10-20 ml of 10% glucose solution or of 0.9% NaCl solution.

17. A method for inhibiting cancer growth or treating cancer, comprising contacting the cancer cells or administering to a subject having cancer with an effective amount of the compound of claim 1.

18. A method of synthesizing the compound of claim 1, comprising steps of:
  1. Dissolving 40 mg of triterpene core in 1 ml pyridine in a 50 ml tube,
  2. Adding 0.2 ml of acyl chloride comprising Tigloyl chloride and angeloyl chloride,
  3. Stirring the mixture for 1, 2 or 3 days at room temperature,
  4. Adding 3 ml of NaHCO3 is slowly added to the reaction mixture,
  5. Extracting the solution 3 times with 10 ml of ethyl acetate,
  6. Evaporating the solution under vacuum and at 45 C and lyophilization,
  7. Dissolving the reaction product in 80% acetonitrile-0.005% Trifluoroacetic acid,
  8. Selecting the HPLC fractions for isolation according to the cytotoxic activity of times studies and the change of peaks,
  9. Purifying the active esterification products with HPLC.

19. A method of determining cell invasion with the compound of claim 1, comprising the steps of:
  1. Determining the non-cytotoxic concentrations of the compound of claim 1 that is used for the invasion assay,
  2. Exposing cancer cells to different drug concentrations for 1, and 2 days, wherein the cancers are selected from breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer. The growth of cells was measured by MTT assay,
  3. Presenting the optical density (O.D.) of the MTT product (formazan) reflecting cell growth in cells after drug-treatment of day 0, 1 and 2 were measured and plotted (growth curves),
  4. Determining and selecting the concentrations of drug that inhibit 15% cell-growth or less (i.e. 85% of control or above) as compared to the no-drug control (DMSO) are considered non-cytotoxic concentrations,
  5. Seeding Cells (5-10K per well) in a 96-wells plate overnight,
  6. Replacing Culture medium with fresh medium containing different drugs,
  7. Selecting the drug concentrations depends on the non-cytotoxic concentrations,
  8. Using DMSO as the no-drug control,
  9. Cells were incubated for 1 and 2 days,
  10. Measuring Cell growth with MTT assay after 0, 1 or 2 days of incubation,
  11. Incubating the cell cultures with MTT (3-[4,5-Dimethylthiazol-2-yl]-2,5-diphenyl-tetrazolium bromide) (0.5 mg/ml) for 1 h and the formazan formed was dissolved with DMSO; the optical density (O.D.) of formazan at 490 nm was measured,
  12. Plotting the O.D. of samples against the time (days) of incubation (Growth curves),
  13. Determining the concentration of drugs that has no effect on cell growth or reduces 15% or less of control, after 1 day incubation are listed in the following table. These drug concentrations (ug/ml) (or less) are considered as non-cytotoxic are then employed in the invasion assay,
  14. Filling both upper and lower chambers with specific culture medium (according to the requirement of individual cell lines) also containing 10% FBS, wherein an upper and a lower chamber which is separated with a membrane containing a thin layer of reconstituted basement membrane materials (BD BioCoat™ Matrigel™ invasion Chamber system),
  15. Placing samples to both upper and lower chambers, 16. Employing non-cytotoxic drug concentration (determined by the growth curves) in this assay. DMSO was used as the non-drug control,
17. Applying equal numbers (usually 20K per well) of cells into the upper chamber,
18. Counting invasive cells that passed through the membrane from the upper chamber to the lower chamber and attached at the bottom of membrane after 24 hours of incubation which were fixed (with methanol), then stained (with 1% Toluidine Blue), and air dry,
19. Calculating the percentage of invasive cells (as compared to DMSO control),
20. Summarizing the percentage of cells (compared to control) that passed the membrane at certain drug concentration and is listed in table.

20. A method of delivering the compound of claim 1 as medicament with a liposomes or nanoparticles capsules as a carrier, wherein the size of liposomes or nanoparticles capsules is less than 200 nm or 100-200 nm or 50-100 nm or 5-50 nm, wherein the medicament is included but not limited for treating cancer, inhibiting cancer growth, inhibiting cancer invasion, inhibiting cancer metastasis, modulating cell adhesion, modulating cell attachment, or anti adhesion therapy.

21. The compound of claim 1, wherein the compound is an isolated, purified or synthesized compound having structure:

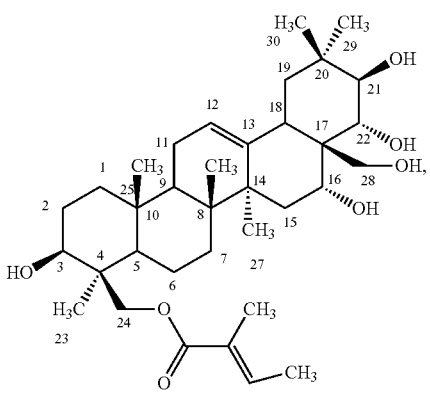

or chemical name: 24-O-Tigloyl-3β,16α,21β,22α,24β,28-hexahydroxyolean-12-ene.

22. The compound of claim 1, wherein the compound is an isolated, purified or synthesized compound having structure:

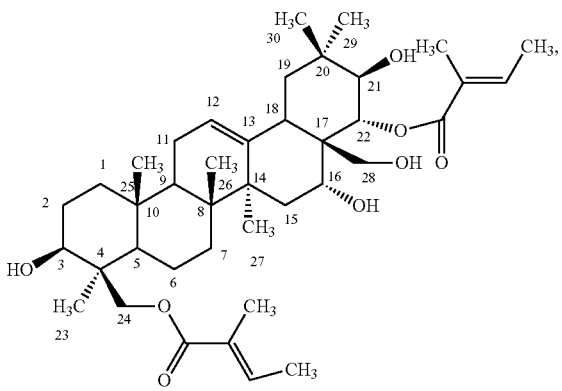

or chemical name: 22,28-O-Tigloyl-3β,16α,21β,22α,24β,28-hexahydroxyolean-12-ene.

23. The compound of claim 1, wherein the compound is an isolated, purified or synthesized compound having structure:

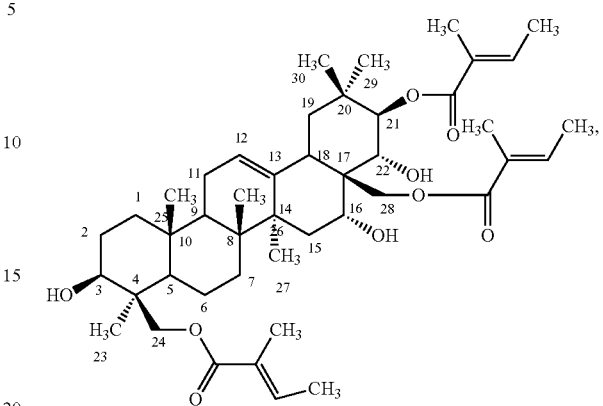

or chemical name: 21,24,28-O-Tigloyl-3β,16α,21β,22α,24β,28-hexahydroxyolean-12-ene.

24. The compound of claim 1, wherein the compound is an isolated, purified or synthesized compound having structure:

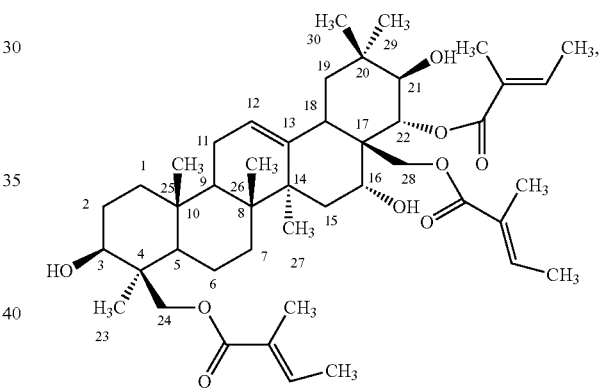

or chemical name: 22,24,28-O-Tigloyl-3β,16α,21β,22α,24β,28-hexahydroxyolean-12-ene.

25. The compound of claim 1, wherein the compound is an isolated, purified or synthesized compound having structure:

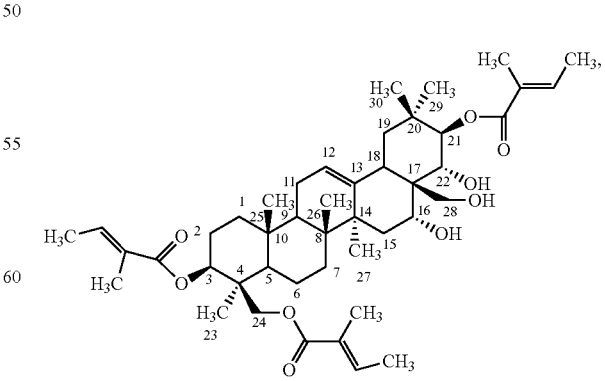

or chemical name: 3,21,28-O-Tigloyl-3β,16α,21β,22α,24β,28-hexahydroxyolean-12-ene.

26. The compound of claim 1, wherein the compound is an isolated, purified or synthesized compound having structure:

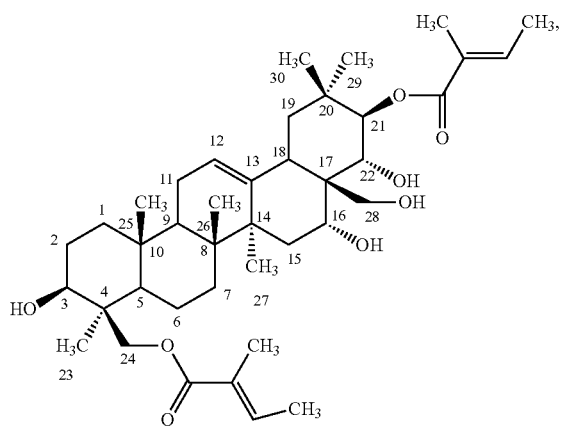

or chemical name: 21,24-O-Tigloyl-3β,16α,21β,22α,24β,28-hexahydroxyolean-12-ene.

27. The compound of claim 1, wherein R10 and 1 or 2 of R1, R2, R3, R4, R5 and R8 are independently attached an O-angeloyl or CH2O-angeloyl.

28. The compound of claim 1, wherein R10 and 1 or 2 of R1, R2, R3, R4, R5 and R8 are independently attached an O-tigloyl or CH2O-tigloyl.

29. The compound of claim 1, wherein R10 and 1 or 2 of R1, R2, R3, R4, R5 and R8 are independently attached an O-senecioyl or CH2O-senecioyl.

30. The compound of claim 1, wherein R10 and 1 or 2 of R1, R2, R3, R4, R5 and R8 are independently attached an O-Crotonoyl or CH2O-Crotonoyl.

31. The compound of claim 1, wherein R10 and 1 or 2 of R1, R2, R3, R4, R5 and R8 are independently attached an O-3,3-Dimethylacryloyl or CH2O-3,3-Dimethylacryloyl.

32. The compound of claim 1, wherein R10 and 1 or 2 of R1, R2, R3, R4, R5 and R8 are independently attached an O-Cinnamoyl or CH2O-Cinnamoyl.

33. The compound of claim 1, wherein R10 and 1 or 2 of R1, R2, R3, R4, R5 and R8 are independently attached an O-Pentenoyl or CH2O-Pentenoyl.

34. The compound of claim 1, wherein R10 and 1 or 2 of R1, R2, R3, R4, R5 and R8 are independently attached an O-Hexanoyl or CH2O-Hexanoyl.

* * * * *

UNITED STATES PATENT AND TRADEMARK OFFICE
CERTIFICATE OF CORRECTION

PATENT NO. : 9,434,677 B2  
APPLICATION NO. : 14/233031  
DATED : September 6, 2016  
INVENTOR(S) : Pui-Kwong Chan and May Sung Mak Page 1 of 1

It is certified that error appears in the above-identified patent and that said Letters Patent is hereby corrected as shown below:

In the Claims

Column 118, line 58, "Concentration of 0.01 ug/ml" should read --concentration of 0.01 ug/ml to 40 ug/ml--

Signed and Sealed this  
Twenty-seventh Day of December, 2016

Michelle K. Lee  
*Director of the United States Patent and Trademark Office*